United States Patent
Watson et al.

(10) Patent No.: US 9,498,363 B2
(45) Date of Patent: Nov. 22, 2016

(54) DELIVERY CATHETER FOR ENDOVASCULAR DEVICE

(71) Applicant: TriVascular, Inc., Santa Rosa, CA (US)

(72) Inventors: James Watson, Santa Rosa, CA (US); Cheng Li, Redwood City, CA (US); Reva Morehous, Cotati, CA (US); Teresa Woodson, Windsor, CA (US); Michael V. Chobotov, Santa Rosa, CA (US); Carl Poppe, Danville, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 472 days.

(21) Appl. No.: 13/835,491

(22) Filed: Mar. 15, 2013

(65) Prior Publication Data

US 2013/0268048 A1 Oct. 10, 2013

Related U.S. Application Data

(60) Provisional application No. 61/621,286, filed on Apr. 6, 2012.

(51) Int. Cl.
*A61F 2/95* (2013.01)
*A61F 2/958* (2013.01)
*A61F 2/07* (2013.01)
*A61F 2/966* (2013.01)

(52) U.S. Cl.
CPC .......... *A61F 2/958* (2013.01); *A61F 2/95* (2013.01); *A61F 2/07* (2013.01); *A61F 2002/077* (2013.01); *A61F 2002/9511* (2013.01); *A61F 2002/9517* (2013.01); *A61F 2002/9665* (2013.01); *A61F 2250/0003* (2013.01)

(58) Field of Classification Search
CPC .......... A61F 2/95; A61F 2/954; A61F 2/958; A61F 2/962; A61F 2/966; A61F 2/97; A61F 2250/0003; A61F 2002/9505; A61F 2002/9511; A61F 2002/9665
USPC ........................... 623/1.11, 1.12, 1.23
See application file for complete search history.

(56) References Cited

U.S. PATENT DOCUMENTS

| | | |
|---|---|---|
| 3,076,737 A | 2/1963 | Roberts |
| 3,540,431 A | 11/1970 | Uddin |
| 3,631,854 A | 1/1972 | Fryer et al. |
| 3,657,744 A | 4/1972 | Ersek |
| 3,669,586 A | 6/1972 | Kramer |

(Continued)

FOREIGN PATENT DOCUMENTS

| | | |
|---|---|---|
| CA | 2438087 | 3/2001 |
| DE | 19624642 | 1/1998 |

(Continued)

OTHER PUBLICATIONS

US 6,413,270, 07/2002, Thornton et al. (withdrawn)

(Continued)

*Primary Examiner* — Kathleen Holwerda
(74) *Attorney, Agent, or Firm* — Anderson, IP, Inc.

(57) ABSTRACT

Some embodiments relate in part to endovascular prostheses and delivery catheter systems and methods for deploying same. Embodiments may be directed more specifically to graft bodies having self-expanding members, including inflatable graft bodies, and catheters and methods for deploying same within the body of a patient.

15 Claims, 19 Drawing Sheets

(56) References Cited

U.S. PATENT DOCUMENTS

| | | |
|---|---|---|
| 3,814,137 A | 6/1974 | Martinez |
| 3,818,511 A | 6/1974 | Goldberg et al. |
| 3,902,198 A | 9/1975 | Cooper |
| 3,991,767 A | 11/1976 | Miller et al. |
| 4,096,227 A | 6/1978 | Gore |
| 4,110,392 A | 8/1978 | Yamazaki |
| 4,140,126 A | 2/1979 | Choudhury |
| 4,183,102 A | 1/1980 | Guiset |
| 4,187,390 A | 2/1980 | Gore |
| 4,208,745 A | 6/1980 | Okita |
| 4,214,587 A | 7/1980 | Sakura, Jr. |
| 4,229,838 A | 10/1980 | Mano |
| 4,248,924 A | 2/1981 | Okita |
| 4,385,093 A | 5/1983 | Hubis |
| 4,416,028 A | 11/1983 | Eriksson et al. |
| 4,434,797 A | 3/1984 | Silander |
| 4,459,252 A | 7/1984 | MacGregor |
| 4,474,630 A | 10/1984 | Planck et al. |
| 4,478,665 A | 10/1984 | Hubis |
| 4,482,516 A | 11/1984 | Bowman et al. |
| 4,497,074 A | 2/1985 | Rey et al. |
| 4,503,569 A | 3/1985 | Dotter |
| 4,512,338 A | 4/1985 | Balko et al. |
| 4,550,447 A | 11/1985 | Seiler, Jr. et al. |
| 4,552,707 A | 11/1985 | How |
| 4,562,596 A | 1/1986 | Kornberg |
| 4,577,631 A | 3/1986 | Kreamer |
| 4,580,568 A | 4/1986 | Gianturco |
| 4,592,754 A | 6/1986 | Gupte et al. |
| 4,617,932 A | 10/1986 | Kornberg |
| 4,647,416 A | 3/1987 | Seiler, Jr. et al. |
| 4,655,769 A | 4/1987 | Zachariades |
| 4,655,771 A | 4/1987 | Wallsten |
| 4,662,883 A | 5/1987 | Bell et al. |
| 4,665,906 A | 5/1987 | Jervis |
| 4,705,517 A | 11/1987 | DiPisa, Jr. |
| 4,731,073 A | 3/1988 | Robinson |
| 4,733,665 A | 3/1988 | Palmaz |
| 4,739,762 A | 4/1988 | Palmaz |
| 4,740,207 A | 4/1988 | Kreamer |
| 4,743,480 A | 5/1988 | Campbell et al. |
| 4,760,102 A | 7/1988 | Moriyama et al. |
| 4,776,337 A | 10/1988 | Palmaz |
| 4,787,899 A | 11/1988 | Lazarus |
| 4,816,028 A | 3/1989 | Kapadia et al. |
| 4,830,003 A | 5/1989 | Wolff et al. |
| 4,856,516 A | 8/1989 | Hillstead |
| 4,871,365 A | 10/1989 | Dumican |
| 4,877,661 A | 10/1989 | House et al. |
| 4,902,423 A | 2/1990 | Bacino |
| 4,932,938 A | 6/1990 | Goldberg et al. |
| 4,941,870 A | 7/1990 | Okada et al. |
| 4,955,899 A | 9/1990 | Della et al. |
| 4,957,669 A | 9/1990 | Primm |
| 4,985,296 A | 1/1991 | Mortimer, Jr. |
| 4,994,071 A | 2/1991 | MacGregor |
| 4,994,077 A | 2/1991 | Dobben |
| 5,019,090 A | 5/1991 | Pinchuk |
| 5,041,126 A | 8/1991 | Gianturco |
| 5,052,998 A | 10/1991 | Zimmon |
| 5,059,211 A | 10/1991 | Stack et al. |
| 5,064,435 A | 11/1991 | Porter |
| 5,098,625 A | 3/1992 | Huang et al. |
| 5,100,422 A | 3/1992 | Berguer et al. |
| 5,104,399 A | 4/1992 | Lazarus |
| 5,104,400 A | 4/1992 | Berguer et al. |
| 5,104,404 A | 4/1992 | Wolff |
| 5,108,424 A | 4/1992 | Hoffman, Jr. et al. |
| 5,110,527 A | 5/1992 | Harada et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,139,480 A | 8/1992 | Hickle et al. |
| 5,150,304 A | 9/1992 | Berchem et al. |
| 5,151,105 A | 9/1992 | Kwan-Gett |
| 5,152,782 A | 10/1992 | Kowligi et al. |
| 5,156,620 A * | 10/1992 | Pigott .......................... 623/1.25 |
| 5,158,548 A | 10/1992 | Lau et al. |
| 5,163,955 A | 11/1992 | Love |
| 5,167,614 A | 12/1992 | Tessmann |
| 5,171,262 A | 12/1992 | MacGregor |
| 5,181,921 A | 1/1993 | Makita et al. |
| 5,192,310 A | 3/1993 | Herweck et al. |
| 5,195,984 A | 3/1993 | Schatz |
| 5,197,976 A | 3/1993 | Herweck et al. |
| 5,197,978 A | 3/1993 | Hess |
| 5,201,757 A | 4/1993 | Heyn et al. |
| 5,202,352 A | 4/1993 | Okada et al. |
| 5,207,695 A | 5/1993 | Trout, III |
| 5,217,483 A | 6/1993 | Tower |
| 5,219,355 A | 6/1993 | Parodi et al. |
| 5,226,913 A | 7/1993 | Pinchuk |
| 5,234,456 A | 8/1993 | Silvestini |
| 5,250,059 A | 10/1993 | Andreas et al. |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,290,305 A | 3/1994 | Inoue |
| 5,292,331 A | 3/1994 | Boneau |
| 5,304,200 A | 4/1994 | Spaulding |
| 5,314,472 A | 5/1994 | Fontaine |
| 5,316,023 A | 5/1994 | Palmaz et al. |
| 5,320,100 A | 6/1994 | Herweck et al. |
| 5,321,109 A | 6/1994 | Bosse et al. |
| 5,330,528 A | 7/1994 | Lazim |
| 5,334,164 A | 8/1994 | Guy et al. |
| 5,334,201 A | 8/1994 | Cowan |
| 5,344,426 A | 9/1994 | Lau et al. |
| 5,344,444 A | 9/1994 | Glastra |
| 5,344,451 A | 9/1994 | Dayton |
| 5,350,398 A | 9/1994 | Pavcnik |
| 5,354,310 A | 10/1994 | Garnic et al. |
| 5,354,329 A | 10/1994 | Whalen |
| 5,360,443 A | 11/1994 | Barone et al. |
| 5,365,996 A | 11/1994 | Crook |
| 5,366,504 A | 11/1994 | Andersen et al. |
| 5,370,682 A | 12/1994 | Schmitt |
| 5,370,691 A | 12/1994 | Samson |
| 5,374,473 A | 12/1994 | Knox et al. |
| 5,382,261 A | 1/1995 | Palmaz |
| 5,383,892 A | 1/1995 | Cardon et al. |
| 5,383,928 A | 1/1995 | Scott et al. |
| 5,387,235 A | 2/1995 | Chuter et al. |
| 5,389,106 A | 2/1995 | Tower et al. |
| 5,391,147 A | 2/1995 | Imran et al. |
| 5,397,345 A | 3/1995 | Lazarus |
| 5,405,377 A | 4/1995 | Cragg |
| 5,405,378 A | 4/1995 | Strecker |
| 5,405,379 A | 4/1995 | Lane |
| 5,411,550 A | 5/1995 | Herweck et al. |
| 5,415,634 A | 5/1995 | Glynn et al. |
| 5,423,851 A | 6/1995 | Samuels |
| 5,433,909 A | 7/1995 | Martakos et al. |
| 5,437,900 A | 8/1995 | Kuzowski |
| 5,441,515 A | 8/1995 | Khosravi et al. |
| 5,443,458 A | 8/1995 | Eury |
| 5,443,498 A | 8/1995 | Fontaine |
| 5,445,646 A | 8/1995 | Euteneuer et al. |
| 5,447,152 A | 9/1995 | Kohsai et al. |
| 5,449,373 A | 9/1995 | Pinchasik et al. |
| 5,456,713 A | 10/1995 | Chuter |
| 5,464,419 A | 11/1995 | Glastra |
| 5,464,449 A | 11/1995 | Ryan et al. |
| 5,466,509 A | 11/1995 | Kowllgi et al. |
| 5,474,824 A | 12/1995 | Martakos et al. |
| 5,476,506 A | 12/1995 | Lunn |
| 5,476,589 A | 12/1995 | Bacino |
| 5,478,330 A | 12/1995 | Imran et al. |
| 5,480,423 A | 1/1996 | Ravenscroft et al. |
| 5,489,295 A | 2/1996 | Piplani et al. |
| 5,505,887 A | 4/1996 | Zdrahala et al. |

(56) References Cited

U.S. PATENT DOCUMENTS

| | | |
|---|---|---|
| 5,507,769 A | 4/1996 | Marin et al. |
| 5,507,770 A | 4/1996 | Turk |
| 5,512,360 A | 4/1996 | King |
| 5,514,154 A | 5/1996 | Lau et al. |
| 5,522,880 A | 6/1996 | Barone et al. |
| 5,522,881 A | 6/1996 | Lentz |
| 5,522,883 A | 6/1996 | Slater et al. |
| 5,524,633 A | 6/1996 | Heaven et al. |
| 5,527,353 A | 6/1996 | Schmitt |
| 5,527,355 A | 6/1996 | Ahn |
| 5,529,653 A | 6/1996 | Glastra |
| 5,529,820 A | 6/1996 | Nomi et al. |
| 5,534,024 A | 7/1996 | Rogers et al. |
| 5,536,274 A | 7/1996 | Neuss |
| 5,545,135 A | 8/1996 | Iacob et al. |
| 5,549,662 A | 8/1996 | Fordenbacher |
| 5,549,663 A | 8/1996 | Cottone, Jr. |
| 5,552,100 A | 9/1996 | Shannon et al. |
| 5,554,180 A | 9/1996 | Turk |
| 5,554,181 A | 9/1996 | Das |
| 5,554,183 A | 9/1996 | Nazari |
| 5,554,185 A | 9/1996 | Block et al. |
| 5,556,414 A | 9/1996 | Turi |
| 5,556,426 A | 9/1996 | Popadiuk et al. |
| 5,560,986 A | 10/1996 | Mortimer, Jr. |
| 5,562,697 A | 10/1996 | Christiansen |
| 5,562,724 A | 10/1996 | Vorwerk et al. |
| 5,562,726 A | 10/1996 | Chuter |
| 5,562,727 A | 10/1996 | Turk et al. |
| 5,562,728 A | 10/1996 | Lazarus et al. |
| 5,569,295 A | 10/1996 | Lam |
| 5,571,171 A | 11/1996 | Barone et al. |
| 5,571,172 A | 11/1996 | Chin |
| 5,571,173 A | 11/1996 | Parodi |
| 5,575,817 A | 11/1996 | Martin |
| 5,575,818 A | 11/1996 | Pinchuk |
| 5,578,071 A | 11/1996 | Parodi |
| 5,578,072 A | 11/1996 | Barone et al. |
| 5,588,964 A | 12/1996 | Imran et al. |
| 5,591,195 A | 1/1997 | Taheri et al. |
| 5,591,197 A | 1/1997 | Orth et al. |
| 5,591,229 A | 1/1997 | Parodi |
| 5,597,378 A | 1/1997 | Jervis |
| 5,603,721 A | 2/1997 | Lau et al. |
| 5,605,543 A * | 2/1997 | Swanson .................. 604/102.02 |
| 5,607,478 A | 3/1997 | Lentz et al. |
| 5,609,624 A | 3/1997 | Kalis |
| 5,609,625 A | 3/1997 | Piplani et al. |
| 5,609,627 A | 3/1997 | Goicoechea et al. |
| 5,609,628 A | 3/1997 | Keranen |
| 5,609,629 A | 3/1997 | Fearnont et al. |
| 5,612,885 A | 3/1997 | Love |
| 5,618,301 A | 4/1997 | Hauenstein et al. |
| 5,620,763 A | 4/1997 | House et al. |
| 5,626,599 A | 5/1997 | Bourne et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,632,772 A | 5/1997 | Alcime et al. |
| 5,632,840 A | 5/1997 | Campbell |
| 5,639,278 A | 6/1997 | Dereume et al. |
| 5,641,373 A | 6/1997 | Shannon et al. |
| 5,645,915 A | 7/1997 | Kranzler et al. |
| 5,649,978 A | 7/1997 | Samson |
| 5,653,745 A | 8/1997 | Trescony et al. |
| 5,653,746 A | 8/1997 | Schmitt |
| 5,656,029 A | 8/1997 | Imran et al. |
| 5,662,675 A | 9/1997 | Polanskyj Stockert et al. |
| 5,662,700 A | 9/1997 | Lazarus |
| 5,665,115 A | 9/1997 | Cragg |
| 5,665,117 A | 9/1997 | Rhodes |
| 5,667,523 A | 9/1997 | Bynon et al. |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,681,346 A | 10/1997 | Orth et al. |
| 5,683,449 A | 11/1997 | Marcade |
| 5,683,451 A | 11/1997 | Lenker et al. |
| 5,683,452 A | 11/1997 | Barone et al. |
| 5,683,453 A | 11/1997 | Palmaz |
| 5,690,644 A | 11/1997 | Yurek et al. |
| 5,693,083 A | 12/1997 | Baker et al. |
| 5,693,084 A | 12/1997 | Chuter |
| 5,693,087 A | 12/1997 | Parodi |
| 5,693,088 A | 12/1997 | Lazarus |
| 5,697,968 A | 12/1997 | Rogers et al. |
| 5,697,971 A | 12/1997 | Fischell et al. |
| 5,700,285 A | 12/1997 | Myers et al. |
| 5,707,378 A | 1/1998 | Ahn et al. |
| 5,707,388 A | 1/1998 | Lauterjung |
| 5,708,044 A | 1/1998 | Branca |
| 5,709,701 A | 1/1998 | Parodi |
| 5,709,703 A | 1/1998 | Lukic et al. |
| 5,712,315 A | 1/1998 | Dolan |
| 5,713,917 A | 2/1998 | Leonhardt et al. |
| 5,716,393 A | 2/1998 | Lindenberg et al. |
| 5,716,395 A | 2/1998 | Myers et al. |
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,725,547 A | 3/1998 | Chuter |
| 5,725,549 A | 3/1998 | Lam |
| 5,728,131 A | 3/1998 | Frantzen et al. |
| 5,733,303 A | 3/1998 | Israel et al. |
| 5,733,325 A | 3/1998 | Robinson et al. |
| 5,735,892 A | 4/1998 | Myers et al. |
| 5,735,893 A | 4/1998 | Lau et al. |
| 5,735,897 A | 4/1998 | Buirge |
| 5,741,324 A | 4/1998 | Glastra |
| 5,741,325 A | 4/1998 | Chaikof et al. |
| 5,741,327 A | 4/1998 | Frantzen |
| 5,747,128 A | 5/1998 | Campbell et al. |
| 5,749,880 A | 5/1998 | Banas et al. |
| 5,749,894 A | 5/1998 | Engelson |
| 5,749,920 A | 5/1998 | Quiachon et al. |
| 5,749,921 A | 5/1998 | Lenker et al. |
| 5,755,772 A | 5/1998 | Evans et al. |
| 5,755,776 A | 5/1998 | Al-Saadon |
| 5,766,203 A | 6/1998 | Imran et al. |
| 5,769,882 A | 6/1998 | Fogarty et al. |
| 5,769,885 A | 6/1998 | Quiachon et al. |
| 5,769,887 A | 6/1998 | Brown et al. |
| 5,772,884 A | 6/1998 | Tanaka et al. |
| 5,776,142 A | 7/1998 | Gunderson |
| 5,776,161 A | 7/1998 | Globerman |
| 5,776,183 A | 7/1998 | Kanesaka et al. |
| 5,780,807 A | 7/1998 | Saunders |
| 5,782,789 A | 7/1998 | Herweck et al. |
| 5,782,838 A | 7/1998 | Beyar et al. |
| 5,782,904 A | 7/1998 | White et al. |
| 5,782,909 A | 7/1998 | Quiachon et al. |
| 5,785,679 A | 7/1998 | Abolfathi et al. |
| 5,788,626 A | 8/1998 | Thompson |
| 5,789,047 A | 8/1998 | Sasaki et al. |
| 5,797,951 A | 8/1998 | Mueller |
| 5,798,924 A | 8/1998 | Eufinger et al. |
| 5,799,384 A | 9/1998 | Schwartz et al. |
| 5,800,508 A | 9/1998 | Goicoechea et al. |
| 5,800,512 A | 9/1998 | Lentz et al. |
| 5,800,515 A | 9/1998 | Nadal et al. |
| 5,800,518 A | 9/1998 | Piplani et al. |
| 5,800,522 A | 9/1998 | Campbell et al. |
| 5,800,524 A | 9/1998 | Borghi |
| 5,800,526 A | 9/1998 | Anderson et al. |
| 5,810,870 A | 9/1998 | Myers et al. |
| 5,810,872 A | 9/1998 | Kanesaka et al. |
| 5,814,405 A | 9/1998 | Branca et al. |
| 5,817,102 A | 10/1998 | Johnson et al. |
| 5,824,037 A | 10/1998 | Fogarty et al. |
| 5,824,039 A | 10/1998 | Piplani et al. |
| 5,824,041 A | 10/1998 | Lenker et al. |

(56) References Cited

U.S. PATENT DOCUMENTS

| | | |
|---|---|---|
| 5,824,042 A | 10/1998 | Lombardi et al. |
| 5,824,044 A | 10/1998 | Quiachon et al. |
| 5,824,046 A | 10/1998 | Smith et al. |
| 5,824,058 A | 10/1998 | Ravenscroft et al. |
| 5,827,289 A | 10/1998 | Reiley et al. |
| 5,827,310 A | 10/1998 | Marin |
| 5,827,320 A | 10/1998 | Richter et al. |
| 5,827,321 A | 10/1998 | Roubin et al. |
| 5,833,651 A | 11/1998 | Donovan et al. |
| 5,833,707 A | 11/1998 | McIntyre et al. |
| 5,836,964 A | 11/1998 | Richter et al. |
| 5,836,966 A | 11/1998 | St. Germain |
| 5,840,775 A | 11/1998 | Howard, Jr. et al. |
| 5,843,158 A | 12/1998 | Lenker et al. |
| 5,843,160 A | 12/1998 | Rhodes |
| 5,843,162 A | 12/1998 | Inoue |
| 5,843,164 A | 12/1998 | Frantzen et al. |
| 5,843,166 A | 12/1998 | Lentz et al. |
| 5,843,167 A | 12/1998 | Dwyer et al. |
| 5,843,170 A | 12/1998 | Ahn |
| 5,843,173 A | 12/1998 | Shannon et al. |
| 5,843,175 A | 12/1998 | Frantzen |
| 5,853,419 A | 12/1998 | Imran |
| 5,855,598 A | 1/1999 | Pinchuk |
| 5,858,556 A | 1/1999 | Eckert et al. |
| 5,860,998 A | 1/1999 | Robinson et al. |
| 5,861,027 A | 1/1999 | Trapp |
| 5,871,536 A | 2/1999 | Lazarus |
| 5,871,537 A | 2/1999 | Holman et al. |
| 5,871,538 A | 2/1999 | Dereume |
| 5,873,906 A | 2/1999 | Lau et al. |
| 5,876,432 A | 3/1999 | Lau et al. |
| 5,891,193 A | 4/1999 | Robinson et al. |
| 5,904,713 A | 5/1999 | Leschinsky |
| 5,906,619 A | 5/1999 | Olson et al. |
| 5,906,641 A | 5/1999 | Thompson et al. |
| 5,910,168 A | 6/1999 | Myers et al. |
| 5,910,277 A | 6/1999 | Ishino et al. |
| 5,911,754 A | 6/1999 | Kanesaka et al. |
| 5,916,264 A | 6/1999 | Von Oepen et al. |
| 5,919,204 A | 7/1999 | Lukic et al. |
| 5,922,020 A | 7/1999 | Klein et al. |
| 5,925,061 A | 7/1999 | Ogi et al. |
| 5,925,075 A | 7/1999 | Myers et al. |
| 5,931,865 A | 8/1999 | Silverman et al. |
| 5,935,667 A | 8/1999 | Calcote et al. |
| 5,939,198 A | 8/1999 | Howard, Jr. et al. |
| 5,944,750 A | 8/1999 | Tanner et al. |
| 5,948,016 A | 9/1999 | Jang |
| 5,954,729 A | 9/1999 | Bachmann et al. |
| 5,955,016 A | 9/1999 | Goldfarb |
| 5,957,973 A | 9/1999 | Quiachon et al. |
| 5,961,545 A | 10/1999 | Lentz et al. |
| 5,961,546 A | 10/1999 | Robinson et al. |
| 5,968,068 A | 10/1999 | Dehdashtian et al. |
| 5,968,090 A | 10/1999 | Ratcliff et al. |
| 5,972,023 A | 10/1999 | Tanner et al. |
| 5,972,027 A | 10/1999 | Johnson |
| 5,972,441 A | 10/1999 | Campbell et al. |
| 5,976,155 A | 11/1999 | Foreman et al. |
| 5,976,179 A | 11/1999 | Inoue |
| 5,976,192 A | 11/1999 | McIntyre et al. |
| 5,976,650 A | 11/1999 | Campbell et al. |
| 5,980,530 A | 11/1999 | Willard et al. |
| 5,980,570 A | 11/1999 | Simpson |
| 5,984,955 A | 11/1999 | Wisselink |
| 5,984,956 A | 11/1999 | Tweden et al. |
| 5,984,964 A | 11/1999 | Roberts et al. |
| 5,989,287 A | 11/1999 | Yang et al. |
| 5,993,481 A | 11/1999 | Marcade et al. |
| 5,993,489 A | 11/1999 | Lewis et al. |
| 5,997,573 A | 12/1999 | Quijano et al. |
| 6,001,123 A | 12/1999 | Lau |
| 6,004,346 A | 12/1999 | Wolff et al. |
| 6,004,347 A | 12/1999 | McNamara et al. |
| 6,004,348 A | 12/1999 | Banas et al. |
| 6,007,575 A | 12/1999 | Samuels |
| 6,015,429 A | 1/2000 | Lau et al. |
| 6,015,431 A | 1/2000 | Thornton et al. |
| 6,015,432 A | 1/2000 | Rakos et al. |
| 6,017,362 A | 1/2000 | Lau |
| 6,017,364 A | 1/2000 | Lazarus |
| 6,019,778 A | 2/2000 | Wilson et al. |
| 6,019,779 A | 2/2000 | Thorud et al. |
| 6,019,787 A | 2/2000 | Richard et al. |
| 6,022,359 A | 2/2000 | Frantzen |
| 6,024,763 A | 2/2000 | Lenker et al. |
| 6,025,044 A | 2/2000 | Campbell et al. |
| 6,027,779 A | 2/2000 | Campbell et al. |
| 6,027,811 A | 2/2000 | Campbell et al. |
| 6,030,413 A | 2/2000 | Lazarus |
| 6,030,414 A | 2/2000 | Taheri |
| 6,030,415 A | 2/2000 | Chuter |
| 6,036,640 A | 3/2000 | Corace et al. |
| 6,036,702 A | 3/2000 | Bachinski et al. |
| 6,036,723 A | 3/2000 | Anidjar et al. |
| 6,036,724 A | 3/2000 | Lentz et al. |
| 6,036,725 A | 3/2000 | Avellanet |
| 6,039,754 A | 3/2000 | Caro |
| 6,039,758 A | 3/2000 | Quiachon et al. |
| 6,042,589 A | 3/2000 | Marianne |
| 6,042,605 A | 3/2000 | Martin et al. |
| 6,042,606 A | 3/2000 | Frantzen |
| 6,045,557 A | 4/2000 | White et al. |
| 6,048,484 A | 4/2000 | House et al. |
| 6,051,020 A | 4/2000 | Goicoechea et al. |
| 6,053,943 A | 4/2000 | Edwin et al. |
| 6,059,821 A | 5/2000 | Anidjar et al. |
| 6,059,823 A | 5/2000 | Holman et al. |
| 6,060,534 A | 5/2000 | Ronan et al. |
| 6,063,114 A | 5/2000 | Nash et al. |
| 6,068,626 A | 5/2000 | Harrington et al. |
| 6,070,589 A | 6/2000 | Keith et al. |
| 6,074,341 A | 6/2000 | Anderson et al. |
| 6,075,180 A | 6/2000 | Sharber et al. |
| 6,077,296 A | 6/2000 | Shokoohi et al. |
| 6,077,297 A | 6/2000 | Robinson et al. |
| 6,077,298 A | 6/2000 | Tu et al. |
| 6,090,128 A | 7/2000 | Douglas |
| 6,093,203 A | 7/2000 | Uflacker |
| 6,096,052 A | 8/2000 | Callister et al. |
| 6,096,070 A | 8/2000 | Ragheb et al. |
| 6,098,630 A | 8/2000 | Papazoglou |
| 6,102,918 A | 8/2000 | Kerr |
| 6,102,938 A | 8/2000 | Evans et al. |
| 6,102,940 A | 8/2000 | Robichon et al. |
| 6,103,172 A | 8/2000 | Newman et al. |
| 6,106,548 A | 8/2000 | Roubin et al. |
| 6,110,198 A | 8/2000 | Fogarty et al. |
| 6,113,628 A | 9/2000 | Borghi |
| 6,117,168 A | 9/2000 | Yang et al. |
| 6,123,722 A | 9/2000 | Fogarty et al. |
| 6,124,523 A | 9/2000 | Banas et al. |
| 6,126,685 A | 10/2000 | Lenker et al. |
| 6,129,756 A | 10/2000 | Kugler et al. |
| 6,132,457 A | 10/2000 | Chobotov |
| 6,132,459 A | 10/2000 | Piplani et al. |
| 6,139,572 A | 10/2000 | Campbell et al. |
| 6,142,973 A | 11/2000 | Carleton et al. |
| 6,143,014 A | 11/2000 | Dehdashtian et al. |
| 6,143,015 A | 11/2000 | Nobles |
| 6,143,016 A | 11/2000 | Bleam et al. |
| 6,143,021 A | 11/2000 | Staehle |
| 6,143,022 A | 11/2000 | Shull et al. |
| 6,146,389 A | 11/2000 | Geitz |
| 6,146,416 A | 11/2000 | Andersen et al. |
| 6,146,417 A | 11/2000 | Ischinger |
| 6,149,665 A | 11/2000 | Gabbay |
| 6,149,681 A | 11/2000 | Houser et al. |
| 6,149,682 A | 11/2000 | Frid |
| 6,152,944 A | 11/2000 | Holman et al. |
| 6,152,956 A | 11/2000 | Pierce |
| 6,156,063 A | 12/2000 | Douglas |
| 6,156,064 A | 12/2000 | Chouinard |

(56) References Cited

U.S. PATENT DOCUMENTS

| | | | |
|---|---|---|---|
| 6,159,229 A | 12/2000 | Jendersee et al. |
| 6,159,237 A | 12/2000 | Alt et al. |
| 6,159,238 A | 12/2000 | Killion et al. |
| 6,159,239 A | 12/2000 | Greenhalgh |
| 6,159,565 A | 12/2000 | Campbell et al. |
| 6,162,243 A | 12/2000 | Gray et al. |
| 6,162,245 A | 12/2000 | Jayaraman |
| 6,162,246 A | 12/2000 | Barone |
| 6,165,210 A | 12/2000 | Lau et al. |
| 6,165,211 A | 12/2000 | Thompson |
| 6,165,212 A | 12/2000 | Dereume et al. |
| 6,165,213 A | 12/2000 | Goicoechea et al. |
| 6,165,214 A | 12/2000 | Lazarus |
| 6,168,610 B1 | 1/2001 | Marin et al. |
| 6,168,614 B1 | 1/2001 | Andersen et al. |
| 6,168,616 B1 | 1/2001 | Brown, III |
| 6,168,617 B1 | 1/2001 | Blaeser et al. |
| 6,168,618 B1 | 1/2001 | Frantzen |
| 6,168,619 B1 | 1/2001 | Dinh et al. |
| 6,168,620 B1 | 1/2001 | Kerr |
| 6,174,326 B1 | 1/2001 | Kitaoka et al. |
| 6,183,481 B1 | 2/2001 | Lee et al. |
| 6,183,504 B1 | 2/2001 | Inoue |
| 6,187,034 B1 | 2/2001 | Frantzen |
| 6,187,036 B1 | 2/2001 | Shaolian et al. |
| 6,187,054 B1 | 2/2001 | Colone et al. |
| 6,193,745 B1 | 2/2001 | Fogarty et al. |
| 6,196,230 B1 | 3/2001 | Hall et al. |
| 6,197,046 B1 | 3/2001 | Piplani et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,203,569 B1 | 3/2001 | Wijay |
| 6,203,735 B1 | 3/2001 | Edwin et al. |
| 6,203,779 B1 | 3/2001 | Ricci et al. |
| 6,210,422 B1 | 4/2001 | Douglas |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,039 B1 | 4/2001 | Banas et al. |
| 6,217,608 B1 | 4/2001 | Penn et al. |
| 6,221,102 B1 | 4/2001 | Baker et al. |
| 6,224,609 B1 | 5/2001 | Ressemann et al. |
| 6,231,562 B1 | 5/2001 | Khosravi et al. |
| 6,235,050 B1 | 5/2001 | Quiachon et al. |
| 6,235,051 B1 | 5/2001 | Murphy |
| 6,238,432 B1 | 5/2001 | Parodi |
| 6,240,616 B1 | 6/2001 | Yan |
| 6,241,759 B1 | 6/2001 | Piplani et al. |
| 6,245,097 B1 | 6/2001 | Inoue |
| 6,245,099 B1 | 6/2001 | Edwin et al. |
| 6,245,100 B1 | 6/2001 | Davila et al. |
| 6,245,101 B1 | 6/2001 | Drasler et al. |
| 6,245,102 B1 | 6/2001 | Jayaraman |
| 6,248,116 B1 | 6/2001 | Chevillon et al. |
| 6,251,132 B1 | 6/2001 | Ravenscroft et al. |
| 6,251,136 B1 | 6/2001 | Guruwaiya et al. |
| 6,254,593 B1 | 7/2001 | Wilson |
| 6,254,632 B1 | 7/2001 | Wu et al. |
| 6,258,073 B1 | 7/2001 | Mauch |
| 6,258,114 B1 | 7/2001 | Konya et al. |
| 6,258,116 B1 | 7/2001 | Hojeibane |
| 6,261,316 B1 | 7/2001 | Shaolian et al. |
| 6,261,317 B1 | 7/2001 | Inoue |
| 6,264,662 B1 | 7/2001 | Lauterjung |
| 6,264,684 B1 | 7/2001 | Banas et al. |
| 6,267,783 B1 | 7/2001 | Letendre et al. |
| 6,267,834 B1 | 7/2001 | Shannon et al. |
| 6,270,524 B1 | 8/2001 | Kim |
| 6,270,525 B1 | 8/2001 | Letendre et al. |
| 6,270,707 B1 | 8/2001 | Hori et al. |
| 6,273,909 B1 | 8/2001 | Kugler et al. |
| 6,273,910 B1 | 8/2001 | Limon |
| 6,273,911 B1 | 8/2001 | Cox et al. |
| 6,280,457 B1 | 8/2001 | Wallace et al. |
| 6,280,466 B1 | 8/2001 | Kugler et al. |
| 6,280,467 B1 | 8/2001 | Leonhardt et al. |
| 6,283,991 B1 | 9/2001 | Cox et al. |
| 6,287,315 B1 | 9/2001 | Wijeratne et al. |
| 6,287,329 B1 | 9/2001 | Duerig et al. |
| 6,287,330 B1 | 9/2001 | Johansson et al. |
| 6,287,335 B1 | 9/2001 | Drasler et al. |
| 6,287,336 B1 | 9/2001 | Globerman et al. |
| 6,290,728 B1 | 9/2001 | Phelps et al. |
| 6,293,966 B1 | 9/2001 | Frantzen |
| 6,293,968 B1 * | 9/2001 | Taheri .................... 623/1.15 |
| 6,293,969 B1 | 9/2001 | Chuter |
| 6,296,661 B1 | 10/2001 | Davila et al. |
| 6,302,891 B1 | 10/2001 | Nadal |
| 6,302,905 B1 | 10/2001 | Goldstein et al. |
| 6,302,906 B1 | 10/2001 | Goicoechea et al. |
| 6,302,908 B1 | 10/2001 | Parodi |
| 6,303,100 B1 | 10/2001 | Ricci et al. |
| 6,306,141 B1 | 10/2001 | Jervis |
| 6,306,145 B1 | 10/2001 | Laschinsky |
| 6,306,164 B1 | 10/2001 | Kujawski |
| 6,306,165 B1 | 10/2001 | Patnaik et al. |
| 6,312,458 B1 | 11/2001 | Golds |
| 6,312,460 B2 | 11/2001 | Drasler et al. |
| 6,312,462 B1 | 11/2001 | McDermott et al. |
| 6,315,791 B1 | 11/2001 | Gingras et al. |
| 6,319,276 B1 | 11/2001 | Holman et al. |
| 6,319,278 B1 | 11/2001 | Quinn |
| 6,319,279 B1 | 11/2001 | Shannon et al. |
| 6,322,587 B1 | 11/2001 | Quiachon et al. |
| 6,325,819 B1 | 12/2001 | Pavcnik et al. |
| 6,325,823 B1 | 12/2001 | Horzewski et al. |
| 6,325,824 B2 | 12/2001 | Limon |
| 6,325,825 B1 | 12/2001 | Kula et al. |
| 6,328,762 B1 | 12/2001 | Anderson et al. |
| 6,331,186 B1 | 12/2001 | Wang et al. |
| 6,331,188 B1 | 12/2001 | Lau et al. |
| 6,331,190 B1 | 12/2001 | Shokoohi et al. |
| 6,331,191 B1 | 12/2001 | Chobotov |
| 6,334,869 B1 | 1/2002 | Leonhardt et al. |
| 6,336,937 B1 | 1/2002 | Vonesh et al. |
| 6,344,044 B1 | 2/2002 | Fulkerson et al. |
| 6,344,054 B1 | 2/2002 | Parodi |
| 6,344,055 B1 | 2/2002 | Shukov |
| 6,346,118 B1 | 2/2002 | Baker et al. |
| 6,346,119 B1 | 2/2002 | Kuwahara et al. |
| 6,348,065 B1 | 2/2002 | Brown et al. |
| 6,350,277 B1 | 2/2002 | Kocur |
| 6,352,553 B1 | 3/2002 | Van der Burg et al. |
| 6,352,561 B1 | 3/2002 | Leopold et al. |
| 6,355,055 B1 | 3/2002 | Waksman et al. |
| 6,355,056 B1 | 3/2002 | Pnheiro |
| 6,355,060 B1 | 3/2002 | Lenker et al. |
| 6,355,063 B1 | 3/2002 | Calcote |
| 6,357,104 B1 | 3/2002 | Myers |
| 6,358,276 B1 | 3/2002 | Edwin et al. |
| 6,358,284 B1 | 3/2002 | Fearnot et al. |
| 6,361,637 B2 | 3/2002 | Martin et al. |
| 6,363,938 B2 | 4/2002 | Saadat |
| 6,364,856 B1 | 4/2002 | Ding et al. |
| 6,364,904 B1 | 4/2002 | Smith |
| 6,368,346 B1 | 4/2002 | Jadhav |
| 6,368,347 B1 | 4/2002 | Maini et al. |
| 6,368,355 B1 | 4/2002 | Uflacker |
| 6,371,979 B1 | 4/2002 | Beyar et al. |
| 6,372,136 B1 | 4/2002 | Nakatsuka |
| 6,375,787 B1 | 4/2002 | Lukic |
| 6,379,381 B1 | 4/2002 | Hossainy et al. |
| 6,379,382 B1 | 4/2002 | Yang |
| 6,379,392 B1 | 4/2002 | Walak |
| 6,383,213 B2 | 5/2002 | Wilson et al. |
| 6,383,214 B1 | 5/2002 | Banas et al. |
| 6,387,119 B2 | 5/2002 | Wolf et al. |
| 6,387,124 B1 | 5/2002 | Buscemi et al. |
| 6,391,050 B1 | 5/2002 | Broome |
| 6,391,052 B2 | 5/2002 | Buirge et al. |
| 6,395,018 B1 | 5/2002 | Castaneda |
| 6,395,019 B2 | 5/2002 | Chobotov |

(56) References Cited

U.S. PATENT DOCUMENTS

| | | |
|---|---|---|
| 6,395,022 B1 | 5/2002 | Piplani et al. |
| 6,395,208 B1 | 5/2002 | Herweck et al. |
| 6,398,803 B1 | 6/2002 | Layne et al. |
| 6,402,779 B1 | 6/2002 | Colone et al. |
| 6,406,489 B1 | 6/2002 | Richter et al. |
| 6,409,749 B1 | 6/2002 | Maynard |
| 6,409,750 B1 | 6/2002 | Hyodoh |
| 6,409,754 B1 | 6/2002 | Smith et al. |
| 6,409,756 B1 | 6/2002 | Murphy |
| 6,409,757 B1 | 6/2002 | Trout et al. |
| 6,409,761 B1 | 6/2002 | Jang |
| 6,413,269 B1 | 7/2002 | Bui et al. |
| 6,416,535 B1 | 7/2002 | Lazarus |
| 6,416,536 B1 | 7/2002 | Yee |
| 6,416,537 B1 | 7/2002 | Martakos et al. |
| 6,416,538 B1 | 7/2002 | Ley et al. |
| 6,416,539 B1 | 7/2002 | Hassdenteufel |
| 6,416,542 B1 | 7/2002 | Marcade et al. |
| 6,419,701 B1 | 7/2002 | Cook et al. |
| 6,423,084 B1 | 7/2002 | St. Germain |
| 6,423,089 B1 | 7/2002 | Gingras et al. |
| 6,423,090 B1 | 7/2002 | Hancock |
| 6,425,855 B2 | 7/2002 | Tomonto |
| 6,425,898 B1 | 7/2002 | Wilson et al. |
| 6,428,506 B1 | 8/2002 | Simhambhatla et al. |
| 6,428,565 B1 | 8/2002 | Wisselink |
| 6,428,566 B1 | 8/2002 | Holt |
| 6,428,567 B2 | 8/2002 | Wilson et al. |
| 6,428,569 B1 | 8/2002 | Brown |
| 6,428,570 B1 | 8/2002 | Globerman |
| 6,428,571 B1 | 8/2002 | Lentz et al. |
| 6,432,129 B2 | 8/2002 | DiCaprio |
| 6,432,131 B1 | 8/2002 | Ravenscroft |
| 6,432,132 B1 | 8/2002 | Cottone et al. |
| 6,436,104 B2 | 8/2002 | Hoieibane |
| 6,436,133 B1 | 8/2002 | Furst et al. |
| 6,436,134 B2 | 8/2002 | Richter et al. |
| 6,436,135 B1 | 8/2002 | Goldfarb |
| 6,440,165 B1 | 8/2002 | Richter et al. |
| 6,443,941 B1 | 9/2002 | Slepian et al. |
| 6,443,979 B1 | 9/2002 | Stalker et al. |
| 6,443,981 B1 | 9/2002 | Colone et al. |
| 6,447,501 B1 | 9/2002 | Solar et al. |
| 6,447,522 B2 | 9/2002 | Gambale et al. |
| 6,451,047 B2 | 9/2002 | McCrea et al. |
| 6,451,050 B1 | 9/2002 | Rudakov et al. |
| 6,451,051 B2 | 9/2002 | Drasler et al. |
| 6,451,053 B1 | 9/2002 | Dehdashtian et al. |
| 6,454,796 B1 | 9/2002 | Barkman et al. |
| 6,461,381 B2 | 10/2002 | Israel et al. |
| 6,463,317 B1 | 10/2002 | Kucharczyk et al. |
| 6,464,720 B2 | 10/2002 | Boatman et al. |
| 6,464,721 B1 | 10/2002 | Marcade et al. |
| 6,464,722 B2 | 10/2002 | Israel et al. |
| 6,471,718 B1 | 10/2002 | Staehle et al. |
| 6,471,720 B1 | 10/2002 | Ehr et al. |
| 6,471,721 B1 | 10/2002 | Dang |
| 6,471,722 B1 | 10/2002 | Inoue |
| 6,475,166 B1 | 11/2002 | Escano |
| 6,475,208 B2 | 11/2002 | Mauch |
| 6,475,236 B1 | 11/2002 | Roubin et al. |
| 6,475,237 B2 | 11/2002 | Drasler |
| 6,475,238 B1 | 11/2002 | Fedida |
| 6,475,466 B1 | 11/2002 | Ricci et al. |
| 6,478,807 B1 | 11/2002 | Foreman et al. |
| 6,478,815 B1 | 11/2002 | Alt |
| 6,478,816 B1 | 11/2002 | Kveen et al. |
| 6,482,227 B1 | 11/2002 | Solovay |
| 6,485,507 B1 | 11/2002 | Walak et al. |
| 6,485,508 B1 | 11/2002 | McGuinness |
| 6,485,509 B2 | 11/2002 | Killion et al. |
| 6,485,511 B2 | 11/2002 | Lau et al. |
| 6,485,513 B1 | 11/2002 | Fan |
| 6,485,515 B2 | 11/2002 | Strecker |
| 6,485,524 B2 | 11/2002 | Strecker |
| 6,488,694 B1 | 12/2002 | Lau et al. |
| 6,488,700 B2 | 12/2002 | Klumb et al. |
| 6,488,701 B1 | 12/2002 | Nolting et al. |
| 6,488,705 B2 | 12/2002 | Schmitt et al. |
| 6,491,718 B1 | 12/2002 | Ahmad |
| 6,491,719 B1 | 12/2002 | Fogary et al. |
| 6,494,875 B1 | 12/2002 | Mauch |
| 6,494,904 B1 | 12/2002 | Love |
| 6,494,907 B1 | 12/2002 | Bulver |
| 6,494,909 B2 | 12/2002 | Greenhalgh |
| 6,497,722 B1 | 12/2002 | Von Oepen et al. |
| 6,497,723 B1 | 12/2002 | Starck et al. |
| 6,500,202 B1 | 12/2002 | Shaolian et al. |
| 6,500,203 B1 | 12/2002 | Thompson et al. |
| 6,500,204 B1 | 12/2002 | Igaki |
| 6,500,532 B1 | 12/2002 | Ruefer et al. |
| 6,503,271 B2 | 1/2003 | Duerig et al. |
| 6,506,211 B1 | 1/2003 | Doran et al. |
| 6,508,833 B2 | 1/2003 | Pavcnik et al. |
| 6,508,834 B1 | 1/2003 | Pinchasik et al. |
| 6,514,281 B1 | 2/2003 | Blaeser et al. |
| 6,517,558 B2 | 2/2003 | Gittings et al. |
| 6,517,571 B1 | 2/2003 | Brauker et al. |
| 6,517,573 B1 | 2/2003 | Pollock et al. |
| 6,517,574 B1 | 2/2003 | Chuter |
| 6,520,983 B1 | 2/2003 | Colgan et al. |
| 6,520,984 B1 | 2/2003 | Garrison et al. |
| 6,520,986 B2 | 2/2003 | Martin et al. |
| 6,524,334 B1 | 2/2003 | Thompson |
| 6,524,335 B1 | 2/2003 | Hartley et al. |
| 6,524,336 B1 | 2/2003 | Papazolgou et al. |
| 6,530,765 B1 | 3/2003 | Zdrahala et al. |
| 6,530,947 B1 | 3/2003 | Euteneuer et al. |
| 6,530,950 B1 | 3/2003 | Alvarado et al. |
| 6,533,806 B1 | 3/2003 | Sullivan et al. |
| 6,533,807 B2 | 3/2003 | Wolinsky et al. |
| 6,533,808 B1 | 3/2003 | Thompson et al. |
| 6,533,811 B1 | 3/2003 | Ryan et al. |
| 6,537,202 B1 | 3/2003 | Frantzen |
| 6,540,778 B1 | 4/2003 | Quiachon et al. |
| 6,540,780 B1 | 4/2003 | Zilla et al. |
| 6,547,813 B2 | 4/2003 | Stiger et al. |
| 6,547,814 B2 | 4/2003 | Edwin et al. |
| 6,547,815 B2 | 4/2003 | Myers |
| 6,547,817 B1 | 4/2003 | Fischell et al. |
| 6,548,013 B2 | 4/2003 | Kadavy et al. |
| 6,551,350 B1 | 4/2003 | Thornton et al. |
| 6,554,857 B1 | 4/2003 | Zilla et al. |
| 6,554,858 B2 | 4/2003 | Dereume et al. |
| 6,558,414 B2 | 5/2003 | Layne |
| 6,558,415 B2 | 5/2003 | Thompson |
| 6,562,063 B1 | 5/2003 | Euteneuer et al. |
| 6,565,597 B1 | 5/2003 | Fearnot |
| 6,569,150 B2 | 5/2003 | Teague |
| 6,569,190 B2 | 5/2003 | Whalen, II et al. |
| 6,569,193 B1 | 5/2003 | Cox et al. |
| 6,572,649 B2 | 6/2003 | Berry et al. |
| 6,575,994 B1 | 6/2003 | Marin |
| 6,576,009 B2 | 6/2003 | Ryan et al. |
| 6,579,314 B1 | 6/2003 | Lombardi et al. |
| 6,582,458 B1 | 6/2003 | White et al. |
| 6,589,274 B2 | 7/2003 | Stiger et al. |
| 6,589,275 B1 | 7/2003 | Ivancev et al. |
| 6,592,614 B2 | 7/2003 | Lenker et al. |
| 6,592,615 B1 | 7/2003 | Marcade |
| 6,602,269 B2 | 8/2003 | Wallace et al. |
| 6,602,280 B2 | 8/2003 | Chobotov |
| 6,602,283 B2 | 8/2003 | Doran et al. |
| 6,605,110 B2 | 8/2003 | Harrison |
| 6,607,551 B1 | 8/2003 | Sullivan et al. |
| 6,613,082 B2 | 9/2003 | Yang |
| 6,613,083 B2 | 9/2003 | Alt |
| 6,613,084 B2 | 9/2003 | Yang |
| 6,620,190 B1 | 9/2003 | Colone |
| 6,626,938 B1 | 9/2003 | Butaric et al. |
| 6,635,079 B2 | 10/2003 | Unsworth et al. |
| 6,641,606 B2 | 11/2003 | Ouriel |
| 6,645,240 B2 | 11/2003 | Yee |
| 6,652,554 B1 | 11/2003 | Wholey et al. |

(56) References Cited

U.S. PATENT DOCUMENTS

| | | |
|---|---|---|
| 6,652,570 B2 | 11/2003 | Smith et al. |
| 6,652,573 B2 | 11/2003 | Oepen |
| 6,652,575 B2 | 11/2003 | Wang |
| 6,652,580 B1 | 11/2003 | Chuter |
| 6,656,215 B1 | 12/2003 | Yanez et al. |
| 6,656,506 B1 | 12/2003 | Wu et al. |
| 6,660,030 B2 | 12/2003 | Shaolian et al. |
| 6,663,662 B2 | 12/2003 | Pacetti et al. |
| 6,663,663 B2 | 12/2003 | Kim et al. |
| 6,663,664 B1 | 12/2003 | Pacitti |
| 6,663,665 B2 | 12/2003 | Shaolian et al. |
| 6,663,667 B2 | 12/2003 | Dehdashtian et al. |
| 6,669,718 B2 | 12/2003 | Besselink |
| 6,669,720 B1 | 12/2003 | Pierce |
| 6,669,723 B2 | 12/2003 | Killion et al. |
| 6,669,724 B2 | 12/2003 | Park et al. |
| 6,673,102 B2 | 1/2004 | Vonesh et al. |
| 6,673,103 B1 | 1/2004 | Golds et al. |
| 6,673,106 B2 | 1/2004 | Mitelberg et al. |
| 6,673,107 B1 | 1/2004 | Brandt et al. |
| 6,676,667 B2 | 1/2004 | Mareiro et al. |
| 6,676,694 B1 | 1/2004 | Weiss |
| 6,676,695 B2 | 1/2004 | Solem |
| 6,679,911 B2 | 1/2004 | Burgermeister |
| 6,685,736 B1 | 2/2004 | White et al. |
| 6,689,142 B1 | 2/2004 | Tremaglio, Jr. |
| 6,689,158 B1 | 2/2004 | White et al. |
| 6,689,159 B2 | 2/2004 | Hartigan et al. |
| 6,692,523 B2 | 2/2004 | Holman et al. |
| 6,694,983 B2 | 2/2004 | Wolf et al. |
| 6,695,833 B1 | 2/2004 | Frantzen |
| 6,695,875 B2 | 2/2004 | Stelter et al. |
| 6,695,877 B2 | 2/2004 | Brucker et al. |
| 6,696,666 B2 | 2/2004 | Merdan et al. |
| 6,699,274 B2 | 3/2004 | Stinson |
| 6,699,277 B1 | 3/2004 | Freidberg et al. |
| 6,702,847 B2 | 3/2004 | DiCarlo |
| 6,702,849 B1 | 3/2004 | Dutta et al. |
| 6,706,064 B1 | 3/2004 | Anson |
| 6,709,449 B2 | 3/2004 | Camrud et al. |
| 6,709,455 B1 | 3/2004 | Chouinard |
| 6,712,827 B2 | 3/2004 | Ellis et al. |
| 6,716,238 B2 | 4/2004 | Elliott |
| 6,716,239 B2 | 4/2004 | Sowinski |
| 6,719,783 B2 | 4/2004 | Lentz et al. |
| 6,726,712 B1 | 4/2004 | Raeder-Devens |
| 6,730,119 B1 | 5/2004 | Smalling |
| 6,733,521 B2 | 5/2004 | Chobotov et al. |
| 6,736,839 B2 | 5/2004 | Cummings |
| 6,740,111 B1 | 5/2004 | Lauterjung |
| 6,740,114 B2 | 5/2004 | Burgermeister |
| 6,740,115 B2 | 5/2004 | Lombardi |
| 6,743,210 B2 | 6/2004 | Hart et al. |
| 6,743,511 B2 | 6/2004 | Dittrich et al. |
| 6,746,890 B2 | 6/2004 | Gupta |
| 6,752,829 B2 | 6/2004 | Kocur et al. |
| 6,755,855 B2 | 6/2004 | Yurek et al. |
| 6,758,858 B2 | 7/2004 | McCrea et al. |
| 6,761,733 B2 | 7/2004 | Chobotov et al. |
| 6,770,086 B1 | 8/2004 | Girton et al. |
| 6,770,087 B2 | 8/2004 | Layne et al. |
| 6,773,453 B2 | 8/2004 | Ravenscroft |
| 6,773,457 B2 | 8/2004 | Ivancev et al. |
| 6,776,604 B1 | 8/2004 | Chobotov et al. |
| 6,776,793 B2 | 8/2004 | Brown et al. |
| 6,786,920 B2 | 9/2004 | Shannon et al. |
| 6,790,227 B2 | 9/2004 | Burgermeister |
| 6,790,230 B2 | 9/2004 | Beyersdorf et al. |
| 6,793,672 B2 | 9/2004 | Khosravi et al. |
| 6,796,999 B2 | 9/2004 | Pinchasik |
| 6,802,849 B2 | 10/2004 | Blaeser et al. |
| 6,802,856 B2 | 10/2004 | Wilson |
| 6,808,534 B1 | 10/2004 | Escano |
| 6,814,753 B2 | 11/2004 | Schmitt |
| 6,818,013 B2 | 11/2004 | Mitelberg et al. |
| 6,821,292 B2 | 11/2004 | Pazienza et al. |
| 6,824,558 B2 | 11/2004 | Parodi |
| 6,827,726 B2 | 12/2004 | Parodi |
| 6,827,731 B2 | 12/2004 | Armstrong et al. |
| 6,827,735 B2 | 12/2004 | Greenberg |
| 6,827,737 B2 | 12/2004 | Hill et al. |
| 6,833,004 B2 | 12/2004 | Ishil et al. |
| 6,841,213 B2 | 1/2005 | Parsonage et al. |
| 6,843,802 B1 | 1/2005 | Villalobos et al. |
| 6,849,086 B2 | 2/2005 | Cragg |
| 6,858,035 B2 | 2/2005 | Whayne |
| 6,860,900 B2 | 3/2005 | Clerc et al. |
| 6,863,685 B2 | 3/2005 | Davila et al. |
| 6,869,443 B2 | 3/2005 | Buscemi et al. |
| 6,878,160 B2 | 4/2005 | Gilligan et al. |
| 6,878,161 B2 | 4/2005 | Lenker |
| 6,884,260 B2 | 4/2005 | Kugler et al. |
| 6,899,728 B1 | 5/2005 | Phillips et al. |
| 6,918,925 B2 | 7/2005 | Tehrani |
| 6,918,927 B2 | 7/2005 | Bates et al. |
| 6,923,827 B2 | 8/2005 | Campbell et al. |
| 6,926,732 B2 | 8/2005 | Derus et al. |
| 6,929,659 B2 | 8/2005 | Pinchuk |
| 6,929,709 B2 | 8/2005 | Smith |
| 6,939,370 B2 | 9/2005 | Hartley et al. |
| 6,939,374 B2 | 9/2005 | Banik et al. |
| 6,942,689 B2 | 9/2005 | Majercak |
| 6,945,989 B1 | 9/2005 | Betelia et al. |
| 6,945,992 B2 | 9/2005 | Goodson et al. |
| 6,949,120 B2 | 9/2005 | Kveen et al. |
| 6,962,602 B2 | 11/2005 | Vardi et al. |
| 6,962,603 B1 | 11/2005 | Brown |
| 6,964,677 B2 | 11/2005 | Osypka |
| 6,974,471 B2 | 12/2005 | Van Schie et al. |
| 6,974,472 B2 | 12/2005 | Hong et al. |
| 6,981,982 B2 | 1/2006 | Armstrong et al. |
| 6,984,244 B2 | 1/2006 | Perez et al. |
| 6,989,026 B2 | 1/2006 | Richter et al. |
| 6,994,722 B2 | 2/2006 | DiCarlo |
| 6,997,945 B2 | 2/2006 | Germain |
| 6,998,060 B2 | 2/2006 | Tomonto |
| 7,001,407 B2 | 2/2006 | Hansen et al. |
| 7,001,419 B2 | 2/2006 | DiCaprio et al. |
| 7,001,431 B2 | 2/2006 | Bao et al. |
| 7,011,673 B2 | 3/2006 | Fischell et al. |
| 7,011,674 B2 | 3/2006 | Brenneman |
| 7,014,653 B2 | 3/2006 | Ouriel |
| 7,022,132 B2 | 4/2006 | Kocur |
| 7,022,135 B2 | 4/2006 | Zilla et al. |
| 7,033,389 B2 | 4/2006 | Sherry |
| 7,056,325 B1 | 6/2006 | Makower |
| 7,056,336 B2 | 6/2006 | Armstrong et al. |
| 7,056,412 B2 | 6/2006 | Henderson |
| 7,066,951 B2 | 6/2006 | Chobotov |
| 7,073,504 B2 | 7/2006 | Callister et al. |
| 7,081,129 B2 | 7/2006 | Chobotov |
| 7,081,132 B2 | 7/2006 | Cook |
| 7,083,642 B2 | 8/2006 | Sirhan et al. |
| 7,090,693 B1 | 8/2006 | Chobotov et al. |
| 7,094,255 B2 | 8/2006 | Penn et al. |
| 7,108,715 B2 | 9/2006 | Lawrence-Brown et al. |
| 7,115,140 B2 | 10/2006 | Stoltze et al. |
| 7,125,464 B2 | 10/2006 | Chobotov et al. |
| 7,128,754 B2 | 10/2006 | Bolduc |
| 7,128,755 B2 | 10/2006 | Su et al. |
| 7,147,455 B2 | 12/2006 | Chobotov et al. |
| 7,147,660 B2 | 12/2006 | Chobotov et al. |
| 7,147,661 B2 * | 12/2006 | Chobotov et al. ............ 623/1.16 |
| 7,150,758 B2 | 12/2006 | Kari et al. |
| 7,160,318 B2 | 1/2007 | Greenberg et al. |
| 7,166,125 B1 | 1/2007 | Baker et al. |
| 7,175,651 B2 | 2/2007 | Kerr |
| 7,175,652 B2 | 2/2007 | Cook et al. |
| 7,189,256 B2 | 3/2007 | Smith |
| 7,192,441 B2 | 3/2007 | Sherry |
| 7,223,280 B2 | 5/2007 | Anson et al. |
| 7,226,474 B2 | 6/2007 | Iancea et al. |
| 7,229,470 B2 | 6/2007 | Brown et al. |
| 7,232,459 B2 | 6/2007 | Greenberg |

(56) References Cited

U.S. PATENT DOCUMENTS

| | | |
|---|---|---|
| 7,235,083 B1 | 6/2007 | Perez et al. |
| 7,235,095 B2 | 6/2007 | Haverkost et al. |
| 7,243,408 B2 | 7/2007 | Vietmeier |
| 7,244,242 B2 | 7/2007 | Freyman |
| 7,255,711 B2 | 8/2007 | Holman et al. |
| 7,273,494 B2 | 9/2007 | Rolando et al. |
| 7,284,399 B1 | 10/2007 | Sisco |
| 7,294,147 B2 | 11/2007 | Hartley |
| 7,314,484 B2 | 1/2008 | Deem et al. |
| 7,318,835 B2 | 1/2008 | Berra |
| 7,338,518 B2 | 3/2008 | Chobotov |
| 7,351,256 B2 | 4/2008 | Hojeibane et al. |
| 7,425,219 B2 | 9/2008 | Quadri |
| 7,435,253 B1 | 10/2008 | Hartley et al. |
| 7,452,374 B2 | 11/2008 | Hain et al. |
| 7,465,270 B2 | 12/2008 | Li |
| 7,476,245 B2 | 1/2009 | Abbate |
| 7,485,138 B2 | 2/2009 | Fearnot et al. |
| 7,491,230 B2 | 2/2009 | Holman et al. |
| 7,491,234 B2 | 2/2009 | Palasis et al. |
| 7,500,988 B1 | 3/2009 | Butaric et al. |
| 7,510,571 B2 | 3/2009 | Spiridigliozzi et al. |
| 7,520,890 B2 | 4/2009 | Phillips |
| 7,520,895 B2 | 4/2009 | Douglas et al. |
| 7,530,988 B2 | 5/2009 | Evans et al. |
| 7,550,004 B2 | 6/2009 | Bahler et al. |
| 7,550,005 B2 | 6/2009 | Bates et al. |
| 7,556,645 B2 | 7/2009 | Lashinski et al. |
| 7,591,843 B1 | 9/2009 | Escano |
| 7,597,710 B2 | 10/2009 | Obermiller |
| 7,722,663 B1 | 5/2010 | Austin |
| 7,766,954 B2 | 8/2010 | Chobotov et al. |
| 7,976,575 B2 | 7/2011 | Hartley |
| 8,043,356 B2 | 10/2011 | Kolbel et al. |
| 8,066,755 B2 | 11/2011 | Zacharias et al. |
| 8,118,862 B2 | 2/2012 | Saeed |
| 8,128,680 B2 | 3/2012 | Arnault De La Menardiere et al. |
| 8,206,427 B1 | 6/2012 | Ryan et al. |
| 8,252,036 B2 | 8/2012 | Cartledge et al. |
| 2001/0014794 A1 | 8/2001 | Moll |
| 2001/0016748 A1 | 8/2001 | Tanner et al. |
| 2001/0023369 A1 | 9/2001 | Chobotov |
| 2001/0027339 A1 | 10/2001 | Boatman |
| 2001/0029349 A1 | 10/2001 | Leschinsky |
| 2001/0037142 A1 | 11/2001 | Stelter et al. |
| 2001/0039445 A1 | 11/2001 | Hall et al. |
| 2001/0041928 A1 | 11/2001 | Pavcnik et al. |
| 2001/0044652 A1 | 11/2001 | Moore |
| 2001/0047150 A1 | 11/2001 | Chobotov |
| 2001/0049509 A1 | 12/2001 | Sekine et al. |
| 2001/0049534 A1 | 12/2001 | Lachat |
| 2002/0007193 A1 | 1/2002 | Tanner et al. |
| 2002/0011684 A1 | 1/2002 | Bahar et al. |
| 2002/0016626 A1 | 2/2002 | DiMatteo et al. |
| 2002/0019659 A1 | 2/2002 | Goicoechea et al. |
| 2002/0026214 A1 | 2/2002 | Tanner et al. |
| 2002/0029051 A1 | 3/2002 | Callister et al. |
| 2002/0032408 A1 | 3/2002 | Parker et al. |
| 2002/0035395 A1 | 3/2002 | Sugimoto |
| 2002/0040236 A1 | 4/2002 | Lau et al. |
| 2002/0040237 A1 | 4/2002 | Lentz et al. |
| 2002/0042644 A1 | 4/2002 | Greenhalgh |
| 2002/0045931 A1 | 4/2002 | Sogard et al. |
| 2002/0045933 A1 | 4/2002 | Jang |
| 2002/0045934 A1 | 4/2002 | Jang |
| 2002/0045935 A1 | 4/2002 | Jang |
| 2002/0049487 A1 | 4/2002 | Lootz et al. |
| 2002/0049490 A1 | 4/2002 | Pollock et al. |
| 2002/0049493 A1 | 4/2002 | Jang |
| 2002/0052627 A1 | 5/2002 | Boylan et al. |
| 2002/0052644 A1 | 5/2002 | Shaolian et al. |
| 2002/0052649 A1 | 5/2002 | Greenhalgh |
| 2002/0055768 A1 | 5/2002 | Hess et al. |
| 2002/0065552 A1 | 5/2002 | Jayaraman et al. |
| 2002/0072792 A1 | 6/2002 | Burgermeister et al. |
| 2002/0072793 A1 | 6/2002 | Rolando et al. |
| 2002/0076542 A1 | 6/2002 | Kramer et al. |
| 2002/0077692 A1 | 6/2002 | Besselink |
| 2002/0082680 A1 | 6/2002 | Shanley et al. |
| 2002/0082682 A1 | 6/2002 | Barclay et al. |
| 2002/0082685 A1 | 6/2002 | Sirhan et al. |
| 2002/0095208 A1 | 7/2002 | Gregorich et al. |
| 2002/0096252 A1 | 7/2002 | Lukic |
| 2002/0107561 A1 | 8/2002 | Pinheiro |
| 2002/0116048 A1 | 8/2002 | Chobotov |
| 2002/0116050 A1 | 8/2002 | Kocur |
| 2002/0120321 A1 | 8/2002 | Gunderson et al. |
| 2002/0120327 A1 | 8/2002 | Cox et al. |
| 2002/0123790 A1 | 9/2002 | White et al. |
| 2002/0123791 A1 | 9/2002 | Harrison |
| 2002/0123796 A1 | 9/2002 | Majercak et al. |
| 2002/0143387 A1 | 10/2002 | Soetikno et al. |
| 2002/0147492 A1 | 10/2002 | Shokoohi et al. |
| 2002/0151953 A1 | 10/2002 | Chobotov et al. |
| 2002/0151956 A1 | 10/2002 | Chobotov et al. |
| 2002/0156521 A1 | 10/2002 | Ryan et al. |
| 2002/0156522 A1 | 10/2002 | Ivancev et al. |
| 2002/0161376 A1 | 10/2002 | Barry et al. |
| 2002/0165603 A1 | 11/2002 | Thornton et al. |
| 2002/0169497 A1 | 11/2002 | Wholey et al. |
| 2002/0183826 A1 | 12/2002 | Dorn et al. |
| 2002/0183827 A1 | 12/2002 | Derus et al. |
| 2002/0188344 A1 | 12/2002 | Bolea et al. |
| 2002/0188346 A1 | 12/2002 | Healy et al. |
| 2002/0188347 A1 | 12/2002 | Mathis |
| 2002/0193867 A1 | 12/2002 | Gladdish, Jr. et al. |
| 2002/0193872 A1 | 12/2002 | Trout et al. |
| 2002/0193873 A1 | 12/2002 | Brucker et al. |
| 2002/0198585 A1 | 12/2002 | Wisselink |
| 2002/0198587 A1 | 12/2002 | Greenberg et al. |
| 2003/0004560 A1 | 1/2003 | Chobotov et al. |
| 2003/0004565 A1 | 1/2003 | Harnek et al. |
| 2003/0009212 A1 | 1/2003 | Kerr |
| 2003/0014075 A1 | 1/2003 | Rosenbluth et al. |
| 2003/0040803 A1 | 2/2003 | Rioux et al. |
| 2003/0050684 A1 | 3/2003 | Abrams et al. |
| 2003/0068296 A1 | 4/2003 | Ricci et al. |
| 2003/0074050 A1 | 4/2003 | Kerr |
| 2003/0083736 A1 | 5/2003 | Brown et al. |
| 2003/0088305 A1 | 5/2003 | Van Schie et al. |
| 2003/0097170 A1 | 5/2003 | Friedrich et al. |
| 2003/0116260 A1 | 6/2003 | Chobotov et al. |
| 2003/0120263 A1 | 6/2003 | Ouriel et al. |
| 2003/0120331 A1 | 6/2003 | Chobotov et al. |
| 2003/0125797 A1 | 7/2003 | Chobotov |
| 2003/0135256 A1 | 7/2003 | Gallagher et al. |
| 2003/0135261 A1 | 7/2003 | Kugler et al. |
| 2003/0176912 A1 | 9/2003 | Chuter et al. |
| 2003/0191518 A1 | 10/2003 | Spiridigliozzi et al. |
| 2003/0204236 A1 | 10/2003 | Letort |
| 2003/0204244 A1 | 10/2003 | Stiger |
| 2003/0212449 A1 | 11/2003 | Cox |
| 2003/0220683 A1 | 11/2003 | Minasian |
| 2003/0225453 A1 | 12/2003 | Murch |
| 2003/0233068 A1 | 12/2003 | Jayaraman |
| 2004/0002714 A1 | 1/2004 | Weiss |
| 2004/0024446 A1 | 2/2004 | Smith |
| 2004/0034407 A1 | 2/2004 | Sherry |
| 2004/0044358 A1 | 3/2004 | Khosravi et al. |
| 2004/0044395 A1 | 3/2004 | Nelson |
| 2004/0049212 A1 | 3/2004 | Whayne |
| 2004/0049264 A1 | 3/2004 | Sowinski et al. |
| 2004/0093055 A1 | 5/2004 | Bartorelli et al. |
| 2004/0093064 A1 | 5/2004 | Bosma |
| 2004/0093068 A1 | 5/2004 | Bergen et al. |
| 2004/0093078 A1 | 5/2004 | Moll et al. |
| 2004/0098096 A1 | 5/2004 | Eton |
| 2004/0106974 A1 | 6/2004 | Greenberg et al. |
| 2004/0116997 A1 | 6/2004 | Taylor et al. |
| 2004/0138734 A1 | 7/2004 | Chobotov et al. |
| 2004/0148008 A1 | 7/2004 | Goodson et al. |
| 2004/0162607 A1 | 8/2004 | Masroor |
| 2004/0167614 A1 | 8/2004 | Anson |
| 2004/0167619 A1 | 8/2004 | Case |

(56) References Cited

U.S. PATENT DOCUMENTS

| | | |
|---|---|---|
| 2004/0176836 A1 | 9/2004 | Kari et al. |
| 2004/0193252 A1 | 9/2004 | Perez et al. |
| 2004/0210304 A1 | 10/2004 | Seguin et al. |
| 2004/0215213 A1 | 10/2004 | Dolan |
| 2004/0220655 A1 | 11/2004 | Swanson et al. |
| 2004/0220664 A1 | 11/2004 | Chobotov |
| 2004/0254625 A1 | 12/2004 | Stephens |
| 2005/0004660 A1 | 1/2005 | Rosenbluth et al. |
| 2005/0033406 A1 | 2/2005 | Barnhart et al. |
| 2005/0043785 A1 | 2/2005 | Tanner et al. |
| 2005/0049674 A1 | 3/2005 | Berra et al. |
| 2005/0049691 A1 | 3/2005 | Mercile et al. |
| 2005/0075715 A1 | 4/2005 | Borges et al. |
| 2005/0090804 A1 | 4/2005 | Chobotov et al. |
| 2005/0090901 A1 | 4/2005 | Studer |
| 2005/0154443 A1 | 7/2005 | Linder et al. |
| 2005/0158272 A1 | 7/2005 | Whirley et al. |
| 2005/0171593 A1 | 8/2005 | Whirley et al. |
| 2005/0177222 A1 | 8/2005 | Mead |
| 2005/0222669 A1 | 10/2005 | Purdy |
| 2005/0228484 A1 | 10/2005 | Stephens et al. |
| 2006/0009833 A1 | 1/2006 | Chobotov et al. |
| 2006/0020319 A1 | 1/2006 | Kim |
| 2006/0020320 A1 | 1/2006 | Shaolian et al. |
| 2006/0030921 A1 | 2/2006 | Chu |
| 2006/0079952 A1 | 4/2006 | Kaplan et al. |
| 2006/0136047 A1 | 6/2006 | Obermiller et al. |
| 2006/0149364 A1 | 7/2006 | Walak et al. |
| 2006/0155358 A1 | 7/2006 | LaDuca et al. |
| 2006/0155363 A1 | 7/2006 | LaDuca et al. |
| 2006/0161244 A1 | 7/2006 | Seguin |
| 2006/0178732 A1 | 8/2006 | Chobotov et al. |
| 2006/0186143 A1 | 8/2006 | Argentine |
| 2006/0212112 A1 | 9/2006 | Evans et al. |
| 2006/0224232 A1 | 10/2006 | Chobotov |
| 2006/0233990 A1 | 10/2006 | Humphrey et al. |
| 2006/0233991 A1 | 10/2006 | Humphrey et al. |
| 2006/0287713 A1 | 12/2006 | Douglas et al. |
| 2006/0292206 A1 | 12/2006 | Kim et al. |
| 2007/0012396 A1 | 1/2007 | Chobotov et al. |
| 2007/0016281 A1 | 1/2007 | Melsheimer |
| 2007/0055347 A1 | 3/2007 | Arbefeuille |
| 2007/0078506 A1 | 4/2007 | McCormick et al. |
| 2007/0100427 A1 | 5/2007 | Perouse |
| 2007/0112413 A1 | 5/2007 | Smith |
| 2007/0162106 A1 | 7/2007 | Evans et al. |
| 2007/0167901 A1 | 7/2007 | Herrig et al. |
| 2007/0172526 A1 | 7/2007 | Galdonik |
| 2007/0203571 A1 | 8/2007 | Kaplan et al. |
| 2007/0219627 A1 | 9/2007 | Chu et al. |
| 2007/0239273 A1 | 10/2007 | Allen |
| 2007/0244539 A1 | 10/2007 | Lentz et al. |
| 2007/0276477 A1 | 11/2007 | Lee et al. |
| 2007/0282369 A1 | 12/2007 | Gilson et al. |
| 2008/0015687 A1 | 1/2008 | Lashinski et al. |
| 2008/0027529 A1 | 1/2008 | Hartley et al. |
| 2008/0051705 A1 | 2/2008 | Von Oepen et al. |
| 2008/0058920 A1 | 3/2008 | Kari |
| 2008/0114441 A1 | 5/2008 | Rust |
| 2008/0114442 A1 | 5/2008 | Mitchell et al. |
| 2008/0114443 A1 | 5/2008 | Mitchell |
| 2008/0172119 A1 | 7/2008 | Yamasaki et al. |
| 2008/0208240 A1* | 8/2008 | Paz ............................... 606/191 |
| 2008/0208309 A1 | 8/2008 | Saeed |
| 2008/0228255 A1 | 9/2008 | Rust |
| 2008/0234800 A1 | 9/2008 | Clarke et al. |
| 2008/0288045 A1 | 11/2008 | Saeed |
| 2009/0036971 A1 | 2/2009 | Humphrey et al. |
| 2009/0042796 A1 | 2/2009 | Wallach et al. |
| 2009/0082841 A1 | 3/2009 | Zacharias et al. |
| 2009/0082842 A1 | 3/2009 | Glynn |
| 2009/0082844 A1 | 3/2009 | Chobotov et al. |
| 2009/0082845 A1 | 3/2009 | Chobotov et al. |
| 2009/0082846 A1 | 3/2009 | Chobotov et al. |
| 2009/0082847 A1 | 3/2009 | Zacharias et al. |
| 2009/0099649 A1 | 4/2009 | Chobotov et al. |
| 2009/0125098 A1 | 5/2009 | Chuter |
| 2009/0132020 A1 | 5/2009 | Watson |
| 2009/0132026 A1 | 5/2009 | Martin et al. |
| 2009/0171431 A1 | 7/2009 | Swanson et al. |
| 2009/0182405 A1 | 7/2009 | Arnault de la Menardiere et al. |
| 2009/0182406 A1 | 7/2009 | Eidenschink |
| 2009/0198267 A1 | 8/2009 | Evans et al. |
| 2009/0259296 A1 | 10/2009 | Mciff et al. |
| 2009/0287145 A1 | 11/2009 | Cragg et al. |
| 2009/0287290 A1 | 11/2009 | Macaulay et al. |
| 2010/0114290 A1 | 5/2010 | Rassmussen et al. |
| 2010/0161028 A1 | 6/2010 | Chuter et al. |
| 2010/0211052 A1 | 8/2010 | Brown et al. |
| 2010/0249908 A1 | 9/2010 | Chau et al. |
| 2010/0305686 A1 | 12/2010 | Cragg |
| 2010/0331958 A1 | 12/2010 | Chobotov et al. |
| 2011/0130819 A1 | 6/2011 | Cragg |
| 2011/0130820 A1 | 6/2011 | Cragg |
| 2011/0130824 A1 | 6/2011 | Cragg |
| 2011/0130825 A1 | 6/2011 | Cragg |
| 2011/0130826 A1 | 6/2011 | Cragg |
| 2011/0218609 A1 | 9/2011 | Chobotov et al. |
| 2011/0257673 A1 | 10/2011 | Heraty |
| 2012/0016457 A1 | 1/2012 | Chobotov et al. |
| 2012/0041543 A1 | 2/2012 | Huang et al. |
| 2012/0130469 A1 | 5/2012 | Cragg |
| 2012/0191174 A1 | 7/2012 | Vinluan et al. |
| 2013/0268057 A1 | 10/2013 | Vinluan et al. |
| 2013/0338753 A1 | 12/2013 | Geusen |
| 2014/0222132 A1 | 8/2014 | Boucher et al. |

FOREIGN PATENT DOCUMENTS

| | | |
|---|---|---|
| EP | 0621016 | 10/1994 |
| EP | 0646365 | 4/1995 |
| EP | 0714641 | 6/1996 |
| EP | 0775472 | 5/1997 |
| EP | 0792627 | 9/1997 |
| EP | 0808613 | 11/1997 |
| EP | 0819411 | 1/1998 |
| EP | 0878175 | 11/1998 |
| EP | 0943302 | 9/1999 |
| EP | 0997115 | 5/2000 |
| EP | 0480667 | 4/2001 |
| EP | 1093772 | 4/2001 |
| EP | A 1138280 | 10/2001 |
| EP | 0808140 | 12/2001 |
| EP | 1163991 | 12/2001 |
| EP | 1212991 | 6/2002 |
| EP | 1266636 | 12/2002 |
| EP | 1380270 | 1/2004 |
| EP | 1415617 | 4/2004 |
| EP | 1 611 867 | 1/2006 |
| EP | 1611867 | 1/2006 |
| EP | 2 158 880 | 3/2010 |
| EP | 2158880 | 3/2010 |
| JP | 49 042773 | 4/1974 |
| JP | 3109404 | 5/1991 |
| JP | 5161665 | 6/1993 |
| JP | 6100054 | 4/1994 |
| JP | 09117511 | 5/1997 |
| JP | 18-126862 | 6/2006 |
| JP | 18-136382 | 6/2006 |
| RU | 1768154 | 10/1992 |
| RU | 1812980 | 4/1993 |
| RU | 2029527 | 2/1995 |
| SU | 1217402 | 3/1986 |
| SU | 1237201 | 6/1986 |
| SU | 1237202 | 6/1986 |
| SU | 1273077 | 11/1986 |
| SU | 1342511 | 10/1987 |
| SU | 1389778 | 4/1988 |
| SU | 1457921 | 2/1989 |
| SU | 1482714 | 5/1989 |
| SU | 1560134 | 4/1990 |
| SU | 1586718 | 8/1990 |
| SU | 1650127 | 5/1991 |
| SU | 1732964 | 5/1992 |

(56) References Cited

FOREIGN PATENT DOCUMENTS

| | | |
|---|---|---|
| WO | WO 91/00792 | 1/1991 |
| WO | WO 92/22604 | 12/1992 |
| WO | WO 93/13824 | 7/1993 |
| WO | WO 93/19804 | 10/1993 |
| WO | WO 94/03127 | 2/1994 |
| WO | WO 95/01761 | 1/1995 |
| WO | WO 95/03754 | 2/1995 |
| WO | WO 95/05132 | 2/1995 |
| WO | WO 95/09586 | 4/1995 |
| WO | WO 96/14095 | 5/1996 |
| WO | WO 96/14808 | 5/1996 |
| WO | WO 97/03624 | 2/1997 |
| WO | WO 97/07751 | 3/1997 |
| WO | WO 97/29716 | 8/1997 |
| WO | WO 97/48350 | 12/1997 |
| WO | WO 98/06355 | 2/1998 |
| WO | WO 98/20811 | 5/1998 |
| WO | WO 98/38947 | 9/1998 |
| WO | WO 98/41167 | 9/1998 |
| WO | WO 98/44870 | 10/1998 |
| WO | WO 98/44873 | 10/1998 |
| WO | WO 99/00073 | 1/1999 |
| WO | WO 99/26559 | 6/1999 |
| WO | WO 99/38455 | 8/1999 |
| WO | WO 99/43378 | 9/1999 |
| WO | WO 99/43379 | 9/1999 |
| WO | WO 00/10487 | 3/2000 |
| WO | WO 00/13613 | 3/2000 |
| WO | WO 00/42947 | 7/2000 |
| WO | WO 00/42948 | 7/2000 |
| WO | WO 00/44808 | 8/2000 |
| WO | WO 00/51522 | 9/2000 |
| WO | WO 00/67675 | 11/2000 |
| WO | WO 00/71179 | 11/2000 |
| WO | WO 01/05331 | 1/2001 |
| WO | WO 01/08599 | 2/2001 |
| WO | WO 01/15633 | 3/2001 |
| WO | WO 01/21108 | 3/2001 |
| WO | WO 01/30270 | 5/2001 |
| WO | WO 01/41675 | 6/2001 |
| WO | WO 01/56500 | 8/2001 |
| WO | WO 01/56504 | 8/2001 |
| WO | WO 01/58384 | 8/2001 |
| WO | WO 01/58387 | 8/2001 |
| WO | WO 01/66037 | 9/2001 |
| WO | WO 01/67993 | 9/2001 |
| WO | WO 01/74270 | 10/2001 |
| WO | WO 01/76509 | 10/2001 |
| WO | WO 01/82836 | 11/2001 |
| WO | WO 02/36332 | 5/2002 |
| WO | WO 02/41804 | 5/2002 |
| WO | WO 02/078569 | 10/2002 |
| WO | WO 02/083038 | 10/2002 |
| WO | WO 02/100454 | 12/2002 |
| WO | WO 03/022180 | 3/2003 |
| WO | WO 03/053287 | 7/2003 |
| WO | WO 03/053288 | 7/2003 |
| WO | WO 03/094795 | 11/2003 |
| WO | WO 03/094799 | 11/2003 |
| WO | WO 2004/002370 | 1/2004 |
| WO | WO 2004/002371 | 1/2004 |
| WO | WO 2004/017866 | 3/2004 |
| WO | WO 2004/019823 | 3/2004 |
| WO | WO 2004/078065 | 9/2004 |
| WO | WO 2005/037076 | 4/2005 |
| WO | WO 2005/086942 | 9/2005 |
| WO | WO 2005/115275 | 12/2005 |
| WO | WO 2006/107562 | 10/2006 |
| WO | WO 2007/096183 | 8/2007 |
| WO | WO 2009/042796 | 4/2009 |
| WO | WO 2009/086200 | 7/2009 |
| WO | WO 2009/132309 | 10/2009 |
| WO | WO 2010/127040 | 11/2010 |
| WO | WO 2011/100367 | 8/2011 |
| WO | WO 2012/068175 | 8/2012 |
| WO | WO 2016/065208 | 4/2016 |

OTHER PUBLICATIONS

International Search Report and Written Opinion mailed on Jul. 18, 2013 for International Application No. PCT/US2013/034654, filed on Mar. 29, 2013 and published as WO 2013/151896 on Oct. 10, 2013.

International Search Report and Written Opinion mailed on Jul. 18, 2013 for International Application No. PCT/US2013/034787, filed on Apr. 1, 2013 and published as WO 2013/151924 on Oct. 10, 2013.

Office Action mailed on Sep. 18, 2013 in U.S. Appl. No. 11/861,828, filed Sep. 26, 2007 and published as 2009-0082846 on Mar. 26, 2009.

Blum et al. "Abdominal aortic aneurysms: preliminary technical and clinical results with transfemoral placement of endovascular self-expanding stent-grafts" Radiology 198(1):25-31 (1996). ;198(1):25-31 (1996).

Blum et al. "Endoluminal stent-grafts for infrarenal abdominal aortic aneurysms" N Engl J Med 336(1):13-20 (1997). ;336(1):13-20 (1997).

Campbell et al., "Balloon-Artery Interactions During Stent Placement: A Finite Element Analysis Approach to Pressure, Compliance, and Stent Design as Contributors to Vascular Injury"; 1999; American Heart Association; pp. 378-383.

Canero et al., "Optimal stent implantation: three-dimensional evaluation of the mutual position of stent and vessel via intracoronary echocardiography," Computers in Cardiology, 261-264 (Sep. 1999).

Cooley, Denton A., Surgical Treatment of Aortic Aneurysms (Book), W.B. Saunders Company, West Washington Square, PA (1986).

Donayre, et al., "Fillable endovascular aneurysm repair", Endovascular Today, p. 64-66, Jan. 2009.

Dumoulin C. et al., "Mechanical behavior modeling of balloon expandable stents." Journal of Biomechanics, vol. 33, No. 11, pp. 1461-1470 (available online: Sep. 8, 2000).

Elger et al. "The Influence of Shape on the Stresses in Model Abdominal Aortic Aneurysms," Transactions of the ASME 326:326-32 (1996).

Ernst "Current therapy for infrarenal aortic aneurysms" N Engl J Med 336(1):58-60 (1997).

Haimovitch, L. and Patierson, N., "Robust growth is forecast for endovascular repair of AAAs," The BBI Newsletter, vol. 26, No. 5, pp. 113-144, (May 2003).

How et al. "Mechanical Properties of Arteries and Arterial Grafts," Chapter 1 of Cardiovascular Biomaterials Hasting, G.W. (ed.) London; New York: Springer-Verlag, 1992 pp. 1-35.

Lakshmiraghavan, M. Mechanical Wall Stress in Abdominal Aortic Aneurysm: Towards the Development of a Clinical Tool to Predict Aneurysm Rupture. Submitted to the University of Pittsburgh, vol. 59/09-B of Dissertation Abstracts International p. 4948. 285 pages (1998).

Mandai, S. et al. (1992). "Direct Thrombosis of Aneurysms with Cellulose Acetate Polymer. Part I: Results of Thrombosis in Experimental Aneurysms," *J. Neurosurgery* 77:497-500.

Mirich et al., "Percutaneously Placed Endovascular Grafts for Aortic Aneurysms: Feasibility Study", Radiology, 170/3:1033-1037 (1989).

Moore et al. "Transfemoral endovascular repair of abdominal aortic aneurysm: results of the North American EVT phase 1 trial" J Vasc Surg 23(4):543-553 (1996).;23(4):543-553 (1996).

Mower et al. "Stress Distributions in Vascular Aneurysms: Factors Affecting Risk of Aneurysm Rupture," J. Surgical Research 55:151-61 (1993).

Parodi "Endovascular repair of abdominal aortic aneurysms and other arterial lesions" J Vasc Surg 21(4):549-557 (1995).;21(4):549-557 (1995).

(56) References Cited

OTHER PUBLICATIONS

Parodi et al., "Transfemoral intraluminal graft implantation for abdominal aortic aneurysms," Ann. Vasc. Surg., 5(6):491-499 (1991).
Perry, M. D. and Chang, R. T., "Finite Element Analysis of Ni—Ti Alloy Stent Deployment," Proceedings of the Second International Conference on SMST, Asilomar Conference Center, Pacific Grove CA. USA (1997).
Rogers et al., "Balloon-Artery Interactions During Stent Placement: A finite element analysis approach to pressure, compliance and stent design as contributors to vascular injury", 1999 American Heart Association pp. 378-383.
Stern et al., "Interactive Definition of Endoluminal Aortic Stent Size and Morphology Based on Virtual Angioscopic Rendering of 3D Magnetic Resonance Angiography (MRA)," Cars. Computer Assisted Radiology and Surgery, Proceedings of the International Symposium on Computer Assisted Radiology and Surgery:176-180 (Jun. 1999).
The AneuRx® Stent Graft System Treatment for AAA brochure, "An Innovative Modular Approach for the Treatment of Abdominal Aortic Aneurysms (AAA)," Medtronic Ave, Inc. 1999.
The AneuRx® Stent Graft Treatment for TAA brochure, "An Endoluminal Solution for the Treatment of Descending Thoracic Aortic Aneurysms," Medtronic, Inc. 1999.
U.S. Appl. No. 10/168,053, filed Jun. 14, 2002, entitled Inflatable Intraluminal Graft, by C. Murch.
Uflacker, R. And Robinson, J., "Endovascular treatment of abdominal aortic aneurysms: a review," Eur. Radial., 11:739-753 (2001).
Verhagen "Latest AAA Innovations: The Rndurant Stent Graft System", Veith Symposium Nov. 17, 2007.
Verhagen, Hence J.M. "Endurant Medtronic Endograft for EVAR: advantages & early experience", Slides from Veith Symposium Presentation Nov. 22, 2008.
Volodos, N.L. et al. (1987). "New Balloon Catheter for Dilating Arteries and Installing Prosthesis During Distal Endoprosthetics With Self-Fixing Synthetic Prosthesis," *Thesis of VIII Symposium* (Oct. 8-10, 1987), Abstract Only in English, four pages.
Volodos, N.L. et al. (1986) "Self-Fixing Synthetic Prostheisis for Endoprosthesis of Vessels," Vestnik Khigurgii pp. 123-124, Abstract Only in English.
Volodos, N.L. et al. (1989). "Clinical Experience in Use of Self-Fixing Synthetic Prosthesis for Distal and Intraoperative Endoprosthestics of Aora and Iliac Arteries," Theses of lxth All-Union Symposium (Oct. 2-3, 1989), Abstract only in English, four pages.
Vos, A.F.W. et al., "Endovascular Grafting of Complex Aortic Aneurysms with a modular Side Branch Stent Graft System in a Porcine Model", Eur J Vasc Endovasc Surg, May 2004 vol. 27 492-497.
Web page, "Drug Eluting Stents—Why Use Drug Eluting Stents?;" Polymer Coatings Division; at URL http://www.lombardmedlcal.co.uk/lombard/pcde.why.html; Lombard Medical; printed Feb. 1, 2005.
Whitcher, "Simulation of in vivo loading conditions of nitinol vascular stent structures", 1997, Elsevier Science Ltd., pp. 1005-1011.
Whitcher, F., "A Finite Element Treatment of the In-Vivo Loading Conditions of NITI AD Vascular Stent and Graft Structures," Proceedings of the Second International Conference on SMST, Asilomar Conference Center, Pacific Grove. CA, USA (1997).
Wisselink, W. et al. (2001). "Clipping of Inferior Mesenteric and Lumbar Arteries via Retroperitoneal Laparo-Endoscopic Approach as a Treatment of Persistent Endoleak" Chapter 18 in Endoleaks and Endotension, Veith, F.J. et al. eds. Marcel Dekker, Inc. pp. 211-220.
Extended European Search Report dated: Dec. 17, 2012 in European Application No. EP 08835032 filed: Oct. 3, 2008.
Extended European Search Report Mailed Jul. 27, 2010 in European Application No. 10005904.7 filed: Apr. 11, 2002 and published as: EP 2221023 on Aug. 25, 2010.
Extended European Search Report Mailed Dec. 16, 2009 in European Application No. 09175398.8 filed: Oct. 15, 2004 and published as: EP 2145607 on Jan. 20, 2010.
Extended European Search Report dated: Apr. 5, 2013 in European Application No. EP 08849544 filed: Nov. 13, 2008.
International Preliminary Report on Patentability mailed on Apr. 15, 2010 for International Application No. PCT/US2008/078846 filed on Oct. 3, 2008 and published as WO/2009/046372 on Apr. 9, 2009.
International Search Report and Written Opinion mailed on Jul. 30, 2009 for International Application No. PCT/US2008/078846 filed on Oct. 3, 2008 and published as WO/2009/046372 on Apr. 9, 2009.
International Preliminary Report on Patentability mailed on Apr. 8, 2010 for International Application No. PCT/US2008/077714 filed on Sep. 25, 2008 and published as WO/2009/042789 on Apr. 2, 2009.
International Search Report and Written Opinion mailed on: May 1, 2009 for International Application No. PCT/US2008/077714 filed on Sep. 25, 2008 and published as WO/2009/042789 on Apr. 2, 2009.
International Preliminary Report on Patentability mailed on May 27, 2010 for International Application No. PCT/US2008/083451 filed on Nov. 13, 2008 and published as WO/2009/064923 on May 22, 2009.
International Search Report and Written Opinion May 1, 2009 mailed on Jun. 30, 2009 for International Application No. PCT/US2008/083451 filed on Nov. 13, 2008 and published as WO/2009/064923 on May 22, 2009.
International Preliminary Report on Patentability mailed on Apr. 8, 2010 for International Application No. PCT/US2008/077727 filed on Sep. 25, 2008 and published as WO2009/042796 on Apr. 2, 2009.
International Search Report and Written Opinion mailed on Mar. 26, 2009 for International Application No. PCT/US2008/077727 filed on Sep. 25, 2008 and published as WO/2009/042796 on Apr. 2, 2009.
International Preliminary Report on Patentability mailed on Jul. 1, 2010 for International Application No. PCT/US2008/087831 filed on Dec. 19, 2008 and published as WO/2009/086200 on Jul. 9, 2009.
International Search Report and Written Opinion mailed on May 28, 2009 for International Application No. PCT/US2008/087831 filed on Dec. 19, 2008 and published as WO/2009/086200 on Jul. 9, 2009.
International Search Report and Written Opinion mailed on Oct. 31, 2011 for International Application No. PCT/US2011/024248 filed on Feb. 9, 2011 and published as WO/2011/100367 on Aug. 28, 2011.
Invitation to Pay Additional Fees and Partial Search Report dated: Apr. 25, 2013 for International Application No. PCT/US2011/060873 filed on Nov. 15, 2011 and published as WO/2012/068175 on Aug. 2, 2012.
Office Action mailed on: Aug. 18, 2011 in U.S. Appl. No. 11/941,450, filed Nov. 16, 2007 and published as: 2009/0132020 on: May 21, 2009.
Office Action mailed on: May 3, 2011 in U.S. Appl. No. 11/941,450, filed Nov. 16, 2007 and published as: 2009/0132020 on: May 21, 2009.
Office Action mailed on: Dec. 9, 2010 in U.S. Appl. No. 11/941,450, filed Nov. 16, 2007 and published as: 2009/0132020 on: May 21, 2009.
Office Action Response mailed on: Sep. 10, 2010 in U.S. Appl. No. 11/941,450, filed Nov. 16, 2007 and published as: 2009/0132020 on: May 21, 2009.
Office Action mailed on: Mar. 15, 2010 in U.S. Appl. No. 11/941,450, filed Nov. 16, 2007 and published as: 2009/0132020 on: May 21, 2009.
Office Action Response mailed on: Nov. 20, 2009 in U.S. Appl. No. 11/941,450, filed Nov. 16, 2007 and published as: 2009/0132020 on: May 21, 2009.
Office Action mailed on: Oct. 22, 2009 in U.S. Appl. No. 11/941,450, filed Nov. 16, 2007 and published as: 2009/0132020 on: May 21, 2009.

(56) References Cited

OTHER PUBLICATIONS

Office Action mailed on: Jul. 30, 2012 for U.S. Appl. No. 11/941,434, filed Nov. 16, 2007 and published as US2009/0132026 on May 21, 2009.
Office Action Response mailed on: May 22, 2012 for U.S. Appl. No. 11/941,434, filed Nov. 16, 2007 and published as US2009/0132026 on May 21, 2009.
Office Action mailed on: Apr. 12, 2012 for U.S. Appl. No. 11/941,434, filed Nov. 16, 2007 and published as US2009/0132026 on May 21, 2009.
Office Action Response mailed on: Feb. 17, 2012 for U.S. Appl. No. 11/941,434, filed Nov. 16, 2007 and published as US2009/0132026 on May 21, 2009.
Office Action mailed on: Aug. 12, 2011 for U.S. Appl. No. 11/941,434, filed Nov. 16, 2007 and published as US2009/0132026 on May 21, 2009.
Office Action Response mailed on: Jun. 3, 2011 for U.S. Appl. No. 11/941,434, filed Nov. 16, 2007 and published as US2009/0132026 on May 21, 2009.
Office Action mailed on: Jan. 3, 2011 for U.S. Appl. No. 11/941,434, filed Nov. 16, 2007 and published as US2009/0132026 on May 21, 2009.
Office Action mailed: Mar. 14, 2013 in U.S. Appl. No. 13/024,255, filed Feb. 9, 2011 and published as: 2011/0218609 on : Sep. 8, 2011.
International Search Report and Written Opinion mailed on Jul. 18, 2013 for International Application No. PCT/US2013/034654 filed on Mar. 29, 2013.
International Search Report and Written Opinion mailed on Jul. 18, 2013 for International Application No. PCT/US2013/034787 filed on Apr. 1, 2013.
Office Action Response dated: Aug. 26, 2015 in U.S. Appl. No. 13/024,255 dated Feb. 9, 2011 and published as: US2011/0218609 on: Sep. 8, 2011.
Office Action dated: Mar. 26, 2015 in U.S. Appl. No. 13/024,255 dated Feb. 9, 2011 and published as: US2011/0218609 on: Sep. 8, 2011.
Office Action Response dated: Feb. 20, 2014 in U.S. Appl. No. 13/024,255 dated Feb. 9, 2011 and published as: US2011/0218609 on: Sep. 8, 2011.
Office Action dated: Nov. 20, 2013 in U.S. Appl. No. 13/024,255 dated Feb. 9, 2011 and published as: US2011/0218609 on: Sep. 8, 2011.
Office Action Response dated: Aug. 5, 2013 in U.S. Appl. No. 13/024,255 dated Feb. 9, 2011 and published as: US2011/0218609 on: Sep. 8, 2011.
Office Action dated: Oct. 1, 2014 in U.S. Appl. No. 13/297,219, filed Nov. 15, 2011 and published as: US2012/0191174 on: Jul. 26, 2012.
Office Action Response dated: Jun. 30, 2014 in U.S. Appl. No. 13/297,219, filed Nov. 15, 2011 and published as: US2012/0191174 on: Jul. 26, 2012.
Office Action dated: Mar. 28, 2014 in U.S. Appl. No. 13/297,219, filed Nov. 15, 2011 and published as: US2012/0191174 on: Jul. 26, 2012.
Invitation to Pay Additional Fees and Partial Search Report dated: Apr. 25, 2012 for International Application No. PCT/US2011/060873 filed on Nov. 15, 2011 and published as WO/2012/068175 on Aug. 2, 2012.
International Search Report and Written Opinion mailed on Jun. 12, 2012 for International Application No. PCT/US2011/060873 filed on Nov. 15, 2011 and published as WO/2012/068175 on Aug. 2, 2012.
Extended European Search Report dated: Jan. 27, 2015 in European Application No. EP 11841183.4 filed: Nov. 15, 2011.
Supplemental European Search Report dated: Feb. 13, 2015 in European Application No. EP 11841183.4 filed: Nov. 15, 2011.
Office Action dated: Dec. 11, 2015 in U.S. Appl. No. 13/024,255 dated Feb. 9, 2011 and published as: US2011/0218609 on: Sep. 8, 2011.
Extended European Search Report dated Oct. 8, 2015 in European Application No. EP 13771941.5 filed: Apr. 1, 2013.
Extended European Search Report dated: Nov. 9, 2015 in European Application No. EP 13772199.9 filed: Mar. 29, 2013.
International Search Report and Written Opinion dated: Feb. 2, 2016 in International Patent Application No. PCT/US2015/057016 filed: Oct. 22, 2015 and published as: WO/2016/065208 on: Apr. 28, 2016.

* cited by examiner

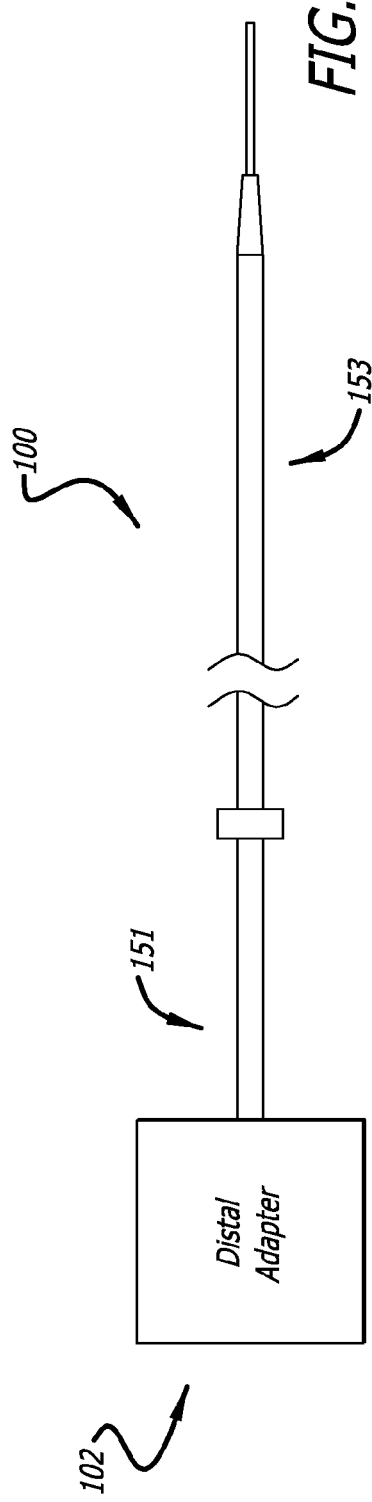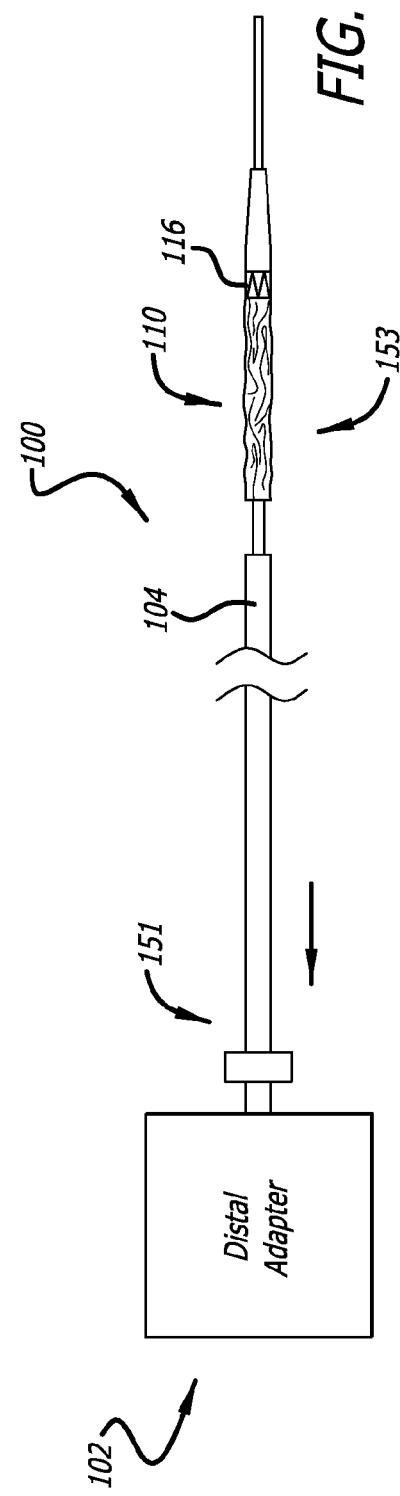

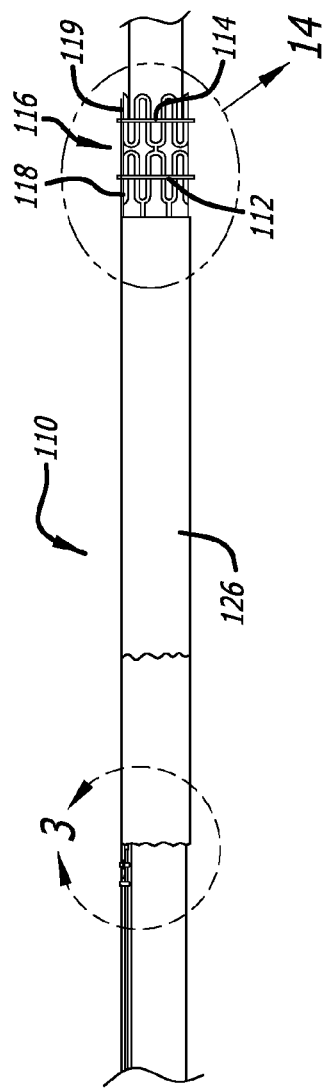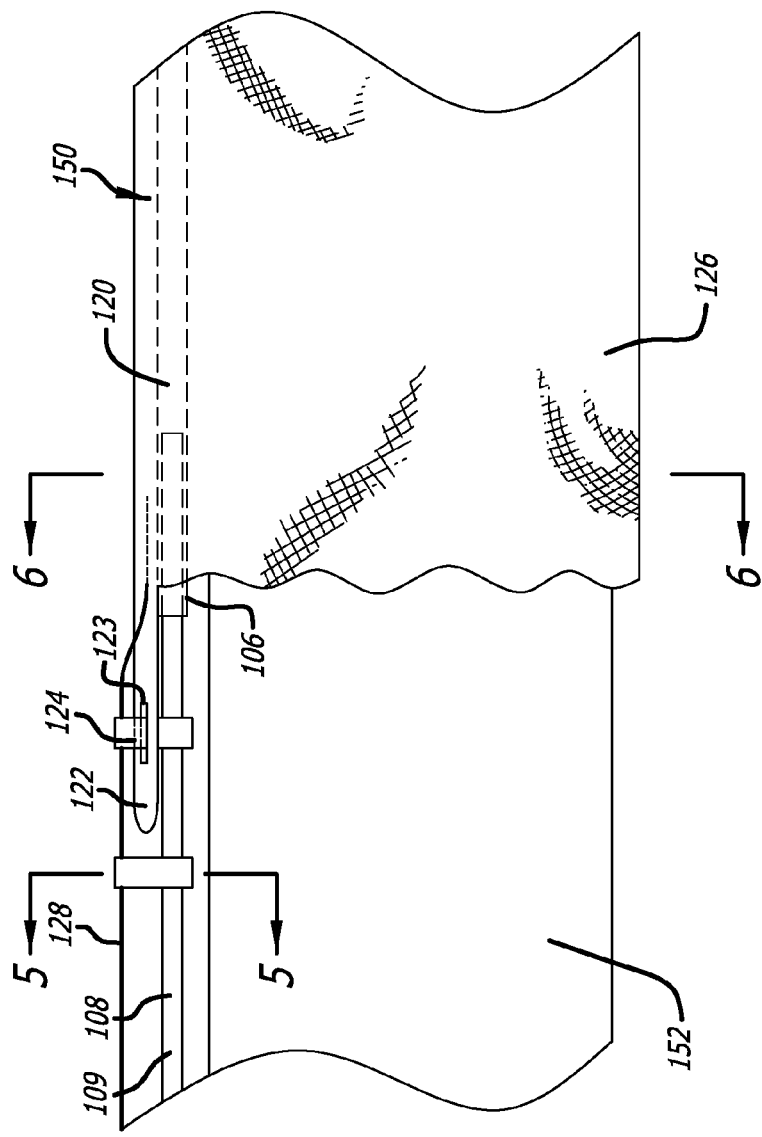
FIG. 2
FIG. 3

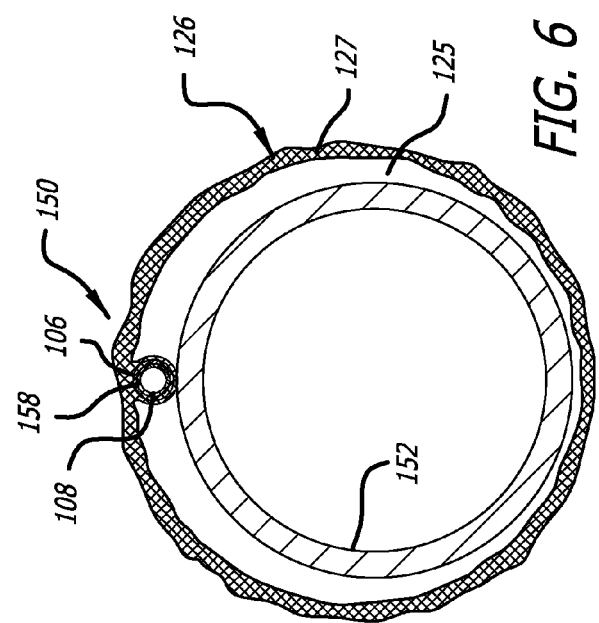
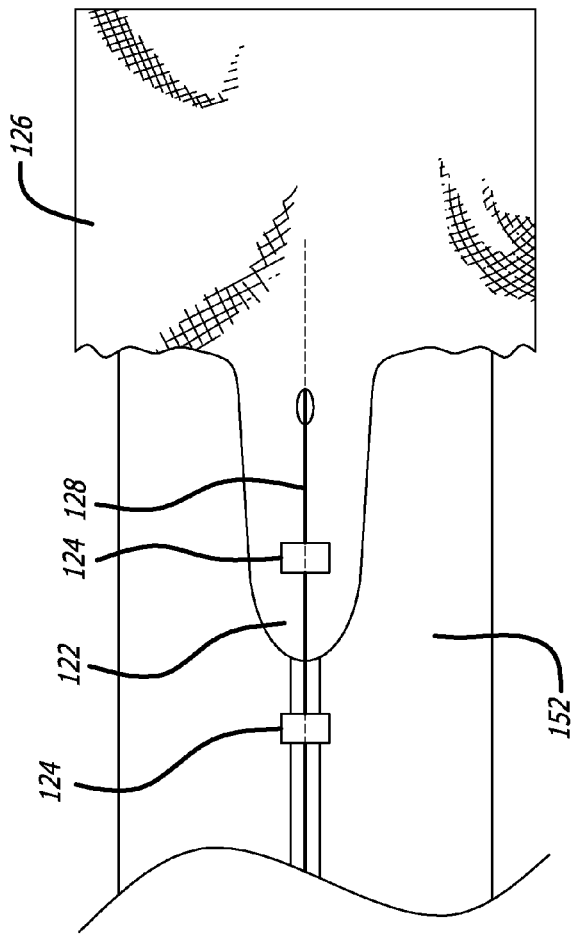
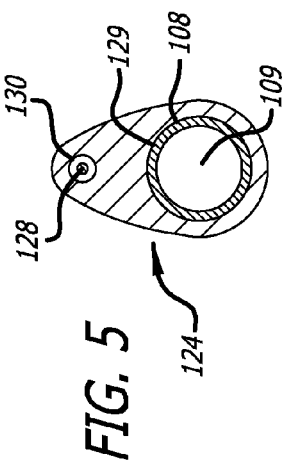

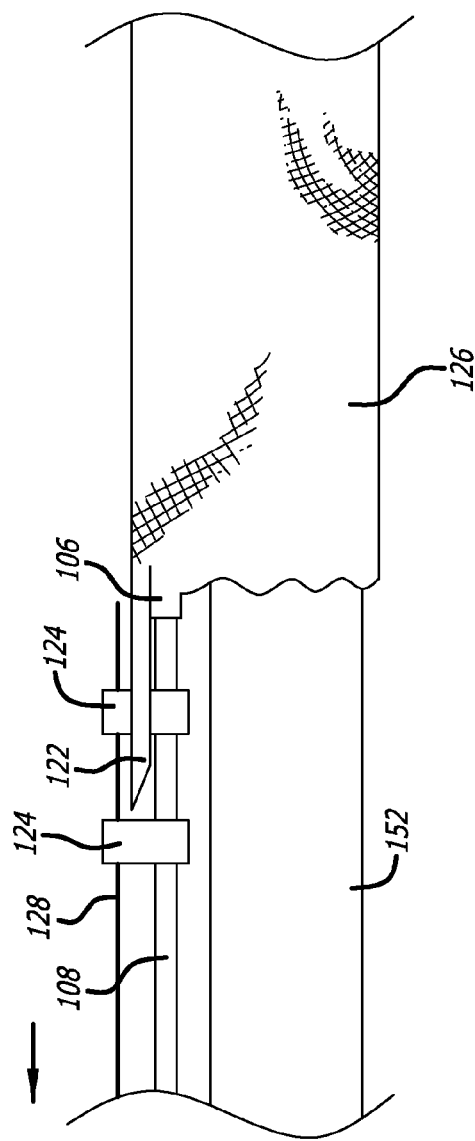

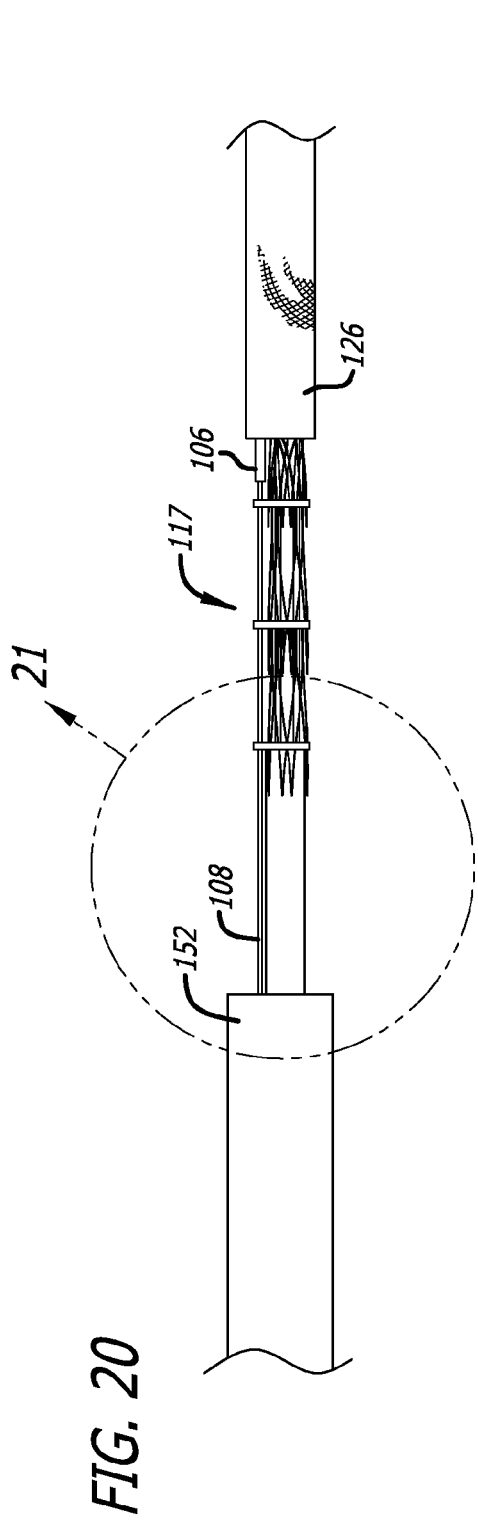
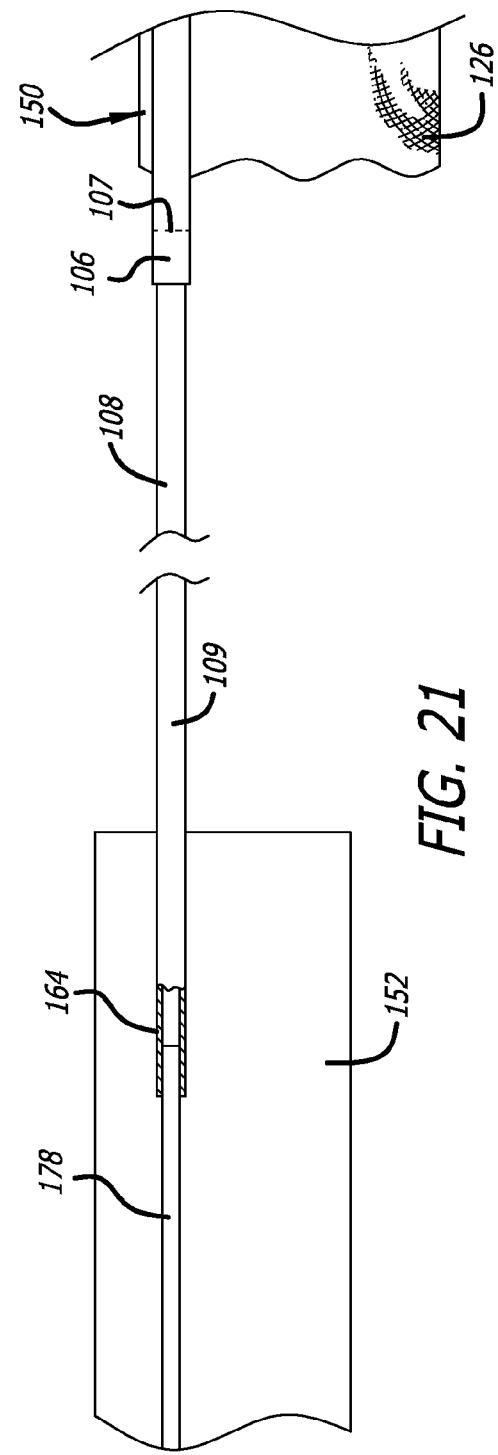
FIG. 20
FIG. 21

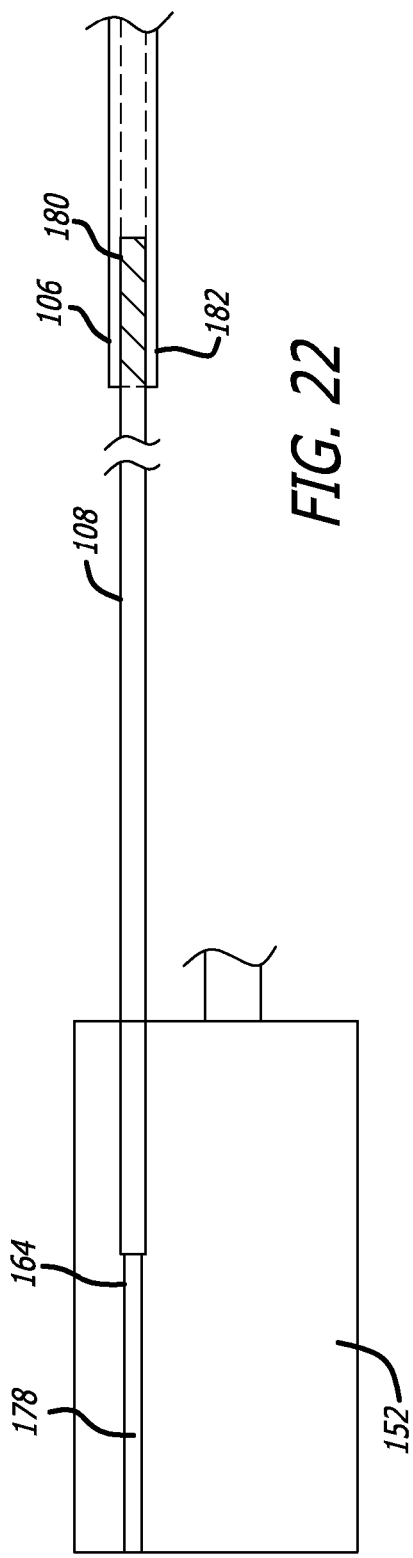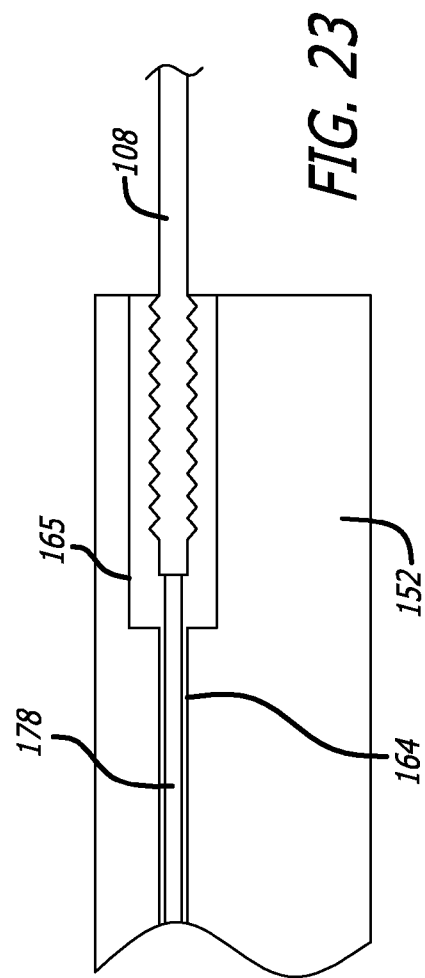

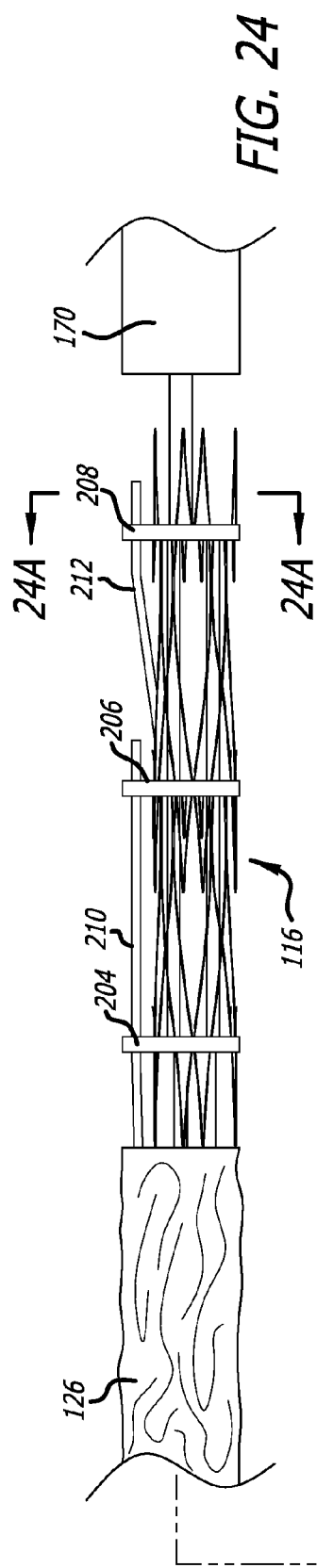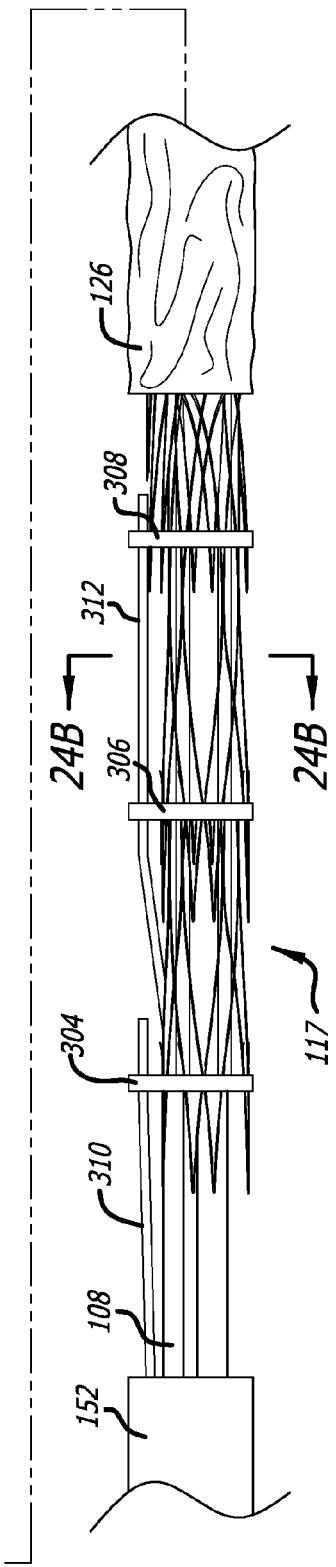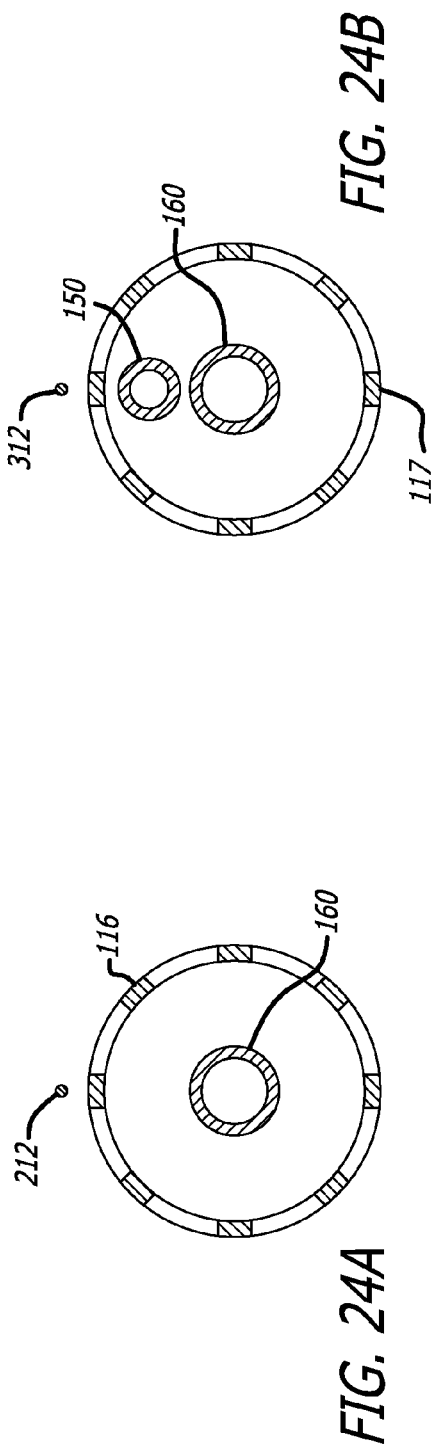

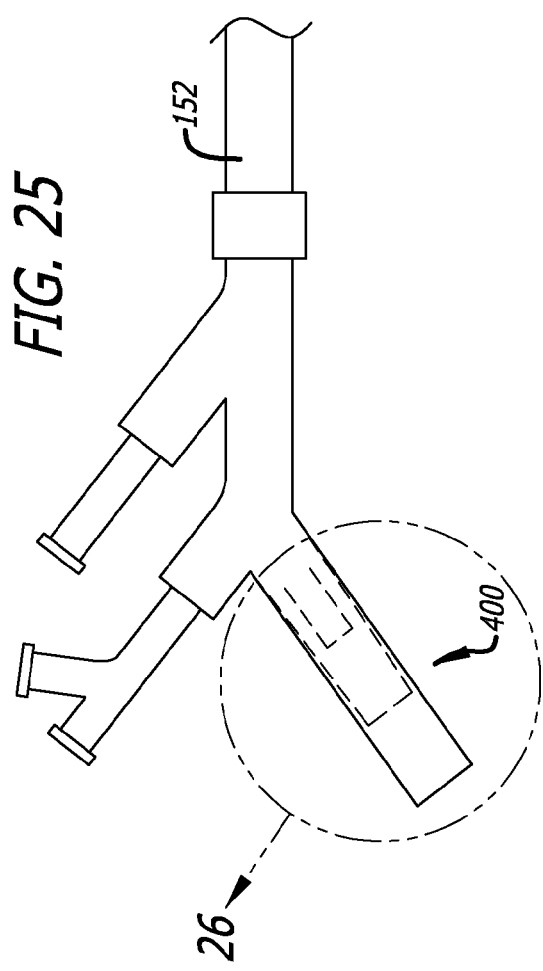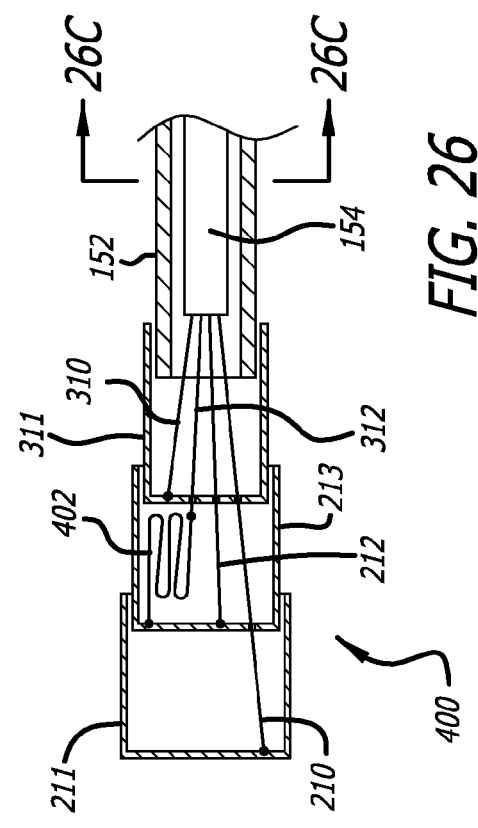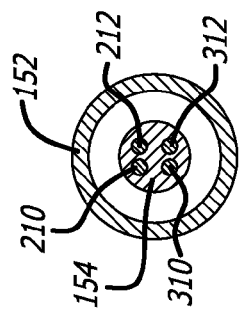

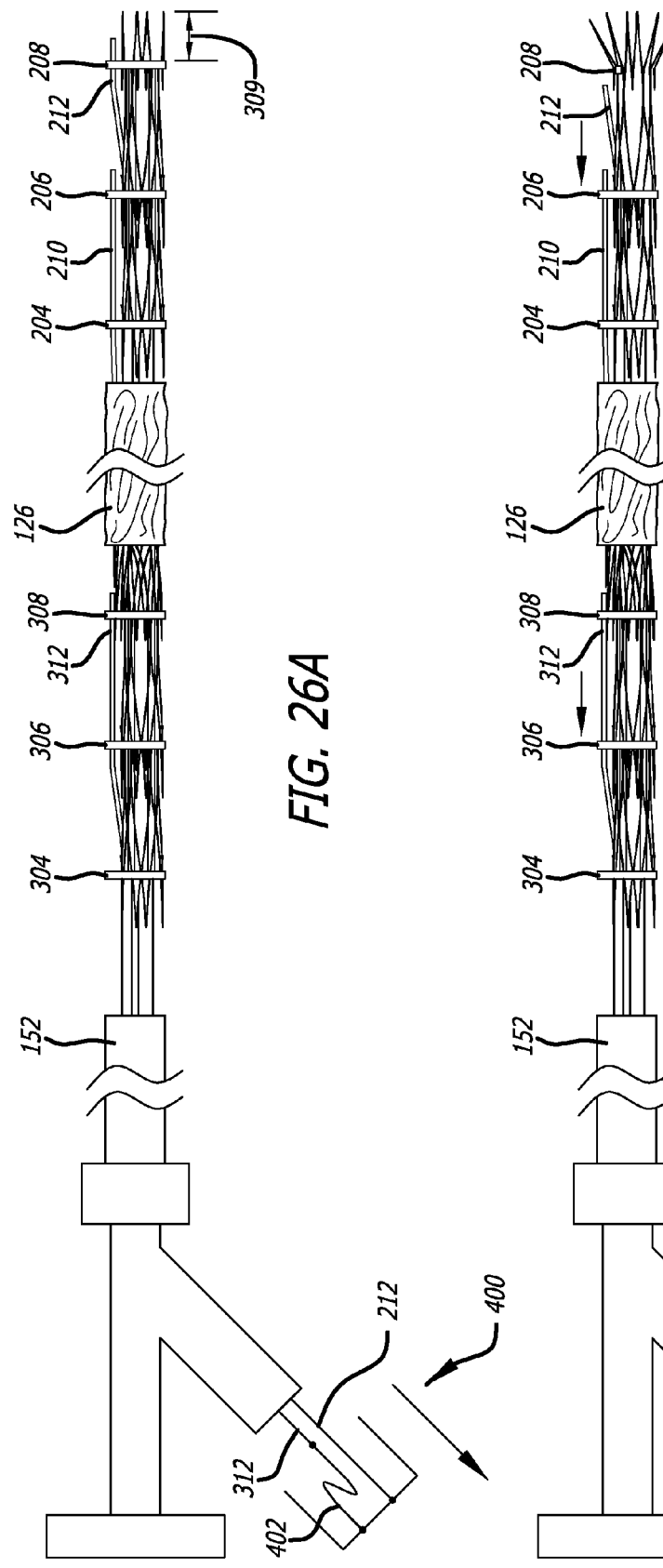
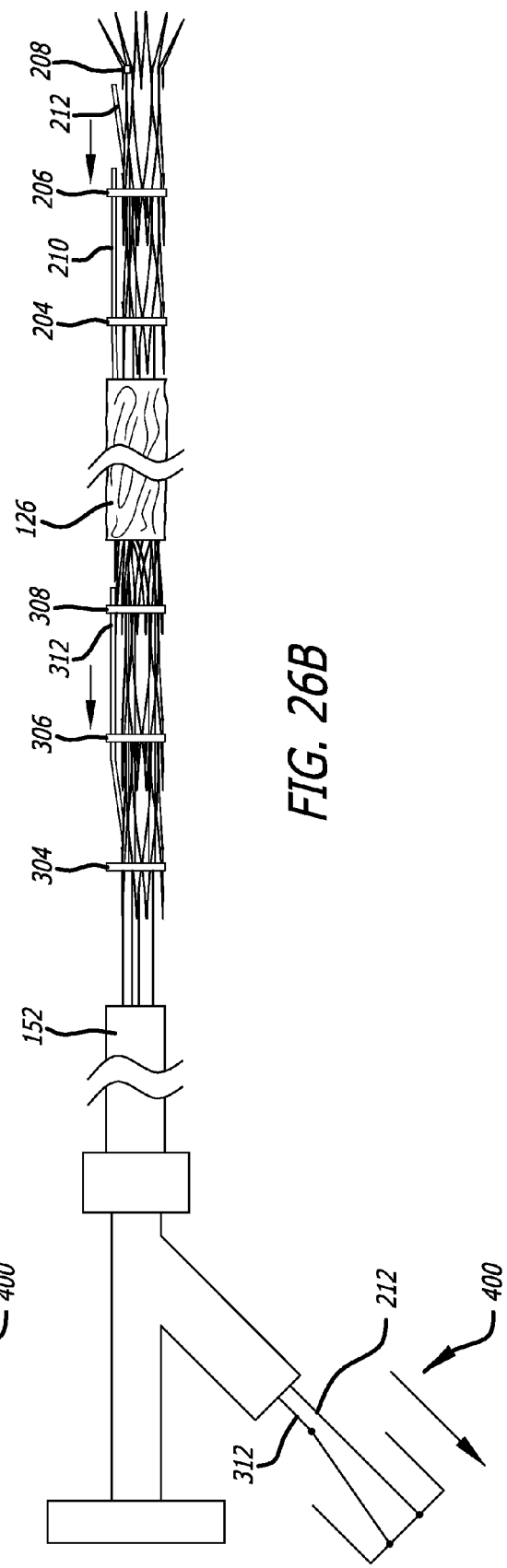

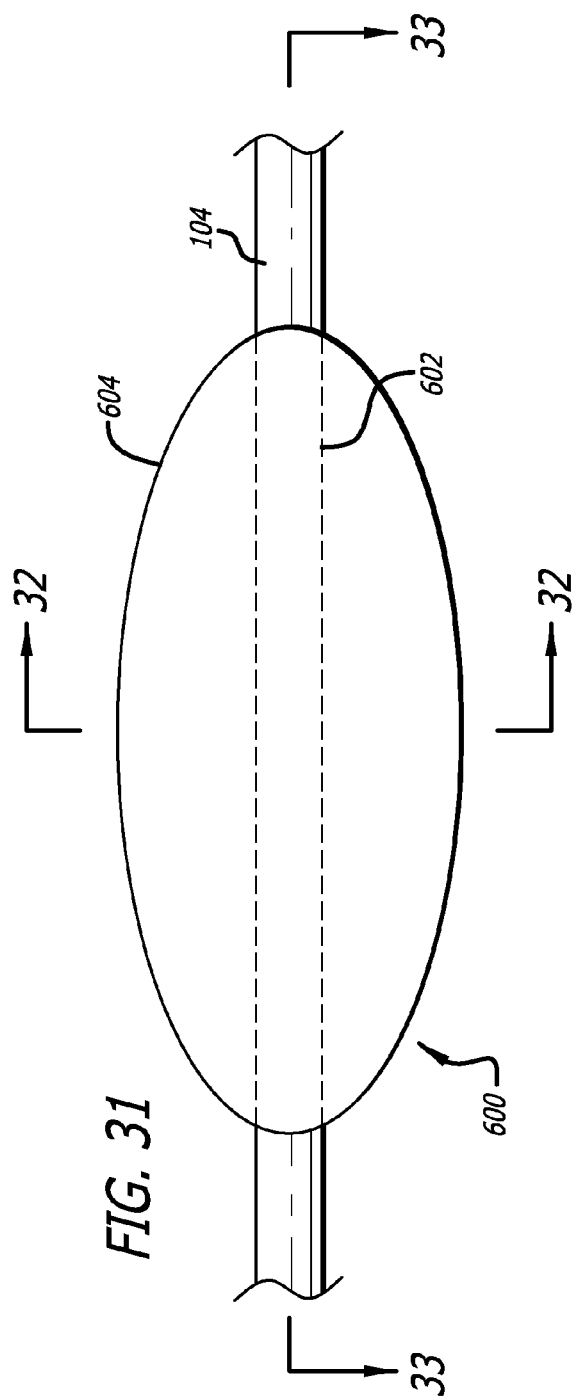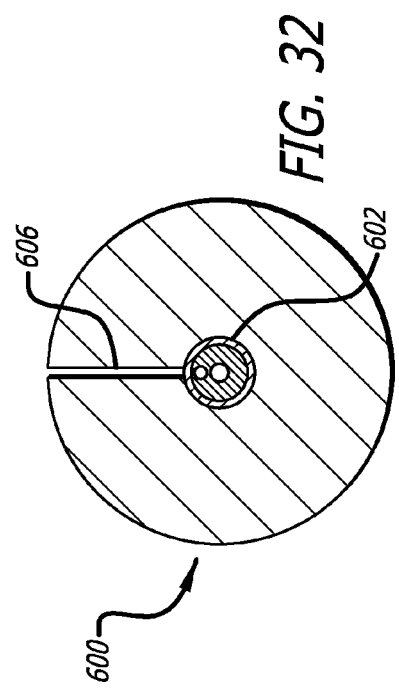

DELIVERY CATHETER FOR ENDOVASCULAR DEVICE

RELATED APPLICATIONS

This application claims priority under 35 U.S.C. 119(e) from U.S. Provisional Patent Application No. 61/621,286, filed Apr. 6, 2012, by J. Watson et al., titled Delivery Catheter for Endovascular Device, which is incorporated by reference herein in its entirety.

FIELD OF THE INVENTION

Some embodiments relate in part to endovascular prostheses and methods of deploying same. Embodiments may be directed more specifically to stent grafts and methods of making and deploying same within the body of a patient.

BACKGROUND

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of a AAA is described in a book titled Surgical Treatment of Aortic Aneurysms by Denton A. Cooley, M.D., published in 1986 by W. B. Saunders Company.

Due to the inherent risks and complexities of surgical repair of aortic aneurysms, endovascular repair has become a widely-used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the AneuRx® stent graft manufactured by Medtronic, Inc. of Minneapolis, Minn., the Zenith® stent graft system sold by Cook, Inc. of Bloomington, Ind., the PowerLink® stent-graft system manufactured by Endologix, Inc. of Irvine, Calif., and the Excluder® stent graft system manufactured by W.L. Gore & Associates, Inc. of Newark, Del. A commercially available stent graft for the treatment of TAAs is the TAG™ system manufactured by W.L. Gore & Associates, Inc.

When deploying devices by catheter or other suitable instrument, it is advantageous to have a flexible and low profile stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. Also, such existing systems have greater than desired lateral stiffness, which can complicate the delivery process. In addition, the sizing of stent grafts may be important to achieve a favorable clinical result. In order to properly size a stent graft, the treating facility typically must maintain a large and expensive inventory of stent grafts in order to accommodate the varied sizes of patient vessels due to varied patient sizes and vessel morphologies. Alternatively, intervention may be delayed while awaiting custom size stent grafts to be manufactured and sent to the treating facility. As such, minimally invasive endovascular treatment of aneurysms is not available for many patients that would benefit from such a procedure and can be more difficult to carry out for those patients for whom the procedure is indicated.

What have been needed are stent graft systems and methods that are adaptable to a wide range of patient anatomies and that can be safely and reliably deployed using a flexible low profile system.

SUMMARY

Some embodiments are directed to a delivery system for an inflatable endoluminal prosthesis having a delivery catheter. In some embodiments, the delivery catheter may have an elongate shaft including a proximal section and a fill tube including a fill tube lumen extending axially within the fill tube. In some cases, the endoluminal prosthesis may be releasably secured to the proximal section of the delivery catheter. The endoluminal prosthesis may include an inflatable portion with an interior volume in fluid communication with an inflation port which may be releasably coupled to a proximal end of the fill tube. In some embodiments, a fill tube retention mechanism may releasably secure the fill tube lumen of the fill tube in fluid communication with the inflation port. The fill tube retention mechanism may have a tab which is disposed at a distal end of the endoluminal prosthesis in substantially fixed relation to the inflation port and which may include an aperture in the tab which is separated from the inflation port by a predetermined distance in some embodiments. In some embodiments, a fitting may be secured to a proximal portion of the fill tube of the delivery catheter which may extend laterally from the fill tube and which may include at least a portion that is sized to pass through the aperture in the tab. In some instances, the tab may be disposed a distance from a proximal end of the fill tube which allows the fill tube to be engaged with the inflation port while the fitting may be disposed within the aperture in the tab. A fitting may include a passage through the fitting in some embodiments. In some cases, a release wire having an outer transverse dimension and axial bending stiffness that allows the release wire to pass through the passage of the fitting may assist in mechanically capturing the tab to the fitting. The tab may be disposed between the release wire and the fill tube with the release wire disposed in the passage in some embodiments. In some cases, the tab includes PTFE material.

Some embodiments of the delivery catheter for delivery of an inflatable endoluminal prosthesis may include an elongate shaft having a proximal section and a fill tube. In some cases, the fill tube may include a fill tube lumen in fluid communication with a distal section of the elongate shaft and extending axially therein. In addition, a fitting may be secured to a proximal portion of the fill tube of the delivery catheter which may extend laterally from the fill tube and which may include at least a portion that may be sized to pass through an aperture in a tab of an endoluminal prosthesis in some embodiments. In some cases, the tab may be disposed a distance from a proximal end of the fill tube which may be configured to allow the fill tube to be engaged with an inflation port of an inflatable endoluminal prosthesis. The fitting may have a passage through the fitting in some embodiments. In some cases, a release wire including an outer transverse dimension and axial bending stiffness that allows the release wire to pass through the passage of the fitting may mechanically capture a tab of an endoluminal prosthesis to the fitting. The tab may be disposed between the release wire and the fill tube with the release wire disposed in the passage in some embodiments. In some cases, the passage of the fitting includes an axial passage which is substantially parallel to the lumen of the fill tube. In some instances, the release wire extends from the fitting to a distal end of the catheter and is coupled to a release mechanism which is disposed at a distal end of the delivery catheter and which is configured to apply axial tension and displacement to the release wire in order to axially retract the release wire and release the fitting from an aperture of a tab of an endoluminal prosthesis. For some embodiments, the fill tube may include a plurality of fittings, a plurality of release wires, a transverse dimension of about 1 mm to about 2 mm or both. In some cases, an outer transverse dimension of the fill tube may be configured to slide within an inner lumen of a inflation port of an endoluminal prosthesis and provide a seal therebetween for viscous fluids.

Some embodiments are directed to a method of releasably securing a fill tube of a delivery catheter to an inflation port of an inflatable portion of an inflatable endoluminal prosthesis. The method may include delivering an endoluminal prosthesis to a treatment site with the endoluminal prosthesis being releasably secured to a proximal section of a delivery catheter. In some embodiments, the endoluminal prosthesis may include an inflatable portion with an interior volume in fluid communication with an inflation port. A proximal end of a fill tube of the delivery catheter may be releasably coupled to the inflation port with a fill tube retention mechanism that releasably secures the fill tube lumen of the fill tube in fluid communication with the inflation port in some embodiments. In some cases, the fitting may be released from the tab by retracting the release wire from the passage such that the tab may be no longer mechanically captured over the fitting between the fill tube and the release wire. The fill tube retention mechanism may include a flexible tab disposed at a distal end of the endoluminal prosthesis in fixed relation to the inflation port and may include an aperture in the tab which may be separated from the inflation port by a predetermined distance in some embodiments. In some cases, the fill tube retention mechanism may further include a fitting secured to a proximal portion of the fill tube of the delivery catheter which may extend laterally from the fill tube and include at least a portion that may be sized to pass through the aperture in the tab. Furthermore, the fitting may be positioned a distance from a proximal end of the fill tube such that it may allow the fill tube to be engaged with the inflation port while the fitting may be disposed within the aperture in some embodiments. In some instances, the fitting may include a passage through the fitting which may be positioned so as to allow the tab to be disposed between the release wire and the fill tube with the release wire disposed in the passage. In some embodiments, the fill tube retention mechanism may further include a release wire having an outer transverse dimension and axial bending stiffness that allows the release wire to pass through the passage of the fitting and mechanically capture the tab to the fitting. In some cases, the elongate shaft may further include a retractable outer sheath that is disposed over the elongate release wire sleeve and is configured to removably cover a constrained endoluminal prosthesis disposed on the proximal section of the elongate shaft. In some instances, the delivery catheter may further include a proximal nosecone having a bullet-shaped profile and a shoulder portion with an outer surface which is configured to slidingly accept an inner luminal surface of the outer sheath.

Some embodiments are directed to a delivery catheter for delivery of an endoluminal prosthesis having an elongate shaft with sufficient column strength for percutaneous advancement within a patient's body lumen. The elongate shaft may include a proximal section and a lumen extending therein in some embodiments. In some instances, a plurality of releasable belts disposed on the proximal section of the elongate shaft may be configured to releasably constrain a self-expanding member of an endoluminal prosthesis. In some embodiments, a plurality of elongate release members may be in communication with a distal end of the elongate shaft and may include a proximal section configured to releasably secure at least one respective releasable belt while said releasable belt is in a configuration that constrains at least a portion of an endoluminal prosthesis. The elongate shaft may have an elongate release wire sleeve disposed within the lumen extending within the elongate shaft in some cases. Additionally, the elongate release wire sleeve may include a low friction material and extend from a distal section to a proximal section of the elongate shaft. The elongate release wire sleeve may include a separate lumen for each release member in some embodiments.

Some embodiments are directed to a delivery system for percutaneous delivery of and endoluminal prosthesis, including an elongate shaft with sufficient column strength for percutaneous advancement within a patient's body lumen. The elongate shaft may include a proximal section and a lumen extending therein in some embodiments. In some instances, a plurality of releasable belts disposed on the proximal section of the elongate shaft may be configured to releasably constrain a self-expanding member of an endoluminal prosthesis. In some embodiments, a plurality of elongate release members may be in communication with a distal end of the elongate shaft and may include a proximal section configured to releasably secure at least one respective releasable belt while said releasable belt may be in a configuration that constrains at least a portion of an endoluminal prosthesis. In some cases, the elongate shaft may include an elongate release wire sleeve disposed within the lumen extending within the elongate shaft. Additionally, the elongate release wire sleeve may include a low friction material extending from a distal section to a proximal section of the elongate shaft in some embodiments. The elongate release wire sleeve may include a separate lumen for each release member in some cases. An endoluminal prosthesis may include a tubular body portion of flexible material and a self-expanding member secured to a proximal end of the tubular body member in some embodiments. The endoluminal prosthesis may be releasably secured to the proximal section of the delivery catheter by the releasable belts disposed about and releasably constraining the self-expanding member of the endoluminal prosthesis in some embodiments. In some cases, the endoluminal prosthesis further includes an inflatable portion with an interior volume in fluid communication with an inflation port and a proximal end of the fill tube of the catheter releasably coupled to the inflation port. In some instances, the tubular body portion has a bifurcated configuration. Also, the low friction material of the elongate release wire sleeve may include a fluoropolymer such as PTFE. For some such embodiments, the PTFE of the elongate release wire sleeve may include a shore hardness of about 40 D to about 70 D and the elongate release member may include an elongate release wire or both. In some cases, the delivery catheter may be configured to deliver an inflatable endovascular prosthesis wherein the delivery catheter may further include a fill tube including a fill tube lumen extending axially within the elongate shaft. In some instances, the elongate shaft may include a guidewire lumen extending from a distal section to a proximal end thereof. For some embodiments, the elongate shaft may include an elongate multi-lumen member extending from a distal section of the elongate shaft to a proximal section of the elongate shaft, the multi-lumen member having a guidewire lumen and a lumen within which the elongate release wire sleeve is disposed. In some cases, the elongate shaft may further include a retractable outer sheath that is disposed over the elongate release wire sleeve and that is configured to removably cover a constrained endoluminal prosthesis disposed on the proximal section of the elongate shaft. In some instances, the delivery system may further include a proximal nosecone including a bullet-shaped profile and a shoulder portion having an outer surface which is configured to slidingly accept an inner luminal surface of the outer sheath.

Some embodiments are directed to a delivery catheter for delivery of an inflatable endoluminal prosthesis including an elongate shaft which may have sufficient column strength for percutaneous advancement within a patient's body lumen. In some embodiments, the elongate shaft may include a proximal section which may be configured to accept an inflatable endoluminal prosthesis releasably secured thereto. Additionally, a fill lumen may be in fluid communication with a distal section of the elongate shaft and may extend to the proximal section of the elongate shaft in some embodiments. Some embodiments may include a collapsible low profile fill tube including an inner lumen which may be in fluid communication with the fill lumen of the elongate shaft. In some embodiments, the collapsible fill tube may be collapsed to substantially eliminate a volume of the inner lumen which may have a proximal end configured to couple to a inflation port of an inflatable endoluminal prosthesis. In some cases, elongate shaft may include an elongate multi-lumen member which extends from a distal section of the elongate shaft to a proximal section of the elongate shaft, which may have at least a guidewire lumen and the fill lumen and which may include a fill tube cavity in a proximal end thereof configured to accept a section of the collapsible low profile fill tube that has been axially compressed and shortened. In some instances, the fill tube cavity may include a substantially cylindrical cavity having an inner transverse dimension configured to be disposed about the collapsible low profile fill tube in an axially compressed state. For some embodiments, the collapsible low profile fill tube may include a fluoropolymer such as PTFE, which may or may not be sintered, may have a shore hardness of about 25 D to about 40 D, or any combination of these features. In some cases, the elongate shaft may include a guidewire lumen extending from a distal section to a proximal end thereof. In some instances, the elongate shaft may further include a retractable outer sheath that is disposed over the collapsible low profile fill tube and fill lumen of the elongate shaft during delivery of an endoluminal prosthesis to a treatment site and is configured to removably cover a constrained endoluminal prosthesis disposed on the proximal section of the elongate shaft. For some embodiments, the delivery catheter may include a proximal nose cone having a bullet-shaped profile and a shoulder portion with an outer surface which is configured to slidingly accept an inner luminal surface of the outer sheath. In some cases, the collapsible low profile fill tube in a non-collapsed state may have an inner lumen with a nominal transverse dimension of about 0.5 mm to about 5 mm, may have a wall thickness of about 0.02 mm to about 0.13 mm and may have an axial length of about 5 mm to about 100 mm. In some instances, the collapsible low profile fill tube may have a substantially rigid proximal end configured to be releasably coupled to an inflation port of an inflatable endoluminal prosthesis.

Some embodiments are directed to a delivery system for percutaneous delivery of and endoluminal prosthesis including a delivery catheter for delivery of an inflatable endoluminal prosthesis and an inflatable endoluminal prosthesis releasably secured to the proximal section of the elongate shaft in a constrained state. In some embodiments, the prosthesis may include an inflatable portion with an interior volume in fluid communication with an inflation port. A proximal end of the fill tube of the catheter may be releasably coupled to the inflation port in some embodiments. The inflatable endoluminal prosthesis may include an elongate shaft with sufficient column strength for percutaneous advancement within a patient's body lumen. Additionally, the elongate shaft may include a proximal section which may be configured to accept an inflatable endoluminal prosthesis releasably secured thereto in some embodiments. A fill lumen may be in fluid communication with a distal section of the elongate shaft and extend to the proximal section of the elongate shaft in some cases. In some instances, a collapsible low profile fill tube including an inner lumen may be in fluid communication with the fill lumen of the elongate shaft. The collapsible fill tube may be collapsed to substantially eliminate a volume of the inner lumen and may have a proximal end configured to couple to a inflation port of an inflatable endoluminal prosthesis in some embodiments. For some embodiments, the inflatable endoluminal prosthesis may include a tubular body portion with a bifurcated configuration. In some cases, elongate shaft may include an elongate multi-lumen member which extends from a distal section of the elongate shaft to a proximal section of the elongate shaft, which may have at least a guidewire lumen and the fill lumen and which may include a fill tube cavity in a proximal end thereof configured to accept a section of the collapsible low profile fill tube that has been axially compressed and shortened. In some instances, the fill tube cavity may include a substantially cylindrical cavity having an inner transverse dimension configured to be disposed about the collapsible low profile fill tube in an axially compressed state. For some embodiments, the collapsible low profile fill tube may include a fluoropolymer such as PTFE, which may or may not be sintered, may have a shore hardness of about 25 D to about 40 D, or any combination of these features. In some cases, the elongate shaft may include a guidewire lumen extending from a distal section to a proximal end thereof. In some instances, the elongate shaft may further include a retractable outer sheath that is disposed over the collapsible low profile fill tube and fill lumen of the elongate shaft during delivery of an endoluminal prosthesis to a treatment site and is configured to removably cover a constrained endoluminal prosthesis disposed on the proximal section of the elongate shaft. For some embodiments, the delivery catheter may include a proximal nose cone having a bullet-shaped profile and a shoulder portion with an outer surface which is configured to slidingly accept an inner luminal surface of the outer sheath. In some cases, the collapsible low profile fill tube in a non-collapsed state may have an inner lumen with a nominal transverse dimension of about 0.5 mm to about 5 mm, may have a wall thickness of about 0.02 mm to about 0.13 mm and may have an axial length of about 5 mm to about 100 mm. In some instances, the collapsible low profile fill tube may have a substantially rigid proximal end configured to be releasably coupled to an inflation port of an inflatable endoluminal prosthesis.

Some embodiments are directed to a delivery catheter for delivery of an endoluminal prosthesis, including an elongate shaft with sufficient column strength for percutaneous advancement within a patient's body lumen. In some embodiments, the elongate shaft may include a proximal section and a distal section. Additionally, a plurality of releasable belts may be disposed at the proximal section of the elongate shaft which may be configured to releasably constrain at least one self-expanding member of an endoluminal prosthesis in some cases. A first elongate release member may be secured to a distal actuator member at the distal section of the elongate shaft, which may include a proximal section configured to releasably secure at least one respective releasable belt held in a constraining configuration by the first elongate release member. In addition, the first elongate release member may be configured to release with the respective releasable belt upon axial retraction of the release member or release wire in a distal direction by a first actuation length that may be substantially the length the first release member or release wire extends proximally beyond the junction between the first release member and the releasable belt in some embodiments. Additionally, a second elongate release member may be secured to the distal actuator member at the distal section of the elongate shaft, which may include a proximal section configured to releasably secure at least one respective releasable belt held in a constraining configuration by the second elongate release member. In some embodiments, the second elongate release member may be configured to release with the respective releasable belt upon axial retraction of the second elongate release member in a distal direction by a second actuation length that may be substantially the length the second elongate release member extends proximally beyond the junction between the second release member and the respective releasable belt. In some instances, a flexible tether may secure the second elongate release member to the distal actuator. The flexible tether may include an axial slack in its length which may be as long as or longer than the actuation length of the first elongate release member in some embodiments. In some cases, the delivery catheter may also include an elongate release wire sleeve disposed within a lumen extending within the elongate shaft, the elongate release wire sleeve including a low friction material and extending from a distal section of the elongate shaft to a proximal section of the elongate shaft and the elongate release wire sleeve also including a separate lumen for each elongate release member. In some instances, the delivery catheter may be configured to deliver an inflatable endovascular prosthesis wherein the delivery catheter also includes a fill tube having a fill tube lumen extending axially within the elongate shaft. For some embodiments, the elongate shaft may include a guidewire lumen extending from a distal section to a proximal end thereof. In some cases, the elongate shaft may include an elongate multi-lumen member extending from a distal section of the elongate shaft to a proximal section of the elongate shaft. The multi-lumen member may also have a guidewire lumen and a lumen within which the release wire sleeve is disposed. In some instances, the elongate shaft may further include a retractable outer sheath that is configured to removably cover a constrained endoluminal prosthesis disposed on the proximal section of the elongate shaft. For some embodiments, the delivery catheter may also include a proximal nose cone having a bullet-shaped profile and a shoulder portion with an outer surface which is configured to slidingly accept an inner luminal surface of the outer sheath.

Some embodiments are directed to a delivery system for percutaneous delivery of and endoluminal prosthesis, including an elongate shaft with sufficient column strength for percutaneous advancement within a patient's body lumen. In some embodiments, the elongate shaft may include a proximal section, a distal section and a plurality of releasable belts disposed at the proximal section of the elongate shaft which are configured to releasably constrain at least one self-expanding member of an endoluminal prosthesis. A first elongate release member or release wire may be secured to a distal actuator member at the distal section of the elongate shaft, which may include a proximal section configured to releasably secure at least one respective releasable belt held in a constraining configuration by the first elongate release member. In some embodiments, the first elongate release member may be configured to release with the respective releasable belt upon axial retraction of the release member or release wire in a distal direction by a first actuation length that may be substantially the length the first release member extends proximally beyond the junction between the first release member and the releasable belt. In some instances, a second elongate release member may be secured to the distal actuator member at the distal section of the elongate shaft, which may include a proximal section configured to releasably secure at least one respective releasable belt held in a constraining configuration by the second elongate release member and which may be configured to release with the respective releasable belt upon axial retraction of the second elongate release member. In some embodiments, the second elongate release member may be released in a distal direction by a second actuation length that may be substantially the length the second elongate release member extends proximally beyond the junction between the second release member and the respective releasable belt. A flexible tether may secure the second elongate release member to the distal actuator in some embodiments. The flexible tether may include an axial slack in its length which may be as long as or longer than the actuation length of the first elongate release member in some cases. In some embodiments, an endoluminal prosthesis may include a tubular graft body portion of flexible material and at least one self-expanding member secured to a proximal end of the tubular body member. The endoluminal prosthesis may be releasably secured to the proximal section of the elongate shaft by the releasable belts disposed about and releasably constraining at least one self-expanding member of the endoluminal prosthesis in some embodiments. In some cases, the delivery catheter may also include an elongate release wire sleeve disposed within a lumen extending within the elongate shaft, the elongate release wire sleeve including a low friction material and extending from a distal section of the elongate shaft to a proximal section of the elongate shaft and the elongate release wire sleeve also including a separate lumen for each elongate release member. In some instances, the delivery catheter may be configured to deliver an inflatable endovascular prosthesis wherein the delivery catheter also includes a fill tube having a fill tube lumen extending axially within the elongate shaft. For some embodiments, the elongate shaft may include a guidewire lumen extending from a distal section to a proximal end thereof. In some cases, the elongate shaft may include an elongate multi-lumen member extending from a distal section of the elongate shaft to a proximal section of the elongate shaft. The multi-lumen member may also have a guidewire lumen and a lumen within which the release wire sleeve is disposed. In some instances, the elongate shaft may further include a retractable outer sheath that is configured to removably cover a constrained endoluminal prosthesis disposed on the proximal section of the elongate shaft. For some embodiments, the delivery catheter may also include a proximal nose cone having a bullet-shaped profile and a shoulder portion with an outer surface which is configured to slidingly accept an inner luminal surface of the outer sheath.

Some embodiments are directed to a delivery catheter for delivery of an endoluminal prosthesis, including an elongate shaft with sufficient column strength for percutaneous advancement within a patient's body lumen. In some embodiments, the elongate shaft may include a proximal section and a distal section and a plurality of releasable belts disposed on the proximal section of the elongate shaft configured to releasably constrain a self-expanding member of an endoluminal prosthesis. A plurality of elongate release members may include a proximal section configured to releasably secure at least one respective releasable belt while the releasable belt may be in a configuration that constrains at least a portion of an endoluminal prosthesis. In some cases, a release mechanism may be disposed at the distal section of the elongate shaft and in operative connection with the release members. The release mechanism may include a stationary main body portion secured in fixed relation to the elongate shaft and a plurality of rotating actuator rings that may be coupled to at least one elongate release member in some embodiments. The release mechanism may be configured to axially retract the respective at least one elongate release member upon rotation of the respective rotating ring relative to the main body portion in some cases. In some cases, the rotating rings are configured to actuate the respective release members by a camming action. In some instances, each rotating actuator ring may include an axial position on the release mechanism that generally corresponds to an axial position of the releasable belt or belts on the proximal section the rotating actuator ring is configured to actuate. For some embodiments, the delivery catheter may include at least one proximal releasable belt on the proximal section of the elongate shaft configured to releasably constrain a proximal self-expanding member of an endoluminal prosthesis; a proximal rotating actuator ring disposed proximally of the main body portion of the release mechanism, coupled to a proximal elongate release member and configured to release the proximal releasable belt upon actuation; at least one distal releasable belt on the proximal section of the elongate shaft configured to releasably constrain a distal self-expanding member of an endoluminal prosthesis; and a distal rotating actuator ring disposed distally of the main body portion of the release mechanism, coupled to a distal elongate release member and configured to release the distal releasable belt upon actuation. In some cases, the elongate release members may include elongate release wires. In some instances, the delivery catheter may be configured to deliver an inflatable endovascular prosthesis wherein the delivery catheter also includes a fill tube having a fill tube lumen extending axially within the elongate shaft. For some embodiments, the elongate shaft may include a guidewire lumen extending from a distal section to a proximal end thereof. In some cases, the elongate shaft may include an elongate multi-lumen member extending from a distal section of the elongate shaft to a proximal section of the elongate shaft. The multi-lumen member may also have a guidewire lumen and a lumen within which the release wire sleeve is disposed. In some instances, the elongate shaft may further include a retractable outer sheath that is configured to removably cover a constrained endoluminal prosthesis disposed on the proximal section of the elongate shaft. For some embodiments, the delivery catheter may also include a proximal nose cone having a bullet-shaped profile and a shoulder portion with an outer surface which is configured to slidingly accept an inner luminal surface of the outer sheath.

Some embodiments are directed to a delivery catheter for delivery of an endoluminal prosthesis, including an elongate shaft having sufficient column strength for percutaneous advancement within a patient's body lumen. In some embodiments, the elongate shaft may include a proximal section and a distal section and at least one releasable belt disposed on the proximal section of the elongate shaft and configured to releasably constrain a self-expanding member of an endoluminal prosthesis. At least one elongate release member may include a proximal section configured to releasably secure the at least one releasable belt while said releasable belt may be in a configuration that constrains at least a portion of an endoluminal prosthesis. In some cases, a release mechanism may be disposed at the distal section of the elongate shaft in operative connection with the at least one release member. The release mechanism may include a stationary main body portion secured in fixed relation to the elongate shaft and at least one rotating actuator ring which may be coupled to the at least one elongate release member in some embodiments. The release mechanism may be configured to axially retract the at least one elongate release member upon rotation of the rotating ring relative to the main body portion in some cases.

Some embodiments are directed to a delivery system for percutaneous delivery of an endoluminal prosthesis, including an elongate shaft with sufficient column strength for percutaneous advancement within a patient's body lumen. In some embodiments, the elongate shaft may include a proximal section and a distal section and at least one releasable belt disposed on the proximal section of the elongate shaft and configured to releasably constrain a self-expanding member of an endoluminal prosthesis. At least one elongate release member including a proximal section configured to releasably secure the at least one releasable belt while said releasable belt may be in a configuration that constrains at least a portion of an endoluminal prosthesis in some embodiments. A release mechanism may be disposed at the distal section of the elongate shaft in operative connection with the at least one release member in some cases. The release mechanism may include a stationary main body portion secured in fixed relation to the elongate shaft and at least one rotating actuator ring which may be coupled to the at least one elongate release member. In some embodiments, the at least one rotating actuator ring may be configured to axially retract the at least one elongate release member upon rotation of the rotating ring relative to the main body portion. In some cases, an endoluminal prosthesis may include a tubular body portion of flexible material and a self-expanding member secured to a proximal end of the tubular body member. Additionally, the endoluminal prosthesis may be releasably secured to the proximal section of the delivery catheter by the releasable belts disposed about and releasably constraining the self-expanding member of the endoluminal prosthesis in some embodiments. In some cases, the rotating rings are configured to actuate the respective release members by a camming action. In some instances, each rotating actuator ring may include an axial position on the release mechanism that generally corresponds to an axial position of the releasable belt or belts on the proximal section the rotating actuator ring is configured to actuate. For some embodiments, the delivery catheter may include at least one proximal releasable belt on the proximal section of the elongate shaft configured to releasably constrain a proximal self-expanding member of an endoluminal prosthesis; a proximal rotating actuator ring disposed proximally of the main body portion of the release mechanism, coupled to a proximal elongate release member and configured to release the proximal releasable belt upon actuation; at least one distal releasable belt on the proximal section of the elongate shaft configured to releasably constrain a distal self-expanding member of an endoluminal prosthesis; and a distal rotating actuator ring disposed distally of the main body portion of the release mechanism, coupled to a distal elongate release member and configured to release the distal releasable belt upon actuation. In some cases, the elongate release members may include elongate release wires. In some instances, the delivery catheter may be configured to deliver an inflatable endovascular prosthesis wherein the delivery catheter also includes a fill tube having a fill tube lumen extending axially within the elongate shaft. For some embodiments, the elongate shaft may include a guidewire lumen extending from a distal section to a proximal end thereof. In some cases, the elongate shaft may include an elongate multi-lumen member extending from a distal section of the elongate shaft to a proximal section of the elongate shaft. The multi-lumen member may also have a guidewire lumen and a lumen within which the release wire sleeve is disposed. In some instances, the elongate shaft may further include a retractable outer sheath that is configured to removably cover a constrained endoluminal prosthesis disposed on the proximal section of the elongate shaft. For some embodiments, the delivery catheter may also include a proximal nose cone having a bullet-shaped profile and a shoulder portion with an outer surface which is configured to slidingly accept an inner luminal surface of the outer sheath.

Some embodiments are directed to a delivery system for percutaneous delivery of and endoluminal prosthesis, including an elongate shaft having sufficient column strength for percutaneous advancement within a patient's body lumen. In some embodiments, the elongate shaft may include a proximal section, a distal section and a retractable outer sheath extending from the proximal section to the distal section. The retractable outer sheath may be configured to removably cover a constrained endoluminal prosthesis disposed on the proximal section of the elongate shaft in some embodiments. A grip device may be disposed over a distal section of the outer sheath and may include an egg shaped elastomer body in some embodiments. In some cases, the egg shaped elastomer body may include a bore extending axially therethrough. The bore may have an inner transverse dimension configured to slide over an outer surface of the retractable outer sheath and make contact with and frictionally grip the outer surface of the outer retractable sheath when manually squeezed from an outside surface of the grip device in some embodiments. In some cases, the elastomer body of the grip device may include a longitudinal slot communicating with the bore and outside surface of the elastomer body and configured to allow the elastomer body to be spread open for lateral insertion or removal of the outer retractable sheath relative to the bore. In some instances, the elastomer body may include an elastomer having a shore hardness of about 20 A to about 40 A, a material selected from the group consisting of rubber, polyurethane and silicone or any combination of these features. For some embodiments, the elastomer body may include a major outer transverse dimension of about 15 mm to about 50 mm, an axial length of about 500 mm to about 700 mm or both. In some cases, the bore in the elastomer body may be configured to have clearance between an inner surface of the bore and an outer surface of the retractable outer sheath of up to about 2 mm. In some instances, the inner surface of the bore may have a coefficient of friction of about 0.6 to about 0.95.

Some embodiments are directed to a grip device configured to be disposed over a distal section of a retractable outer sheath of a delivery system for delivery of an endoluminal prosthesis. In some embodiments, the grip device may have an egg shaped elastomer body including a bore extending axially therethrough. The bore may have an inner transverse dimension configured to slide over an outer surface of a retractable outer sheath and make contact with and frictionally grip the outer surface of the outer retractable sheath when manually squeezed from an outside surface of the grip device in some embodiments. In some cases, the elastomer body of the grip device may include a longitudinal slot which communicates between the bore and an outside surface of the elastomer body and which is configured to allow the elastomer body to be spread open for lateral insertion or removal of an outer retractable sheath relative to the bore. In some instances, the elastomer body may include an elastomer having a shore hardness of about 20 A to about 40 A, a material selected from the group consisting of rubber, polyurethane and silicone or any combination of these features. For some embodiments, the elastomer body may include a major outer transverse dimension of about 15 mm to about 50 mm, an axial length of about 500 mm to about 700 mm or both. In some cases, the bore in the elastomer body may be configured to have clearance between an inner surface of the bore and an outer surface of the retractable outer sheath of up to about 2 mm. In some instances, the inner surface of the bore may have a coefficient of friction of about 0.6 to about 0.95.

Some embodiments are directed to a method of manually retracting a retractable outer sheath of a delivery system for delivery of an endoluminal prosthesis, including advancing a delivery system for percutaneous delivery of an endoluminal prosthesis to a treatment site within a patient's body lumen. Some methods may include manually grasping the grip device and applying inward radial pressure with the grip such that an inner luminal surface of the bore engages the outer surface of the retractable outer sheath. Additionally, some methods may include manually moving the grip device in an axial direction relative to the elongate shaft of the delivery system while the inner surface of the bore may be engaged with the outer surface of the retractable outer sheath. In some embodiments, the delivery system may include an elongate shaft with sufficient column strength for percutaneous advancement within a patient's body lumen. The elongate shaft may include a proximal section, a distal section and a retractable outer sheath extending from the proximal section to the distal section and configured to removably cover a constrained endoluminal prosthesis disposed on the proximal section of the elongate shaft in some embodiments. Additionally, a grip device may be disposed over a distal section of the outer sheath which may include an egg shaped elastomer body in some embodiments. The egg shaped elastomer body may include a bore extending axially therethrough. In some embodiments, the bore may have an inner transverse dimension configured to slide over an outer surface of the retractable outer sheath and make contact with and frictionally grip the outer surface of the outer retractable sheath when manually squeezed from an outside surface of the grip device. In some cases, the grip device may be axially moved in a distal direction relative to the elongate shaft until an endoluminal prosthesis in a constrained state disposed on a proximal section of the elongate shaft is fully exposed. In some instances, the delivery system may be advanced for percutaneous delivery of an endoluminal prosthesis to the treatment site within the patient's body lumen over a guidewire. For some device embodiments, the grip device may further include a longitudinal slot which communicates between the bore and an outside surface of the elastomer body and which is configured to allow the elastomer body to be spread open for lateral insertion or removal of the outer retractable sheath relative to the bore. In such cases, the method may also include spreading the longitudinal slot in the elastomer body and passing the retractable outer sheath through the longitudinal slot and into the bore.

Certain embodiments are described further in the following description, examples, claims and drawings.

BRIEF DESCRIPTION OF THE DRAWINGS

FIG. 1 illustrates a delivery catheter system embodiment disposed over a guidewire embodiment.

FIG. 1A illustrates the delivery catheter system of FIG. 1 with an outer sheath of the delivery catheter system retracted distally.

FIG. 2 is an elevation view of the delivery catheter system of FIG. 1 illustrating a proximal self-expanding member and fill tube retention mechanism embodiment.

FIG. 3 is an elevation view of a junction between tubular members of the inflation conduit embodiment of the fill tube retention mechanism of FIG. 2 indicated by the encircled portion 3 in FIG. 2.

FIG. 4 is a top view of the junction of FIG. 3 showing the fill tube retention mechanism embodiment at the distal end of the tubular main graft body portion of the endoluminal prosthesis and illustrating a tab, release wire, fill tube, and two fittings.

FIG. 5 is a transverse cross section view of a fitting of FIG. 3 taken along lines 5-5 of FIG. 3 and illustrating an axial lumen for a release wire and a lumen for a fill tube.

FIG. 6 is a transverse cross section view of the distal end of the tubular main graft body portion of the endoluminal prosthesis of FIG. 3 taken along lines 6-6 of FIG. 3.

FIG. 7 is an elevation view of the junction between tubular members of an inflation conduit embodiment of the fill tube retention mechanism of FIG. 2 illustrating retraction of the release wire from the endoluminal prosthesis.

FIG. 8 illustrates retraction of the release wire from the tab and the fittings of the system of FIG. 7.

FIG. 20 is an elevation view of the elongated shaft, distal self-expanding member and graft body of an endoluminal prosthesis embodiment of FIG. 17.

FIG. 21 is an elevation view in partial longitudinal section of the junction between tubular members of the inflation conduit embodiment of FIG. 20 at the encircled portion 21 of FIG. 20, illustrating a tear away portion of the fill tube within the multi-lumen shaft with the distal self-expanding member not shown for purposes of clarity of illustration.

FIG. 22 illustrates a longitudinal section of a fill tube in connection with the inflation port.

FIG. 23 illustrates a longitudinal section of a fill tube within the multi-lumen shaft having storage of excess transitional fill tubing.

FIG. 24 is an elevation view of the proximal stent and the distal self-expanding member of the endoluminal prosthesis of FIG. 17.

FIG. 24A is a transverse cross section view of the prosthesis of FIG. 24 taken along lines 24A-24A of FIG. 24.

FIG. 24B is a transverse cross section view of the prosthesis of FIG. 24 taken along lines 24B-24B of FIG. 24.

FIG. 25 is an elevation view in longitudinal section of a distal adapter embodiment of a delivery system.

FIG. 26 is an elevation view in partial section of a portion of the distal adapter embodiment of FIG. 25 indicated by the encircled portion 26 in FIG. 25.

FIG. 26A illustrates a delivery system embodiment having a distal adapter with distal and proximal release wires and a flexible tether.

FIG. 26B illustrates the delivery catheter system embodiment of FIG. 26A after actuation of the proximal release wires by displacement of the release or actuator cap.

FIG. 26C is a transverse cross sectional view of the elongate shaft of FIG. 26 taken along lines of 26C-26C of FIG. 26 and illustrating a multi-lumen elongate release wire sleeve.

Figure 29:
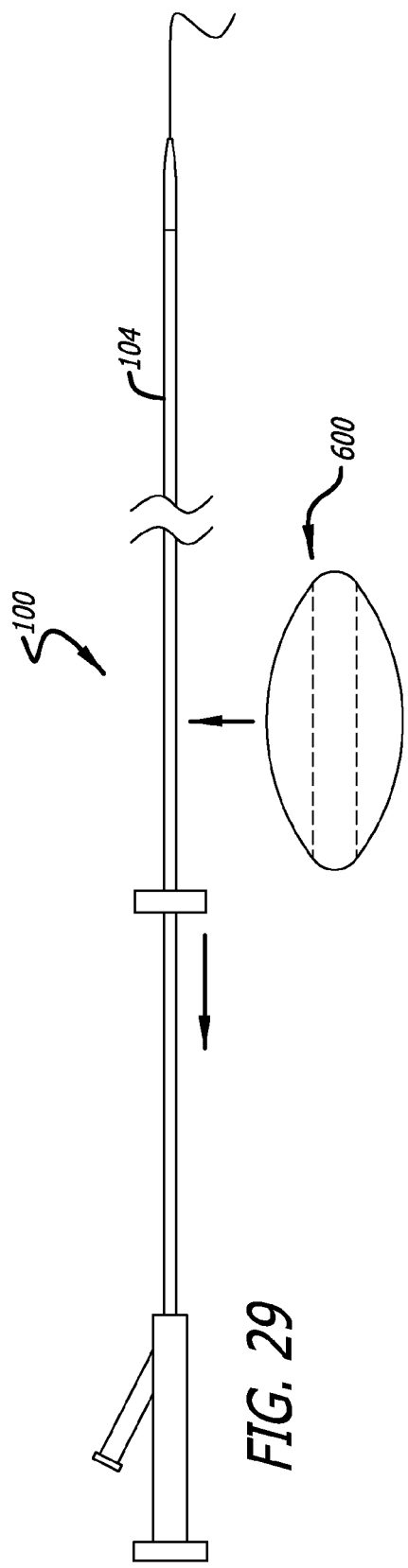

FIG. 29 is an elevation view of a delivery catheter system embodiment disposed over a guidewire embodiment and a gripper device.

Figure 30:
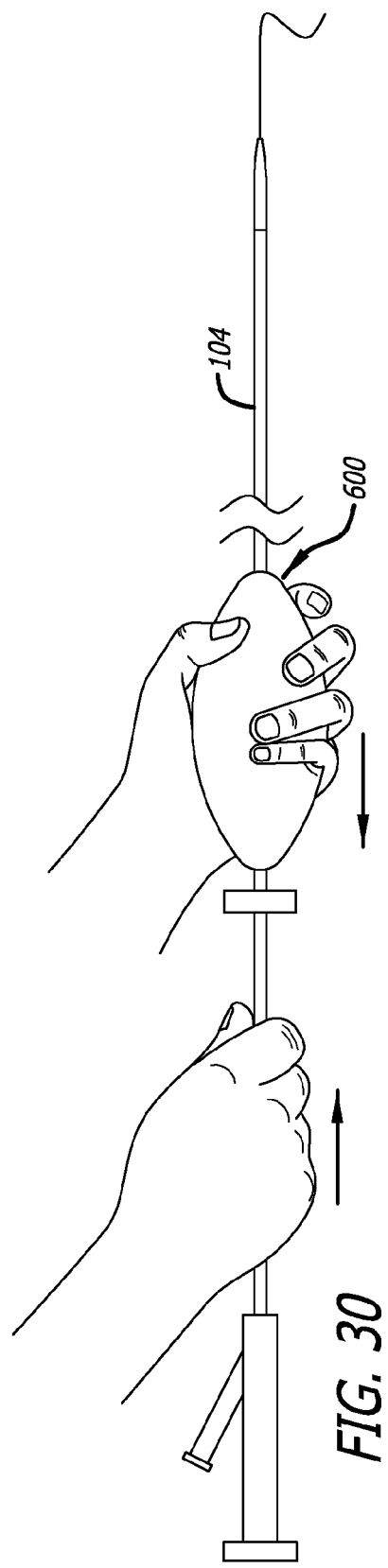

FIG. 30 illustrates the gripper device embodiment of FIG. 29 placed on the delivery catheter system and being actuated by the hands of a user.

FIG. 31 is an elevation view of the gripper device of FIG. 30 disposed over a distal section of the outer sheath of a delivery catheter system embodiment.

FIG. 32 is a transverse cross section view of the gripper device of FIG. 31 taken along lines 32-32 of FIG. 31 illustrating a lumen of the gripper device disposed over and engaging an outer surface of the delivery catheter system.

Figure 33:
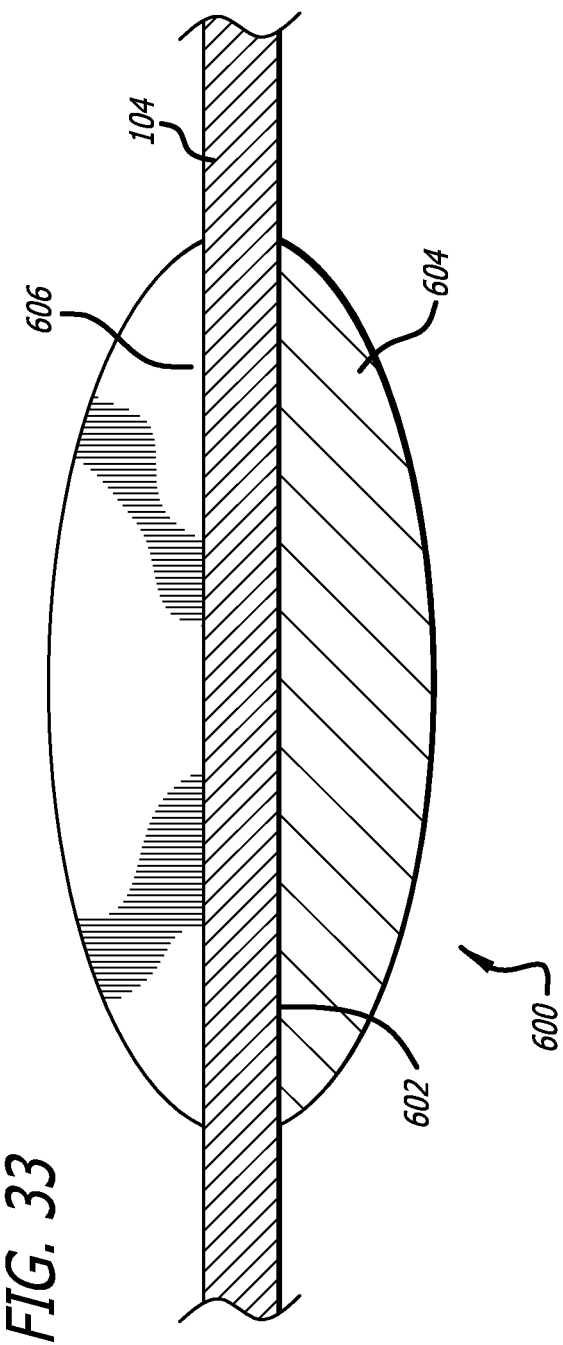

FIG. 33 is an elevation view in partial section of the gripper device of FIG. 31 taken along lines 33-33 of FIG. 31 illustrating the coupling of the gripper device over the outer sheath of the delivery catheter system.

The drawings illustrate embodiments of the invention and are not limiting. For clarity and ease of illustration, the drawings are not made to scale and, in some instances, various aspects may be shown exaggerated or enlarged to facilitate an understanding of particular embodiments.

DETAILED DESCRIPTION

Some embodiments may be directed generally to methods and devices for treatment of fluid flow vessels with the body of a patient. Treatment of blood vessels is specifically indicated for some embodiments, and, more specifically, treatment of aneurysms, such as abdominal aortic aneurysms.

Some embodiments of a modular endovascular graft assembly may include a bifurcated main graft member formed from a supple graft material, such as ePTFE, having a main fluid flow lumen therein. The main graft body member may also include an ipsilateral leg with an ipsilateral fluid flow lumen in communication with the main fluid flow lumen, a contralateral leg with a contralateral fluid flow lumen in communication with the main fluid flow lumen and a network of inflatable channels disposed on the main graft member. For some embodiments, the main graft body member may have an axial length of about 5 cm to about 10 cm, more specifically, about 6 cm to about 8 cm in order to span an aneurysm of a patient's aorta without engaging the patient's iliac arteries directly with the legs of the main graft member.

The inflatable channels of the network of inflatable channels may be disposed on any portion of the main graft body member including the ipsilateral and contralateral legs. The network of inflatable channels may be configured to accept a hardenable fill material to provide structural rigidity to the main graft body member when the network of inflatable channels are in an inflated state and the inflation material has been cured or hardened. Radiopaque inflation material may be used to facilitate monitoring of the fill process and subsequent engagement of graft extensions. The network of inflatable channels may also include at least one inflatable cuff disposed on a proximal portion of the main graft body member which is configured to seal against an inside surface of a patient's vessel, such as the aorta.

A proximal anchor member may be disposed at a proximal end of the main graft member and secured to the main graft body member. The proximal anchor member may have a self-expanding proximal stent portion secured to a distal self-expanding member having struts. Some embodiments of the struts may have a cross sectional area that may be substantially the same as or greater than a cross sectional area of proximal stent portions or distal stent portions adjacent the strut. Such a configuration may be useful in avoiding points of concentrated stress in the proximal anchor member or struts which couple components thereof. For some embodiments, the proximal stent of the proximal anchor member further includes a plurality of barbs having sharp tissue engaging tips that are configured to extend in a radial outward direction in a deployed expanded state. For some embodiments, the proximal anchor member includes a 4 crown proximal stent portion and a 8 crown distal stent portion which may be made from a superelastic alloy such as superelastic NiTi alloy.

At least one ipsilateral graft body extension having a fluid flow lumen disposed therein may be deployed with the fluid flow lumen of the graft body extension sealed to and in fluid communication with the fluid flow lumen of the ipsilateral leg of the main graft body member. In addition, at least one contralateral graft extension having a fluid flow lumen disposed therein may be deployed with the fluid flow lumen of the graft extension sealed to and in fluid communication with the fluid flow lumen of the contralateral leg of the main graft member. For some embodiments, the graft extensions may include an interposed self-expanding member disposed between at least one outer layer and at least one inner layer of supple layers of graft material. The interposed self-expanding member disposed between the outer layer and inner layer of graft material may be formed from an elongate resilient element helically wound with a plurality of longitudinally spaced turns into an open tubular configuration. For some embodiments, the interposed self-expanding member or stent may include a superelastic alloy such as superelastic NiTi alloy. In addition, the graft material of each graft body extension may further include at least one axial zone of low permeability for some embodiments.

For some embodiments, an outside surface of the graft extension may be sealed to an inside surface of the contralateral leg of the main graft when the graft extension is in a deployed state. For some embodiments, the axial length of the ipsilateral and contralateral legs may be sufficient to provide adequate surface area contact with outer surfaces of graft extensions to provide sufficient friction to hold the graft extensions in place. For some embodiments, the ipsilateral and contralateral legs may have an axial length of at least about 2 cm. For some embodiments, the ipsilateral and contralateral legs may have an axial length of about 2 cm to about 6 cm, more specifically, about 3 cm to about 5 cm.

With regard to graft embodiments discussed herein, such as graft assembly 10, and components thereof, as well as graft extensions, the term "proximal" refers to a location towards a patient's heart and the term "distal" refers to a location away from the patient's heart. With regard to delivery system catheters and components thereof discussed herein, the term "proximal" refers to a location that is disposed away from an operator who is using the catheter and the term "distal" refers to a location towards the operator.

Figure 14:
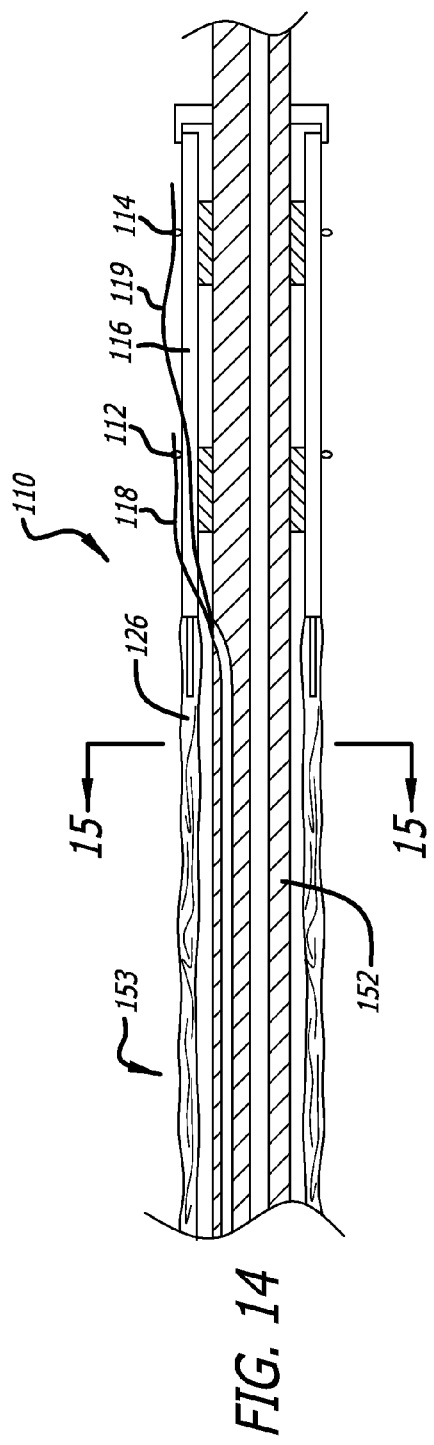
FIG. 14 is an elevation view in longitudinal section of the endoluminal prosthesis embodiment of FIG. 2 indicated by the encircled portion 14 in FIG. 2 illustrating a proximal section of an elongate shaft having multi-lumen configuration and the proximal end of the endoluminal prosthesis.
Figure 15:
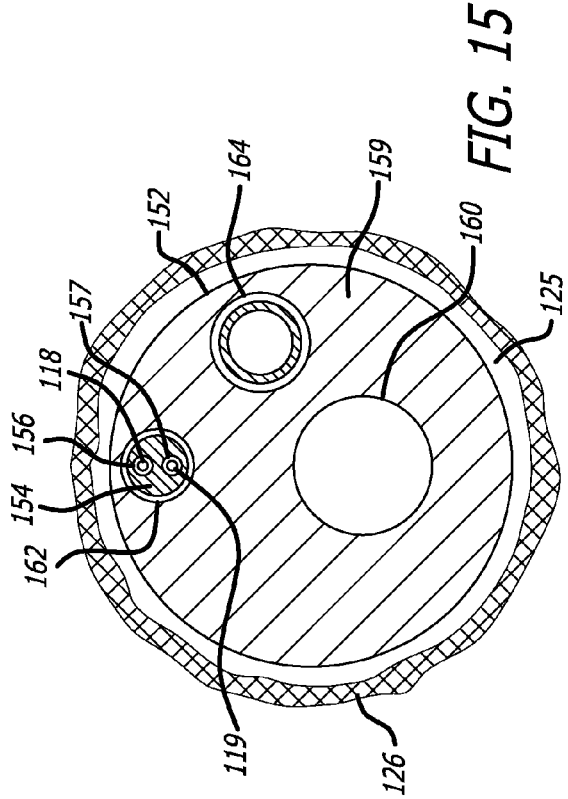
FIG. 15 is a transverse cross sectional view of the endoluminal prosthesis of FIG. 14 taken along lines of 15-15 of FIG. 14 and illustrating the multi-lumen configuration of the proximal section of the elongate shaft.

FIGS. 1-13 show a delivery catheter embodiment 100 having a fill tube retention mechanism for facilitating inflation of an inflatable endoluminal prosthesis or stent graft 110 for treatment of an aortic aneurysm in a patient. FIGS. 14-15 illustrate multi-lumen configuration in a multi-lumen release wire housing embodiment of a delivery catheter system. FIGS. 16-20 illustrate a delivery catheter embodiment structure for deployment of the endoluminal prosthesis assembly. FIGS. 21-23 illustrate a fill tube lumen embodiment. FIGS.

Figure 27:
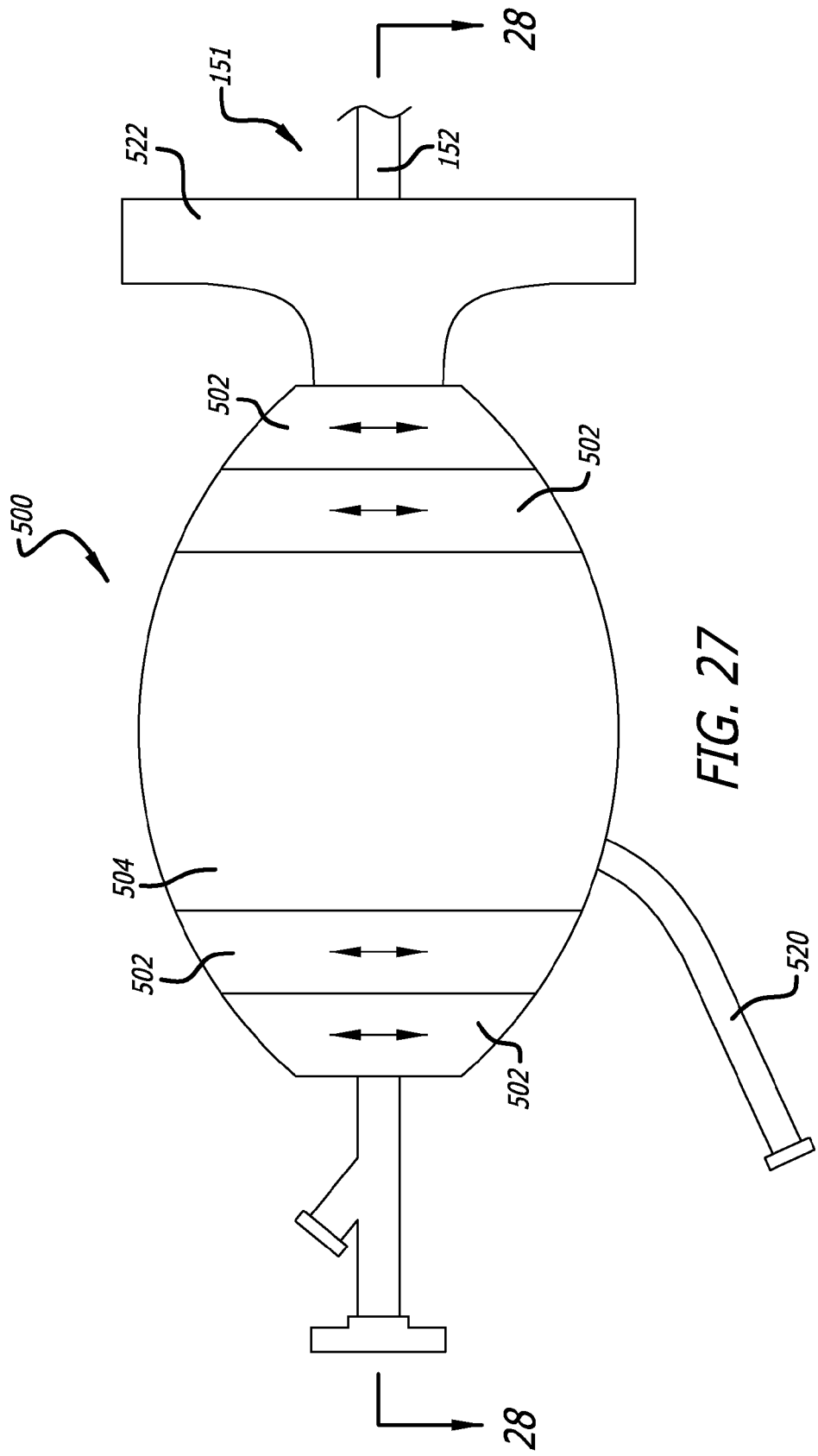
FIG. 27 is an elevation view of a rotating handle distal adapter embodiment of a delivery catheter system.
Figure 28:
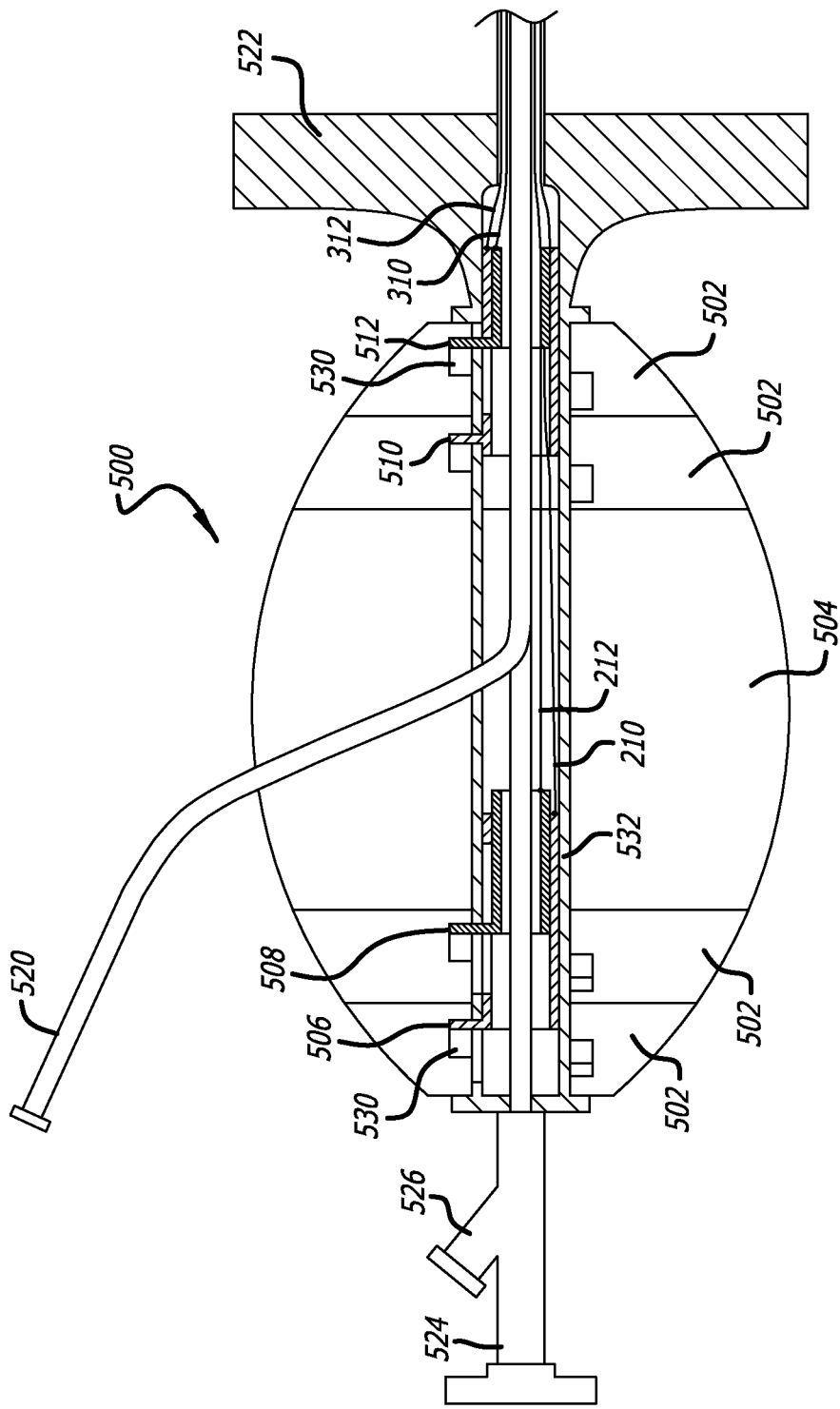
FIG. 28 is an elevation view in a longitudinal section of the rotating handle distal adapter embodiment of FIG. 27 taken along lines 28-28 of FIG. 27 illustrating a rotation actuator for the release wires.

24-26 illustrate an embodiment of multi-stage deployment of an endoluminal prosthesis using proximal and distal release wires. FIGS. 27-28 illustrate a rotating handle distal actuator embodiment which may be used to actuate the proximal and distal release wires of a delivery catheter. FIGS. 29-33 illustrate a grip device embodiment which may attach over a section of an outer sheath of a delivery catheter system in order to improve a user's grip on the delivery catheter system.

Referring again to FIGS. 1-13, the delivery catheter 100 contains an endoluminal prosthesis or stent graft 110 in a radially constrained state and a distal adapter 102. Such a delivery catheter 100 may include some or all of the features, dimensions or materials of delivery systems discussed in commonly owned U.S. Patent Application Publication No. 2004/0138734, published Jul. 15, 2004, filed Oct. 16, 2003, by Chobotov et al., titled "Delivery System and Method for Bifurcated Graft" which is incorporated by reference herein in its entirety and in the PCT International Publication No. WO 02/083038, published Oct. 24, 2002, filed Apr. 11, 2001, by Chobotov et al., titled "Delivery System and Method for Bifurcated Graft" which is incorporated by reference herein in its entirety. FIG. 1A shows the outer sheath 104 of the delivery catheter 100 retracted distally. The endoluminal prosthesis 100, or any other prosthesis discussed herein, may include some or all of the features, dimensions or materials of the prostheses discussed in commonly owned U.S. Patent Publication No. 2009/0099649, filed Oct. 3, 2008, by Chobotov et al., titled Modular Vascular Graft for Low Profile Percutaneous Delivery, which is incorporated by reference herein in its entirety. Once the outer sheath 104 of the delivery catheter 100 is retracted, the endoluminal prosthesis 110 (which may be releasably secured to the delivery catheter 100 with the proximal self-expanding member 116 in a constrained state) may be exposed. The endoluminal prosthesis 110 may be releasably secured to a proximal section of the delivery catheter 100 and may include an inflatable portion with an interior volume in fluid communication with an inflation port 106 and a proximal end of the fill tube 108 of the catheter releasably coupled to the inflation port 106 as shown in FIG. 3. For some embodiments, retraction of the outer sheath 104 from the endoluminal prosthesis 110 may put the endoluminal prosthesis 110 in a partially deployed state.

In FIG. 2, the proximal self-expanding member 116 of the endoluminal prosthesis 110 is shown as being restrained by a first releasable belt member 112 and a second releasable belt member 114 which may be disposed about a proximal section and distal section of the proximal self-expanding member 116. Looped ends of the first belt member 112 may be releasably secured together with a first release wire 118 which may pass through the looped ends of the first belt member 112. Looped ends of the second belt member 114 may be releasably secured together with a second release wire 119 which may pass through the looped ends of the second belt member 114. The first belt member 112 may be released by retraction in a distal direction of the first release wire 118 so as to remove the circumferential constraint of the first belt member 112 about the distal section of the proximal self-expanding member 116. Removal of the circumferential constraint of the first belt member 112 may be used to partially deploy the endoluminal prosthesis 110.

For the particular endoluminal prosthesis 110 and inflation conduit configuration 150 shown in FIG. 3, the distal section of the delivery catheter 100 may have a fill tube 108 extending from the catheter. The fill tube 108 may have a transverse dimension of about 1 mm to about 2 mm. The fill tube 108 may also be configured to be coupled to and in fluid communication with the distal end of the inflation port (fill port) 106. The fill tube 108 may also be uncoupled from the inflation port 106. The fill tube's 108 outer transverse dimension may be configured to slide within an inner lumen 120 of the inflation port 106 and provide a seal there between for viscous fluids.

A tab or flap extension 122 of the graft body of the prosthesis 110 may interlock with one or more fittings 124 of the fill tube assembly which may releasably secure the tubular members of the inflation conduit 150. In FIG. 3, the tab 122 is shown by way of example as protruding from a distal portion of the graft body 126 of the endoluminal prosthesis 110. The graft body 126 may be made from a flexible, collapsible material, such as PTFE, or the like. Additionally, the tab 122 may be made from a flexible, collapsible material, such as PTFE, or the like. The tab 122 may be part of the graft body 126, an extension of the graft body 126, or a separate member secured directly or indirectly to the graft body 126. The tab 122 may have one or more apertures 123 where one or more fittings 124 can be releasably secured. The tab 122 may be located at a substantially fixed relation to the inflation port 106. A fitting 124 may be secured to a proximal portion of the fill tube 108 and may extend laterally from the fill tube 108. The fitting 124 includes at least a portion that may be sized to pass through the aperture 123 in the tab 122, which may be disposed a distance from a proximal end of the fill tube 108 allowing the fill tube 108 to be engaged with the inflation port 106 while the fitting 124 may be disposed within the tab's aperture 123. The aperture 123 of the tab 122 may be configured to fit an outer transverse surface of the fitting 124.

FIG. 4 is a top view of the fill tube 108 retention mechanism embodiment of FIG. 3 illustrating placement of the fill tube 108 underneath the tab extension 122 of the graft body 126 and the tab 122 releasably secured to one of the fittings 124. The fitting 124 may also include one or more apertures/passages 130 for at least one release wire 128 to pass through it longitudinally or along the direction of the delivery catheter 100 in order to mechanically capture a portion of the tab 122 between the release wire 128, fittings 124 and fill tube 108. FIG. 5 shows a transverse cross section view of a fitting 124 of FIG. 3 taken along lines 5-5 of FIG. 3 and illustrates a smaller axial lumen 130 for a release wire 128 and a larger lumen 129 for a fill tube 108. A fitting 124 may also have only one axial lumen for a release wire 128 which may aid in supporting the release wire 128. A plurality of fittings 124 may be used, one or more for engaging the tab 122 and/or one or more for supporting the release wire 128. The axial passage 130 of the fitting 124 may be substantially parallel to the lumen 109 of the fill tube 108. A release wire 128 passes from the delivery catheter 100 through the passage 130 of the fitting 124 to mechanically capture the tab 122 to the fitting 124 with the tab 122 disposed between the release wire 128 and the fill tube 108 and the release wire 128 disposed in the passage 130. The release wire 128 may also extend proximally from the passage 130 of the fitting 124 into a pocket in a portion of the graft body 126 (pocket not illustrated in figures). The release wire 128 may extend from the passage 130 in the fitting 124 to a release mechanism disposed at the distal section of the delivery catheter 100 which may be configured to apply axial tension and displacement to the release wire 128 in order to axially retract the release wire 128 and release the fitting 124 from the aperture 123 of the tab 122.

FIG. 6 shows a transverse cross section view of the inflation conduit 150 at the distal end of the graft body 126 of FIG. 3 taken along lines 6-6 of FIG. 3. The graft body 126 may have a substantially tubular configuration and have a wall portion 127 that bounds a main fluid flow lumen 125 disposed therein. FIG. 6 illustrates an exemplary embodiment of the distal end of the inflation conduit 150. The inflation conduit embodiment 150 may also include an inflation port 106 which may be in fluid communication with an exterior portion of the graft body 126 or may be otherwise disposed at a location or site that is exterior to an interior volume of the inflatable portion of the endoluminal prosthesis 110. The inflation port 106 may be in fluid communication with an inner lumen 158 within the inflation conduit 150 which may be in fluid communication with an outlet port (not shown). Some endoluminal prosthesis 110 may include an optional inflation conduit 150 which may serve as a fill manifold for inflation of an inflatable portion of inflatable embodiments of endoluminal prosthesis 110. Such inflation conduit 150 embodiments may be used to inflate inflatable portions of the endoluminal prosthesis 110 from a desired site or sites within the inflatable portion. Inflation conduit 150 embodiments may include at least one outlet port, disposed at any desired position or desired positions within the inflatable portion of the endoluminal prosthesis 110. The outlet port embodiment may be disposed at a proximal end of the inflation conduit 150. The inflation conduit 150 may have a single outlet port positioned at a desired position within the inflatable portion and may be configured to first fill the inflatable portion of the endoluminal prosthesis from the desired position within an interior volume of the inflatable portion of the endoluminal prosthesis 110.

For some embodiments, the inflatable portion of the endoluminal prosthesis 110 may include one or more inflatable channels formed from the flexible material of the graft body 126 section including the main graft body section and legs (not shown). The inflation conduit 150 may be disposed within an interior volume of a longitudinal inflatable channel 153 (see FIG. 19) of the network of inflatable channels and may be configured to fill the network of inflatable channels from a desired position within an interior volume of a proximal inflatable cuff of the graft body 126 portion of the endoluminal prosthesis 110. The inflation conduit 150 includes a distal end with an inflation port 106 disposed at the distal end.

Figure 19:
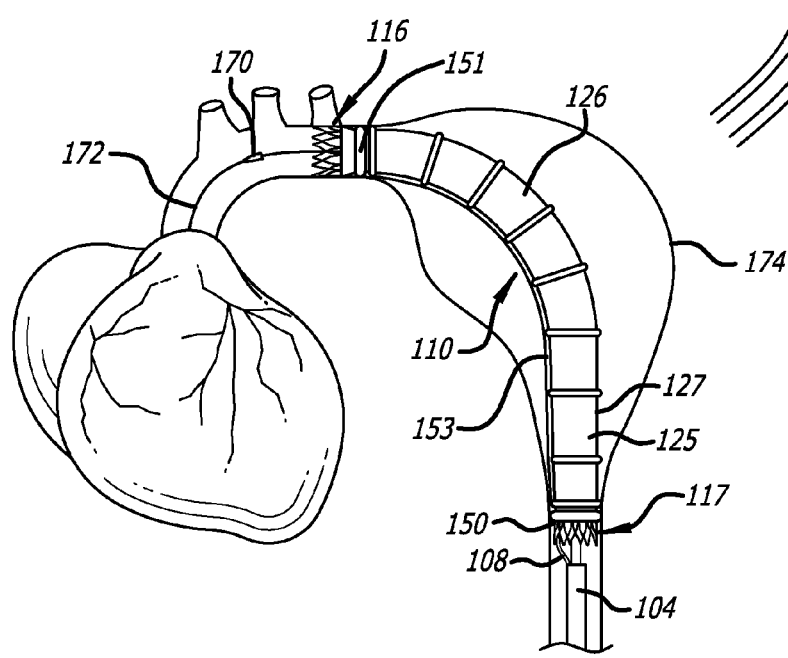
FIG. 19 illustrates the endoluminal prosthesis of FIG. 18 in a deployed state.

When fill material is emitted under pressure from the outlet port of the inflation conduit 150, the fill material may first begin to fill a proximal inflatable cuff 151 (see FIG. 19). This arrangement may allow a seal to be formed between an outside surface of the proximal cuff and a luminal surface of the patient's vasculature at the initial inflation stage. Such a seal may force a flow of blood through the main lumen of the endoluminal prosthesis 110 and allow the graft body 126 of the endoluminal prosthesis 110 to open sequentially in a "windsock" type deployment process. A windsock type deployment process may be useful in some circumstances in order to maintain control of the deployment process of the endoluminal prosthesis 110.

The inflation conduit 150, an inner lumen 158 of which may be in communication between a location outside the inflatable portion of the endoluminal prosthesis 110 and an interior volume of the inflatable portion, may be disposed within any desired portion of the inflatable portion. Inflation conduit 150 embodiments disposed within the interior volume of the inflatable portion may include a variety of configurations with regard to the size or area and position of the outlet port or ports. The inflation conduit 150 may have a single outlet port disposed at the proximal end of the inflation conduit 150. The outlet port may be disposed within the interior volume of the proximal inflatable cuff 151 disposed at the proximal end of the graft body 126 portion. The position of the outlet port may be configured to emit fill material injected into the inflation conduit 150 from the outlet port so as to first inflate the proximal inflatable cuff 151, as discussed above. The inflation conduit 150 may extend distally from the outlet port and may be disposed within the longitudinal inflatable channel 153 of the inflatable portion of the endoluminal prosthesis 110. The longitudinal inflatable channel may extend distally from the proximal inflatable cuff 151.

Some inflation conduit 150 embodiments may be made from a flexible, collapsible material, such as PTFE. For such embodiments, it may be desirable to have an elongate bead, not shown, disposed within an inner lumen 158 of the inflation conduit 150. Such a bead may be made from a flexible but substantially incompressible material, such as a solid PTFE extrusion with or without a radiopaque additive doping (bismuth, barium or other commonly used radiopaque extrusion additives). Bead embodiments may be useful for maintaining a patent lumen passage through the inflation conduit 150 when the endoluminal prosthesis 110 and inflatable portion thereof may be in a constrained state prior to deployment. This configuration may also allow the inflation conduit 150 of the endoluminal prosthesis 110 to be visible under fluoroscopy for orientation purposes throughout the deployment process prior to inflation of the inflatable portion with fill material. A distal end of the bead may be secured at any axial position within the inner lumen of the inflation conduit 150, but may also be secured to a distal portion of the inflation conduit 150.

Figure 9:
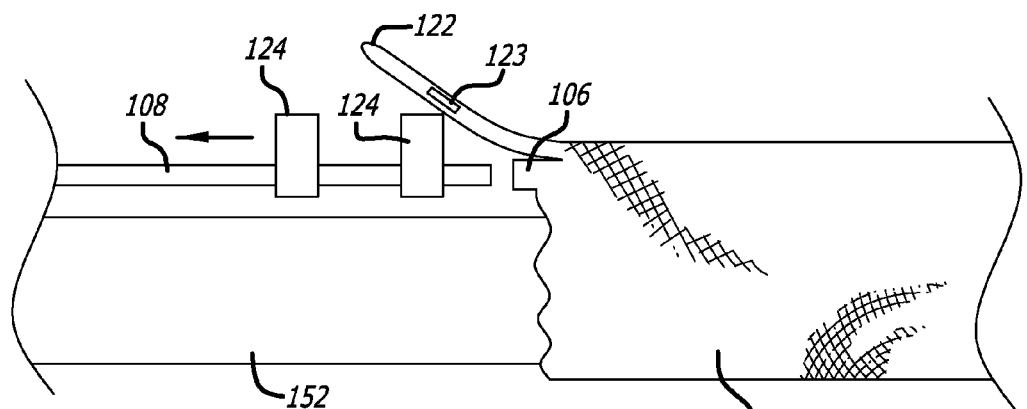
FIG. 9 illustrates retraction of the fill tube from the inflation port of the system of FIG. 7 and retraction of the tab from the fitting.
Figure 10:
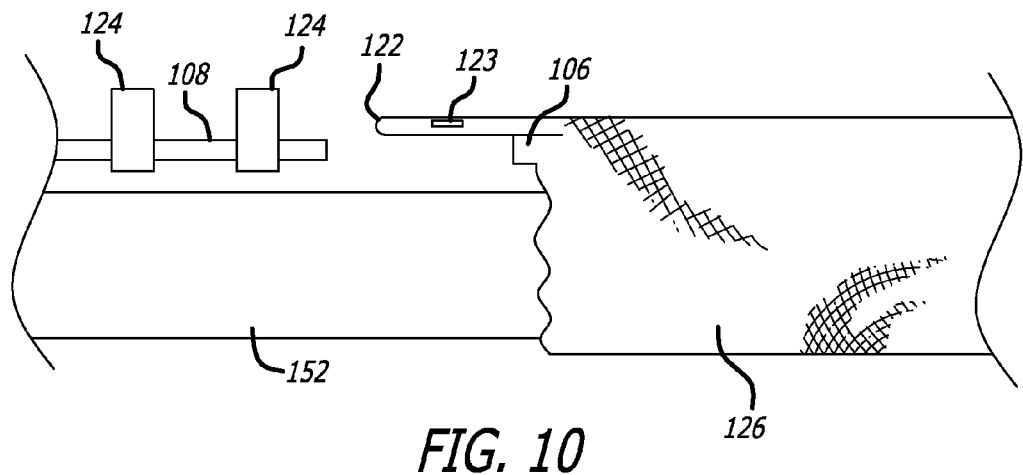
FIG. 10 illustrates distal retraction of the fill tube away from the endoluminal prosthesis and inflation port.
Figure 10A:
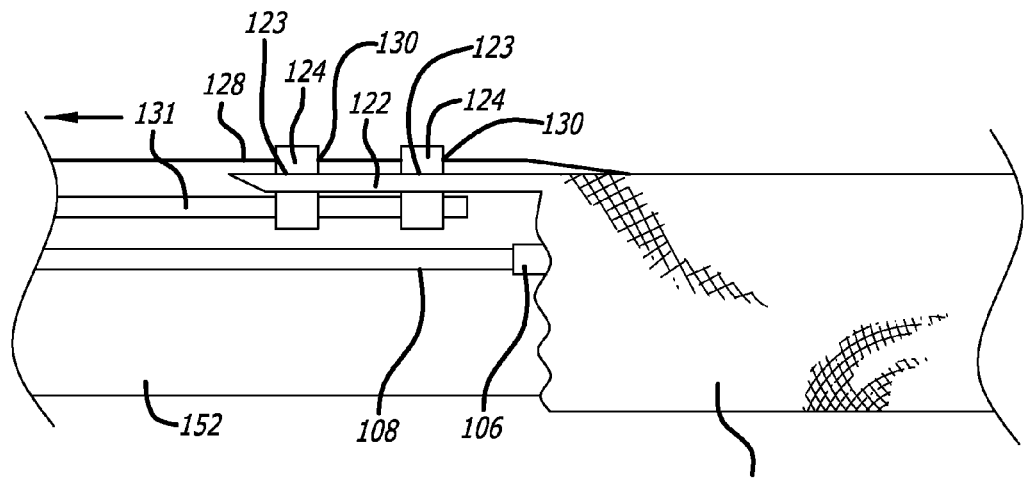
FIG. 10A is an elevation view of the junction between tubular members of an inflation conduit embodiment of the fill tube retention mechanism with fittings extending from an extension member.

FIGS. 7-10A are elevation views of the junction between tubular members of the inflation conduit 150 embodiment of the fill tube retention mechanism of FIG. 2 illustrating the sequence of retraction of the release wire 128 from the graft body 126 followed by retraction from the fittings 124, so as to release the portion of the tab 122 which is mechanically captured by the release wire 128. Once this occurs, detachment may further include retraction of the tab aperture 123 from the fitting 124, and retraction of the fill tube 108 from the inflation port 106. FIG. 7 shows distal movement of the release wire 128 from a pocket (not shown) in the graft body 126 portion. The release wire 128 may extend from the fitting 124 to a distal end of the delivery catheter 100 and may be coupled to a release mechanism disposed at a distal end of the delivery catheter 100 in order to apply axial tension and displacement to the release wire 128. This axial displacement serves to and axially retract the release wire 128 from passage 130 of fittings 124. Thereafter, aperture 123 of the tab 122 of the graft body 126 is free to slide off the fitting 124. The delivery catheter 100 may have one or more release wires 128 for securing the fill tube 108 to the inflation port 106. FIG. 8 shows further distal retraction of the release wire 128 from the fittings 124. FIG. 9 shows an example of the aperture 123 of the tab 122 sliding off and being removed from the fitting 124. Thereafter, the fill tube 108 may be disjoined or otherwise separated from the inflation port 106. FIG. 10 shows an example of distal retraction of the fill tube 108 with fittings 124 from the distal end of the endoluminal prosthesis 110. FIG. 10A illustrates an embodiment of the junction between tubular members of the inflation conduit 150 of the fill tube retention mechanism. In this embodiment, one or more fittings 124 may mechanically couple to and extend from an extension member 131 instead of the fill tube 108. In some cases, the extension member 131 may be secured to the elongate shaft 152 or any other suitable location of the delivery catheter assembly 100. For such an embodiment, the extension member 131 may be axially displaced independent of the fill tube 108 if desired. In addition, for the embodiment shown, each of the multiple fittings 124 passes through a separate respective aperture 123 such that there is mechanical engagement and capture by release wire 128 disposed through passages 130 of a plurality of fittings 124 which are disposed through a plurality of respective apertures 123 in tab 122. Such an arrangement may be desirable in order to provide some redudancy to the retention of the fill tube 108 to the port 106.

Figure 11:
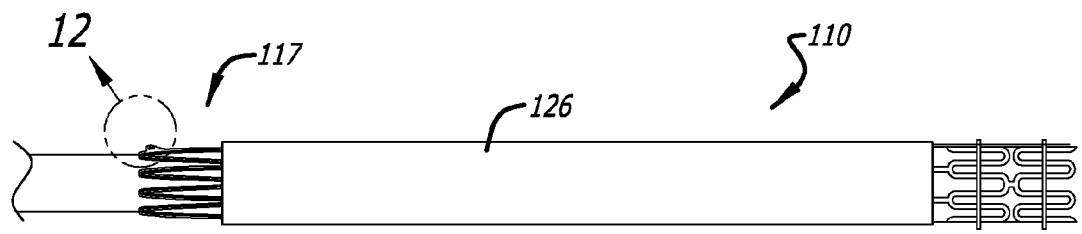
FIG. 11 illustrates a distal self-expanding member and distal portion of a endoluminal prosthesis embodiment.
Figure 12:
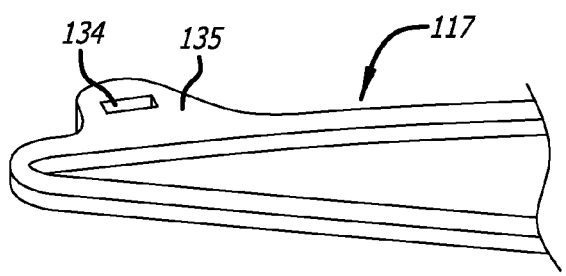
FIG. 12 is an enlarged view of a distal self-expanding member of the device of FIG. 11 illustrating a tab at a distal portion of the distal self-expanding member.
Figure 13:
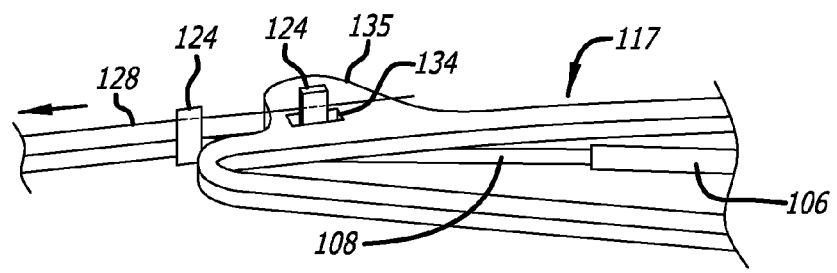
FIG. 13 is an enlarged view of FIG. 11 illustrating a release wire, fill tube, distal self-expanding member tab feature and two fittings.

FIGS. 11-13 show a distal portion of an endoluminal prosthesis 110 embodiment including an aperture 134 that may releasably secure one or more fittings 124. FIG. 12 shows an enlarged view of a distal self-expanding member 117 including an aperture 134 which releasably secures the tubular members of the inflation conduit 150. The distal self-expanding member 117 may include a "tab" feature 135 having an aperture 134. The tab feature 135 of the distal self-expanding member 117 may have one or more apertures 134 to which one or more fittings 124 may be may be mechanically captured or otherwise releasably secured. FIG. 13 shows an embodiment where the tab feature 135 which may be located at a substantially fixed relation to the inflation port 106. A fitting 124 may be secured to a proximal portion of the fill tube 108 and may extend laterally from the fill tube 108. The fitting 124 includes at least a portion that may be sized to pass through the aperture 134 in the tab feature 135, which may be disposed at a distance from a proximal end of the fill tube 108 allowing the fill tube 108 to be engaged with the inflation port 106 while the fitting 124 may be disposed within the tab feature's 135 aperture 134. The aperture 134 of the tab feature 135 may fit an outer transverse surface of the fitting 124. The tab feature 135 may be an extension of a distal self-expanding member 117 of the endoluminal prosthesis 110. The tab feature 135 may be a part of a distal self-expanding member 117 or a separated piece in connection with the distal self-expanding member 117. The distal self-expanding member 117 and tab feature 135 may include or be made from a metal, for example a superelastic alloy such as superelastic NiTi alloy.

FIG. 14 shows a proximal section of an elongated shaft 152 having a multi-lumen configuration and a multi-lumen element configured to house multiple release wires disposed therein. The release wires may be configured to deploy a self-expanding member at a proximal end of the endoluminal prosthesis 110. FIG. 15 shows a transverse cross sectional view of the elongate shaft 152 and endoluminal prosthesis 110 of FIG. 14 illustrating the multi-lumen configuration of the proximal section of the elongated shaft 152. The graft body 126 may be formed from a flexible and supple graft material, such as PTFE, and have a main fluid flow lumen 125 therein. For some embodiments, flexible graft material including PTFE may include expanded PTFE or ePTFE. The delivery catheter 100 may include an elongate shaft 152 with sufficient column strength for percutaneous advancement within a patient's body lumen. The elongate shaft 152 may include a proximal section 153 and at least one lumen extending therein. The first belt 112 and second belt 114 may be configured to releasably constrain the proximal self-expanding member 116 along a proximal section 153 of the elongated shaft 152.

In addition, at least the first release wire 118 and second release wire 119 may extend to and be in communication with a distal end of the elongate shaft 152. The first release wire 118 and second release wire 119 may have a proximal section configured to releasably secure at least one respective releasable belt, such as the first belt 112 and second belt 114, while the releasable belts are in a configuration that constrains at least a portion of the endoluminal prosthesis 110, such as the proximal self-expanding member 116. The elongate shaft 152 may have a multi-lumen elongate release wire sleeve 154 disposed therein which extends within the multi-lumen elongate shaft 152. The elongate release wire sleeve 154 may include or be made from a low friction material and extends from approximately a distal section 151 to a proximal section 153 of the elongate shaft 152. The low friction material may contain a fluoropolymer or a combination thereof, or contain PTFE for example. The PTFE may have a shore hardness of about 40 D to about 70 D. The elongate release wire sleeve 154 may have a separate lumen for each release member, such as a first lumen for the first release wire 118 and a second lumen for the second release wire 119. One or more elongate release members may include or be in connection with an elongate release wire 128.

The elongate shaft 152 may have a multi-lumen configuration, wherein one or more lumens are within the elongate shaft lumen 159. The elongate shaft lumen 159 may contain an elongate multi-lumen member which extends from a distal section 151 of the elongate shaft 152 to a proximal section 153 of the elongate shaft 152 (see also FIG. 16). The multi-lumen member embodiment of the elongate shaft 152 may contain a guidewire lumen 160 and a release wire lumen 162 within which the multi-lumen release wire sleeve 154 may be disposed. The elongate shaft lumen 152 may also contain a fill tube lumen 164 which may extend axially. The guidewire lumen 160 may extend from a distal section 151 to a proximal section 153 thereof. The release wire lumen 162 may have one or more release wire sleeves 154 disposed within. For example, for a thoracic endoluminal prosthesis two release wire sleeves 154 or a duel lumen may be disposed within the release wire lumen 162. For an abdominal endoluminal prosthesis three release wire sleeves 154 or a tri-lumen may be disposed within the release wire lumen 162. A retractable outer sheath 104 may be disposed over the elongate shaft 152 and the elongate release wire sleeve 154 and may be configured to removably cover a constrained endoluminal prosthesis 110 disposed on the proximal section 153 of the elongate shaft 152. The delivery catheter 100 may also include a proximal nosecone 170 which may have a bullet-shaped profile and a shoulder portion having an outer surface which may be configured to slidingly accept an inner luminal surface of the retractable outer sheath 104.

Figure 16:
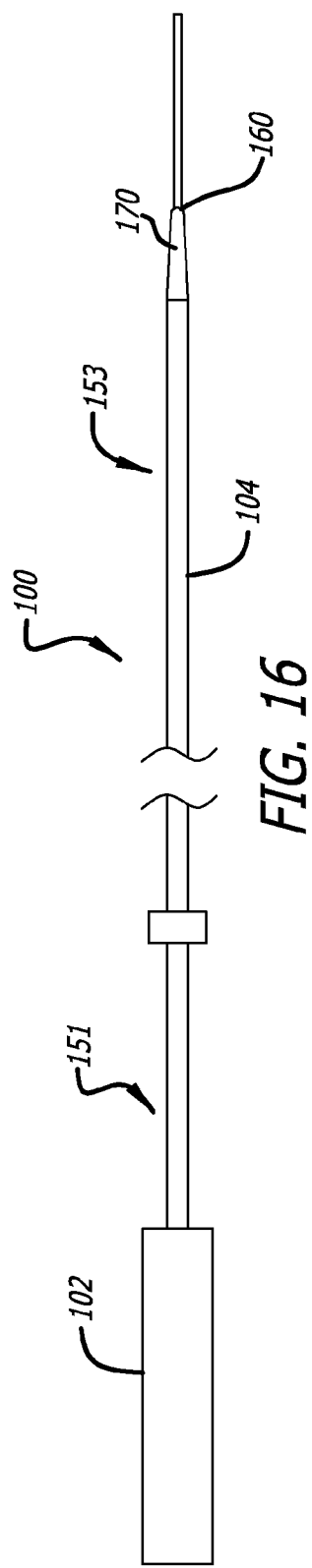
FIG. 16 illustrates a delivery catheter system embodiment disposed over a guidewire embodiment.
Figure 17:
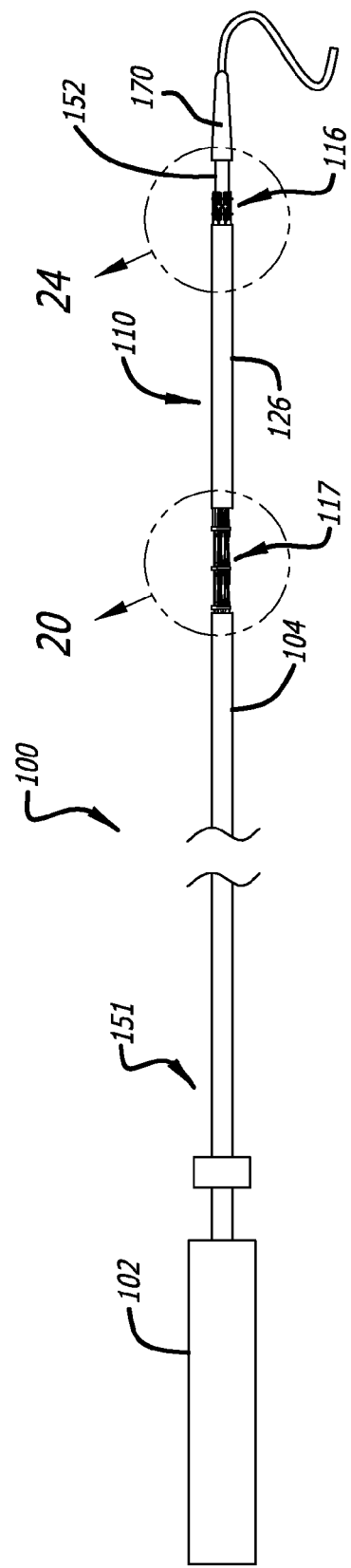
FIG. 17 illustrates the delivery system of FIG. 16 with an outer sheath of the delivery catheter system retracted distally exposing an endoluminal prosthesis embodiment.
Figure 18:
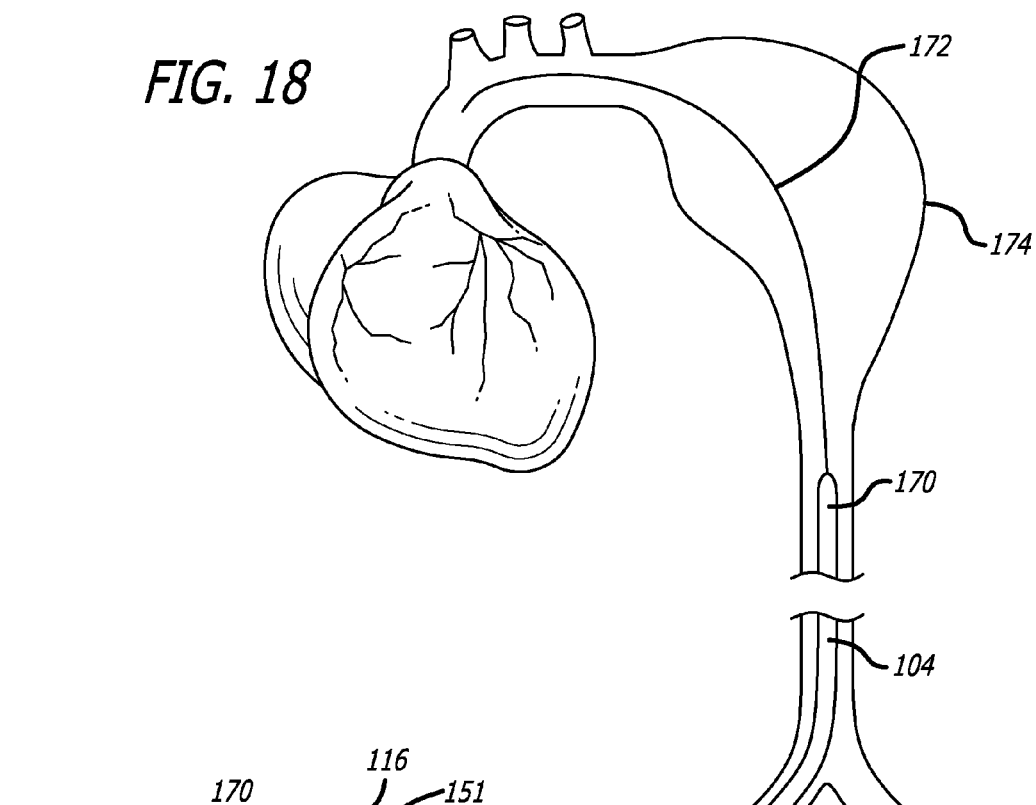
FIG. 18 illustrates a delivery catheter system embodiment disposed over a guidewire embodiment within a patient's thoracic aorta and crossing a thoracic aortic aneurysm.

FIGS. 16-19 show structures and the delivery system for a thoracic endoluminal prosthesis. FIG. 16 shows a delivery catheter 100 embodiment including a guidewire lumen 160. An elongate shaft 152 and proximal nosecone 170 are also shown. FIG. 17 shows the delivery catheter 100 with the outer sheath 104 retracted distally and exposing an endoluminal prosthesis 110 embodiment. A distal self-expanding member 117, graft body 126 and proximal self-expanding member 116 are also shown. FIG. 18 shows the delivery catheter 100 system within a patient's thoracic aorta with the guidewire 172 crossing through the thoracic aortic aneurysm 174. FIG. 19 shows a completely deployed thoracic aortic aneurysm endoluminal prosthesis 110 within a patient's body, where the proximal nosecone 170 may be proximal to the endoluminal prosthesis 110 and the fill tube 108 may be releasably secured to the inflation conduit 150. The endoluminal prosthesis 110 includes graft body 126 which has a wall portion 127 that bounds a main fluid flow lumen 125 disposed therein.

The graft body 126 has a tubular body portion which generally may have a large transverse dimension and area. The graft body 126 may be made of a flexible material and has at least one proximal self-expanding member 116 secured to a proximal end of the tubular graft body 126 member. In addition, a proximal anchor member may also be disposed at a proximal end of the graft body 126. The proximal anchor member may include an additional proximal self-expanding member 116 that may be formed from at least one elongate element having a generally serpentine shape with, for example, four crowns or apices at either end. Each proximal apex or crown of the proximal self-expanding member 116 may be coupled to alternating distal crowns or apices of an additional 8 crown proximal self-expanding member 116. The distal end of the proximal self-expanding member 116 adjacent the graft body 126 may be formed from an elongate element having a generally serpentine shape. Additionally, the distal end of the proximal self-expanding member 116 adjacent the graft body 126 may be mechanically coupled to a connector ring (not shown) which may be embedded in the graft body 126 material approximately at the proximal end of the graft body 126, or directly coupled to perforations in the proximal edge region of the graft body 126. Embodiments of the connector ring may be generally circular in shape and may have regular undulations about the circumference that may be substantially sinusoidal in shape.

The proximal self-expanding member 116 may include outwardly extending barbs (not shown), that may be integrally formed with the struts and may have sharp tissue penetrating tips configured to penetrate into tissue of an inside surface of a lumen within which the proximal self-expanding member 116 may be deployed in an expanded state. Although the anchor members may include proximal and distal self-expanding members 116 and 117, similar expanding members may be used that are configured to be inelastically expanded with outward radial pressure as might be generated by the expansion of an expandable balloon from within either or both proximal and distal self-expanding members 116 and 117. The connector ring coupled to the proximal self-expanding member 116 may also be inelastically expandable.

The distal anchor member shown in FIG. 19 includes a single distal self-expanding member 117 disposed at the distal end of the tubular graft body 126 of the endoluminal prosthesis 110. The distal self-expanding member 117 may be formed from a resilient elongate element having a generally serpentine shape with eight crowns or apices at either end. A proximal end of the distal self-expanding stent member 117 may be mechanically coupled to a connector ring which may be embedded in graft body 126 material of the distal end of the graft body 126, or directly coupled to perforations in the distal edge region of the graft body 126.

A collapsible low profile fill tube 108 embodiment may aid in reducing space within the delivery catheter 100 while in a constrained or collapsed state such as during packaging and transportation of the endoluminal prosthesis 110 to a treatment facility. FIGS. 20-23 shows a portion of the endoluminal prosthesis 110 embodiment with the fill tube lumen 164 of the elongate shaft 152 and the fill tube 108 releasably secured to the inflation port 106. FIG. 20 shows the elongate shaft 152, distal self-expanding member 117, and graft body 126. FIG. 21 shows a partial longitudinal section of the junction between tubular members of the inflation conduit 150 with a tear away portion of the fill tube 108 which may be defined by a tear-away line 107 (distal self-expanding member 117 not shown). The fill lumen 164 may be part of the multi-lumen elongate shaft 152 that houses or partially houses the catheter fill tube 178 or fill tube 108. The collapsible low profile fill tube 108 may be a flexible transition tube between the elongate shaft 152 and the inflation port 106. The fill tube 108 may be comprised of a fluoropolymer, PTFE, ePTFE or combinations thereof. The PTFE of the collapsible low profile fill tube 108 may be made out of a material having a shore hardness of about 25 D to about 40 D. The PTFE of the collapsible low profile fill tube may be made out of a sintered PTFE. The fill tube lumen 109 of the collapsible low profile fill tube 108 in a non-collapsed state may have a nominal transverse dimension of about 0.5 mm to about 5 mm. The collapsible low profile fill tube 108 may have an axial length of about 5 mm to about 100 mm. Additionally, the wall thickness of the collapsible low profile fill tube may be about 0.02 mm to about 0.13 mm.

Within the elongate shaft 152, the fill tube lumen 164 contains a catheter fill tube 178 for fill material to be injected into the proximal end of the delivery catheter 100 system. The catheter fill tube 178 may be a rigid tube that may contain nylon, polyimide, PTFE or similar material or combinations thereof. The fill tube 108 may have a larger transverse radius than the catheter fill tube 178, thus permitting the fill tube 108 to slide over or couple to the catheter fill tube 178 to form a continuous tube such that the fill material may be injected or pushed through the catheter fill tube 178 and into the fill tube 108. FIG. 22 shows the inflation port 106 having a larger transverse radius than the fill tube 108, permitting the inflation port 106 to slide over or couple to the fill tube 108 such that the fill material may be injected or pushed through the fill tube 108 and into the inflation port 106. The collapsible low profile fill tube 108 may have a substantially rigid proximal end 180 configured to be releasably coupled to an inflation port 106 of an inflatable graft body 126. The inflation port 106 may have a substantially rigid distal end 182 configured to be releasably coupled to a fill tube 108.

FIG. 23 shows the elongated shaft 152 having a larger lumen for storage of excess transitional fill tubing 108. As the delivery catheter 100 may be moved up a patient's body into place for deployment of the endoluminal prosthesis 110, the flexible fill tube 108 may be stored within the multi-lumen elongate shaft 152. After the fill tube 108 may be retracted from disjoining from the inflation port 106, the flexible fill tube 108 may be stored within the multi-lumen elongate shaft 152. The multi-lumen elongate shaft 152 may have a fill tube cavity 165 at the proximal end thereof which may be configured to accept a section of the collapsible low profile fill tube 108 that has been axially compressed and shortened. The fill tube cavity 165 may have a substantially cylindrical cavity having an inner transverse dimension configured to be disposed about the collapsible low profile fill tube 108 in an axially compressed state. The elongate shaft 152 may have a retractable outer sheath 104 that may be disposed over the collapsible low profile fill tube 108 and fill tube lumen 164 of the elongate shaft 152 during delivery of the endoluminal prosthesis 110 to a treatment site. The retractable outer sheath 104 may be configured to removably cover a constrained endoluminal prosthesis 110 disposed on the proximal section 153 of the elongate shaft 152.

In some embodiments of the delivery catheter 100 and endoluminal prosthesis 110, there may be a multi-stage deployment embodiment of release wires that constrain the proximal and distal self-expanding members 116 and 117 of an endoluminal prosthesis 110. The multi-deployment embodiment involves multiple release wires with one belt being released at a time such that the anchor member or self-expanding member release forces are reduced. Anchor member or self-expanding member release forces may be compounded due to the anatomical path an endoluminal prosthesis 110 and delivery catheter 100 system navigate through. Reduction of the friction and load along the delivery pathway may be done by incorporating a low friction surface or lumen around each release wire. Catheter element embodiments having a multi-lumen configuration, such as dual lumens or tri-lumens may provide low frictional surfaces and separate lumens for each of the release wires to reduce stent release forces. FIG. 24 shows the proximal stent 116 and distal stent 117 with proximal belt members 204, 206 and 208, proximal release wires 210 and 212, distal belt members 304, 306 and 308, and distal release wires 310 and 312. FIG. 24A shows a guidewire lumen 160, a collapsed proximal self-expanding member 116 disposed around the guidewire lumen 160, and a proximal release wire 212. FIG. 24B shows a guidewire lumen 160, inflation conduit 150, a collapsed distal stent 117 around the guidewire lumen 160 and inflation conduit 150, and the axial release wire 312.

FIG. 25 shows a distal section of an elongate shaft embodiment 152 and distal actuator embodiment 400. FIG. 26 shows a schematic representation of the distal actuator 400 which houses the distal termination of the proximal release wires 210 and 212, distal release wires 310 and 312, release wire lumen 436, release wire sleeves 428, guidewire lumen 160, and multi-lumen elongate shaft 152. In the embodiments shown, the distal end of each release wire 210, 212, 310 and 312 may be secured to a respective actuator device such as an actuator cap of the actuator 400. Such actuator caps may have a nested configuration with respect to each other. In particular, the distal end of release wire 210 is secured to actuator cap 211, the distal ends of release wires 212 and 312 are each secured, either directly or indirectly, to actuator cap 213, and release wire 310 is secured to actuator cap 311. The distal end of release wire 312 is indirectly secured to actuator cap 213 by a flexible tether 402 which may have a length sufficient for release wire 212 to be fully or partially actuated by actuation of actuator cap 213 before release wire 312 is actuated. Also, the nesting of the actuator caps 211, 213 and 311 may be configured such that the order of the release wire actuation is controlled by the configuration. For example, in some cases, actuator cap 311 can not be actuated until actuator cap 213 is actuated and actuator cap 213 can not be actuated until actuator cap 211 is actuated.

FIG. 26C shows a cross section view of the elongate shaft 152 of FIG. 26 illustrating a multi-lumen elongate release wire sleeve 154 with release wires 210, 212, 310 and 312 extending through the multiple release wire lumens of the release wire sleeve 154 with each release wire having a separate lumen in the sleeve 154. The release wires 210, 212, 310, and 312, also called elongate release members, may include a proximal section configured to releasably secure at least one respective releasable belt, such as proximal belt members 204, 206 and 208, and distal belt members 304, 306 and 308. In the proximal section of the delivery catheter 100, the proximal and distal release wires 210, 212, 310 and 312 may be configured to constrain the releasable belts 204, 206, 208, 304, 306 and 308. The releasable belts constrain at least one of the proximal or distal self-expanding members 116, 117. The first proximal release wire 210 may be configured to release its respective releasable belts 204 and 206 upon axial retraction of the proximal release wire 210 in a distal direction by a first actuation length that may be substantially the length the proximal release wire 210 extends proximally beyond the junction between the proximal release wire 210 and the releasable belts 204 and 206. The second proximal release member 212 may be configured to release its respective release belt 208 upon axial retraction of the second proximal release member 212 in a distal direction by a second actuation length 309 that may be substantially the length the second proximal release member 212 extends proximally beyond the junction between the proximal release member 212 and its respective release belt 208. As discussed above, a flexible tether 402 may secure the distal release member or wire 312 to an actuator cap 213 of the distal actuator 400. The flexible tether 402 includes an axial slack in its length which may be as long as or longer than the actuation length of the distal release member 312. As such, actuation of actuator cap 213 will first actuate release wire 212 and thereafter actuate release wire 312. FIGS. 26A and 26B illustrate the actuation of the proximal release wire 212 and the distal release wire 312 with the flexible tether 402

A rotating handle embodiment 500 of a distal adapter 102 of a delivery catheter 100 system is shown in FIG. 27. FIG. 28 is a longitudinal section of the rotating handle embodiment 500. The rotating handle embodiment 500 may be a release mechanism disposed at the distal section 151 of the elongate shaft 152 which may be in operative connection with the proximal and distal release wires 210, 212 and 310, 312. The rotating handle 500 may enable deployment of the proximal self-expanding member 116 or distal self-expanding member 117, allowing the user to choose either self-expanding member 116, 117 to deploy for accuracy. The rotating handle embodiment 500 may have four interlocked rings 502 on the handle 504 which may control the actuation of their respective belts: proximal outer stent belt ring 506, proximal inner stent belt ring 508, distal inner stent belt ring 510 and distal outer stent belt ring 512. The handle 504 may be stationary and secured in fixed relation to the elongate shaft 152. The rotating actuator rings 502 may be coupled to the proximal and distal release wires 210, 212 and 310, 312 and configured to axially retract the respective proximal and distal release wires 210, 212 and 310, 312 upon rotation of the respective rotating ring 502 relative to the handle 504. The proximal outer stent belt ring 506 and proximal inner stent belt ring 508 may be interlocked together between the rotating rings 502. Additionally, the distal inner stent belt ring 510 and the distal outer stent belt ring 512 may be interlocked together between the rings 502. The interlocking of the belt rings can prevent accidental release of the outer belts before the inner belt rings are released. The rotating rings actuate their respective release members by a camming action. Each rotating actuator belt ring includes an axial position on the release mechanism that generally corresponds to an axial position of the releasable belt or belts on the proximal section of the rotating actuator ring may be configured to actuate.

The rotating handle embodiment 500 may also have a fill polymer port 520, a grip 522, and a guide wire hemostatic valve 524 with a flush 526. The one or more rings 502 may rotate to pull the stent release wires 210, 212 and 310, 312 generally only in one direction relative to the handle embodiment 500. The release wires 210, 212 and 310, 312 may be spring loaded with a wire/ring released spring. Each ring 502 may have a cam 530 feature with a swaged end on the associated release wire. The ring 502 may have threaded components, such as a threaded shaft 532, that translate rotation into axial release wire 210, 212 and 310, 312 movement. The handle embodiment 500 design may incorporate a short throw concept where the release wire 210, 212 and 310, 312 ends may be released within up to about 5 cm of the belt. The handle embodiment 500 may be constructed in a variety of methods, for example, six or more pieces of the handle embodiment 500 may rotate relative to the handle 504 and control the actuation of any number of release wires. The pieces may include a threaded shaft 532, two or more cams 530, and the four rings 502.

A grip embodiment 600 may aid a physician in retracting the outer sheath 104 of a delivery catheter 100 system. During the endovascular procedure, retraction of the sheath 104 may be difficult due to the impacted forces of the delivery catheter 100 and slippery conditions during the procedure. The grip embodiment 600 may aid a physician in gripping and holding onto the delivery catheter 100. FIG. 29 illustrates an embodiment of the gripper device 600. FIG. 30 shows the gripper device placed on the delivery catheter 100 system. The grip 600 may have a textured, easy-to-grip surface and may be made of material that provides a collapsible grip, such as silicone, for example. The inner surface 602 of the grip 600 or its bore may be greater than a tubular member to which the grip 600 may releasably couple to, such as the elongate shaft 152. Furthermore, the inner surface 602 of the grip 600 may be sized such that the grip 600 may be movable relative to the, for example, elongate shaft 152 or retractable outer sheath 104, unless the grip 600 is squeezed. The inner surface 602 of the bore extends axially through the grip 600 with an inner transverse dimension configured to slide over an outer surface of the retractable outer sheath 104 and make contact with and frictionally grip the outer surface of the outer retractable sheath 104 when manually squeezed from an outside surface 604 of the grip 600.

The inner surface 602 of the bore may be configured to have clearance between an inner surface 602 of the bore and an outer surface of the retractable outer sheath 104 of up to about 2 mm. Additionally, in some cases, the inner surface 602 of the bore may be configured to have no clearance between an inner surface 602 of the bore and an outer surface of the retractable outer sheath 104. The inner surface 602 of the bore may have a coefficient of friction of about 0.6 to about 0.95. The grip 600 may have an optional axial slit or longitudinal slot 606 in communication with the inner surface 602 of the bore which allows easy placement onto and removal from the delivery catheter 100. The longitudinal slot 606 may be spread in order to allow the grip 600 to be placed over a part of the delivery catheter 100 for lateral insertion or removal of the outer retractable sheath 104 relative to the inner surface 602 of the bore. FIG. 31 is an elevation view in longitudinal section of the grip 600 of FIG. 30 disposed over a distal section of the outer sheath 104 of the delivery catheter 100 system. The grip 600 may have an egg shaped elastomer body. The elastomer body may have a shore hardness of about 20 A to about 40 A. The elastomer body may have material selected from the group consisting of rubber, polyurethane, silicone and combinations thereof. The elastomer body may have a major outer transverse dimension of about 15 mm to about 50 mm. The elastomer body may have an axial length of about 500 mm to about 700 mm. FIG. 32 is a transverse cross section view of the grip 600 of FIG. 31 taken along lines 32-32 of FIG. 31 and illustrates the inner surface 602 of the bore of the grip 600. FIG. 33 is a transverse cross section view of the grip 600 of FIG. 31 taken along lines 33-33 of FIG. 31 and illustrates coupling of the inner surface 602 of the bore to the outer sheath 104.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the embodiments discussed. Although embodiments have been described in substantial detail with reference to one or more specific embodiments, those of ordinary skill in the art will recognize that changes may be made to the embodiments specifically disclosed in this application, yet these modifications and improvements are within the scope and spirit of the disclosure.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

Certain embodiments are set forth in the claim(s) that follow(s).

What is claimed is:

1. A delivery system for an inflatable endoluminal prosthesis, comprising:
   a delivery catheter comprising an elongate shaft including a proximal section and a fill tube, the fill tube including a fill tube lumen extending axially therein;
   an endoluminal prosthesis releasably secured to the proximal section of the delivery catheter, the endoluminal prosthesis including an inflatable portion having an interior volume in fluid communication with an inflation port, wherein a proximal end of the fill tube is releasably coupled to the inflation port; and
   a fill tube retention mechanism that releasably secures the fill tube lumen in fluid communication to the inflation port, comprising:
   a tab disposed at a distal end of the endoluminal prosthesis in a substantially fixed relation to the inflation port and which includes an aperture that is separated from the inflation port by a predetermined distance,
   a fitting secured to a proximal portion of the fill tube and which extends laterally from the fill tube, at least a portion of the fitting being sized to pass through the aperture such that the aperture closely fits an outer transverse surface of the fitting, the fitting being disposed a distance from a proximal end of the fill tube such that the fill tube may be engaged with the inflation port while the fitting is disposed within the aperture, the fitting having a passage therethrough, and a release wire having an outer transverse dimension and axial bending stiffness that allows the release wire to pass through the passage and mechanically capture the tab to the fitting such that a portion of the tab is disposed between the release wire and the fill tube, and wherein the release wire may be retracted from the passage to release the portion of the tab.

2. The delivery system of claim 1 wherein the passage comprises an axial passage that is substantially parallel to the fill tube lumen.

3. The delivery system of claim 2 wherein the release wire extends proximally from the passage into a pocket in a body portion of the endoluminal prosthesis.

4. The delivery system of claim 1 wherein the release wire extends from the passage to a release mechanism disposed at a distal section of the delivery catheter, the release mechanism being configured to apply axial tension and displacement to the release wire in order to axially retract the release wire and release the fitting from the aperture.

5. The delivery system of claim 1 wherein the fill tube comprises a plurality of fittings and the tab comprises a plurality of corresponding apertures.

6. The delivery system of claim 1 wherein a body portion of the endoluminal prosthesis comprises PTFE.

7. The delivery system of claim 1 wherein the fill tube comprises a transverse dimension of about 1 mm to about 2 mm.

8. The delivery system of claim 1 wherein an outer transverse dimension of the fill tube is configured to slide within an inner lumen of the inflation port and provide a seal therebetween for viscous fluids.

9. The delivery system of claim 1 wherein the tab comprises an extension of a body portion of the endoluminal prosthesis.

10. The delivery system of claim 1 wherein the tab comprises an extension of a distal self-expanding member of the endoluminal prosthesis.

11. The delivery system of claim 10 wherein the distal self-expanding member and the tab comprise a metal.

12. The delivery system of claim 11 wherein the metal comprises NiTi.

13. A method of releasing a fill tube of a delivery catheter from an inflation port of an inflatable portion of an inflatable endoluminal prosthesis, comprising:

delivering an endoluminal prosthesis to a treatment site, the endoluminal prosthesis being releasably secured to a proximal section of a delivery catheter, the endoluminal prosthesis including an inflatable portion with an interior volume in fluid communication with an inflation port, a proximal end of a fill tube of the delivery catheter being releasably coupled to the inflation port with a fill tube retention mechanism that releasably secures a fill tube lumen of the fill tube in fluid communication with the inflation port, the fill tube retention mechanism comprising:

a tab disposed at a distal end of the endoluminal prosthesis in fixed relation to the inflation port and including an aperture that is separated from the inflation port by a predetermined distance, a fitting secured to a proximal portion of the fill tube and which extends laterally from the fill tube, at least a portion of the fitting being sized to pass through the aperture such that the aperture closely fits an outer transverse surface of the fitting, the fitting being disposed a distance from the proximal end of the fill tube such that the fill tube may be engaged with the inflation port while the fitting is disposed within the aperture, the fitting having a passage therethrough, and a release wire having an outer transverse dimension and axial bending stiffness that allows the release wire to pass through the passage and mechanically capture the tab to the fitting such that a portion of the tab is disposed between the release wire and the fill tube, and wherein the release wire may be retracted from the passage to release the portion of the tab; and releasing the fitting from the tab by retracting the release wire from the passage such that the tab is no longer mechanically captured to the fitting with the portion of the tab disposed between the fill tube and the release wire.

14. The method of claim 13 wherein the release wire extends from the fitting to a distal end of the delivery catheter and is coupled to a release mechanism disposed at the distal end of the delivery catheter and further comprising applying axial tension and displacement to the release wire with the release mechanism in order to axially retract the release wire from the passage and release the fitting from the tab.

15. The delivery system of claim 13 wherein the passage comprises an axial passage that is substantially parallel to the fill tube lumen, and further comprising axially retracting the release wire from the passage to release the fitting from the tab.

* * * * *